United States Patent [19]
Katoh et al.

[11] Patent Number: 5,648,601
[45] Date of Patent: Jul. 15, 1997

[54] APPARATUS FOR ANALYZING AIR/FUEL RATIO SENSOR CHARACTERISTICS

[75] Inventors: Kazunori Katoh; Haruyoshi Kondo, both of Anjo; Masayuki Matsui, Toyoake; Naoki Katayama, Nagoya; Yasushi Yamada, Nishikamo-gun; Hideaki Takahashi, Nisshin; Kunio Fukuda, Nagoya, all of Japan

[73] Assignees: Toyota Jidosha Kabushiki Kaisha; Kabushiki Kaisha Toyota Chuo Kenkyusho, both of Aichi-ken, Japan

[21] Appl. No.: 557,631

[22] Filed: Nov. 14, 1995

[30] Foreign Application Priority Data

Nov. 14, 1994 [JP] Japan .................................. 6-304355

[51] Int. Cl.$^6$ .................................................. G01N 7/00
[52] U.S. Cl. .................................................. 73/1 G
[58] Field of Search .................. 73/1 G, 865.6, 73/118.1, 23.32

[56] References Cited

U.S. PATENT DOCUMENTS 5,027,646  7/1991  Mizutani et al. .

FOREIGN PATENT DOCUMENTS

| A-0273765 | 7/1988 | European Pat. Off. . |
|---|---|---|
| A-2733524 | 2/1978 | Germany . |
| A-52-95289 | 8/1977 | Japan . |
| A-55-106353 | 8/1980 | Japan . |
| A-56-159548 | 12/1981 | Japan . |
| A-57-124248 | 8/1982 | Japan . |
| A-57-163863 | 10/1982 | Japan . |
| A-57-208443 | 12/1982 | Japan . |
| A-58-22945 | 2/1983 | Japan . |
| B2-58-32655 | 7/1983 | Japan . |
| B2-61-42224 | 9/1986 | Japan . |
| B2-61-42225 | 9/1986 | Japan . |
| A-63-308554 | 12/1988 | Japan . |
| A-63-314450 | 12/1988 | Japan . |
| B2-1-15814 | 3/1989 | Japan . |
| A-1-302155 | 12/1989 | Japan . |
| A-2-45750 | 2/1990 | Japan . |
| A-2-132363 | 5/1990 | Japan . |
| A-4-287851 | 10/1992 | Japan . |
| B2-6-14733 | 2/1994 | Japan . |

*Primary Examiner*—Robert Raevis
*Attorney, Agent, or Firm*—Oliff & Berridge

[57] ABSTRACT

An apparatus for analyzing air/fuel ratio sensor characteristics makes it possible to perform highly accurate analysis of the characteristics of an air/fuel ratio sensor to be measured. The apparatus comprises a sensor attachment means in which is mounted an air/fuel ratio sensor to be measured; a gas regulation means for supplying to the sensor attachment means a gas that is substantially equivalent to components of exhaust gases from an engine, or some components thereof; a control means for comparing an output from the air/fuel ratio sensor to be measured mounted in the sensor attachment means and an output from a reference stoichiometric air/fuel ratio sensor at the stoichiometric air/fuel ratio of the engine, to obtain a deviation therebetween and to obtain from a history of this deviation over time the composition and flow rate of gases to be controlled to compensate for this deviation, and issuing appropriate instructions to the gas regulation means; and an air/ratio measurement means for measuring a time average of the thus controlled air/fuel ratio.

28 Claims, 20 Drawing Sheets

CONFIGURATION OF APPARATUS FOR ANALYZING AIR-FUEL RATIO SENSOR CHARACTERISTICS

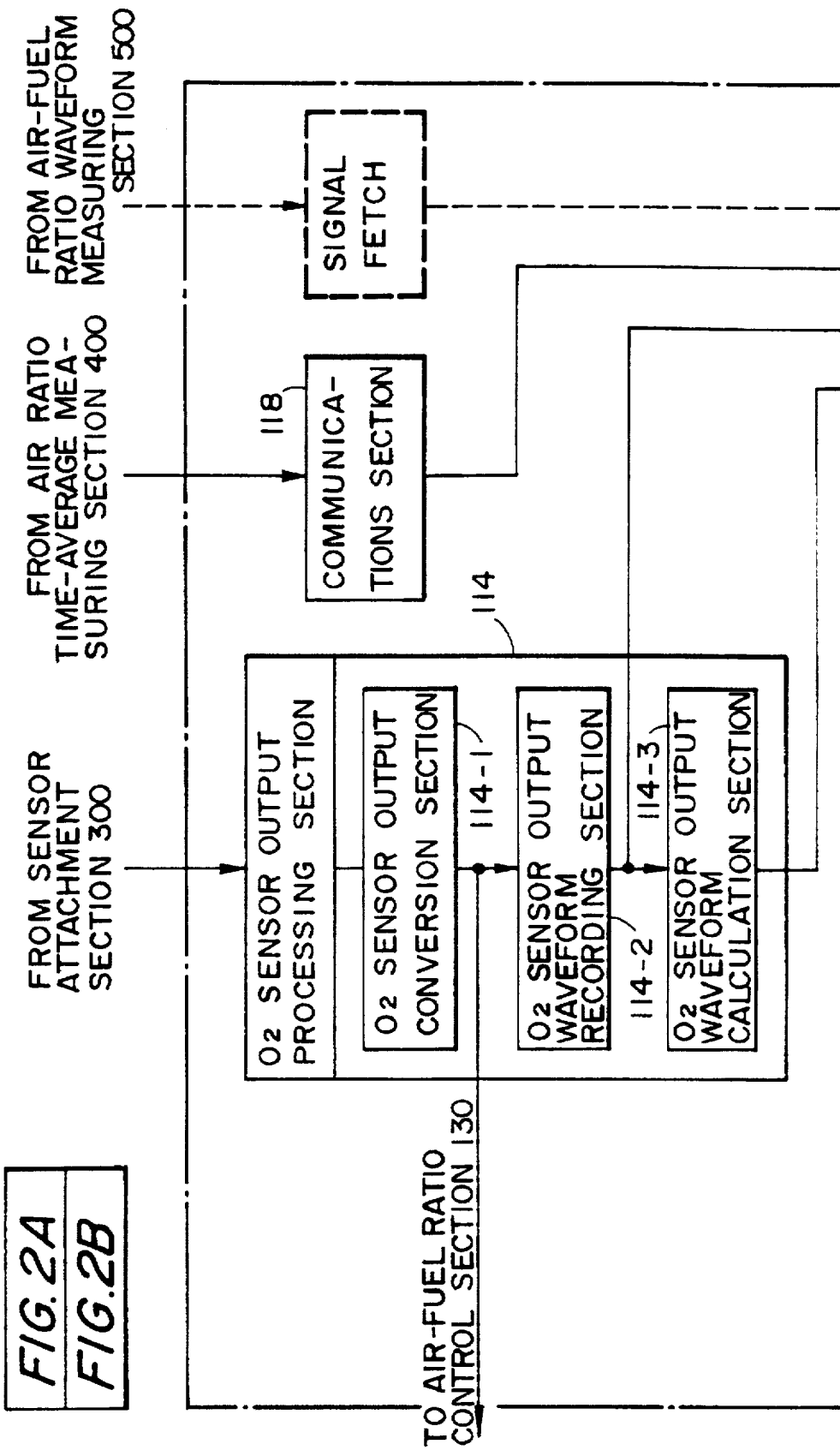

CONFIGURATION OF VOLTAGE-DIVIDER TYPE
OF RESISTANCE - VOLTAGE CONVERSION CIRCUIT

CONFIGURATION OF TEMPERATURE CONTROL SECTION 120

EXAMPLE OF TEMPERATURE-INCREASE PATTERN
FOR THEORETICAL AIR-FUEL RATIO SENSOR

CONFIGURATION OF SYSTEM DELAY COMPENSATION CALCULATION SECTION

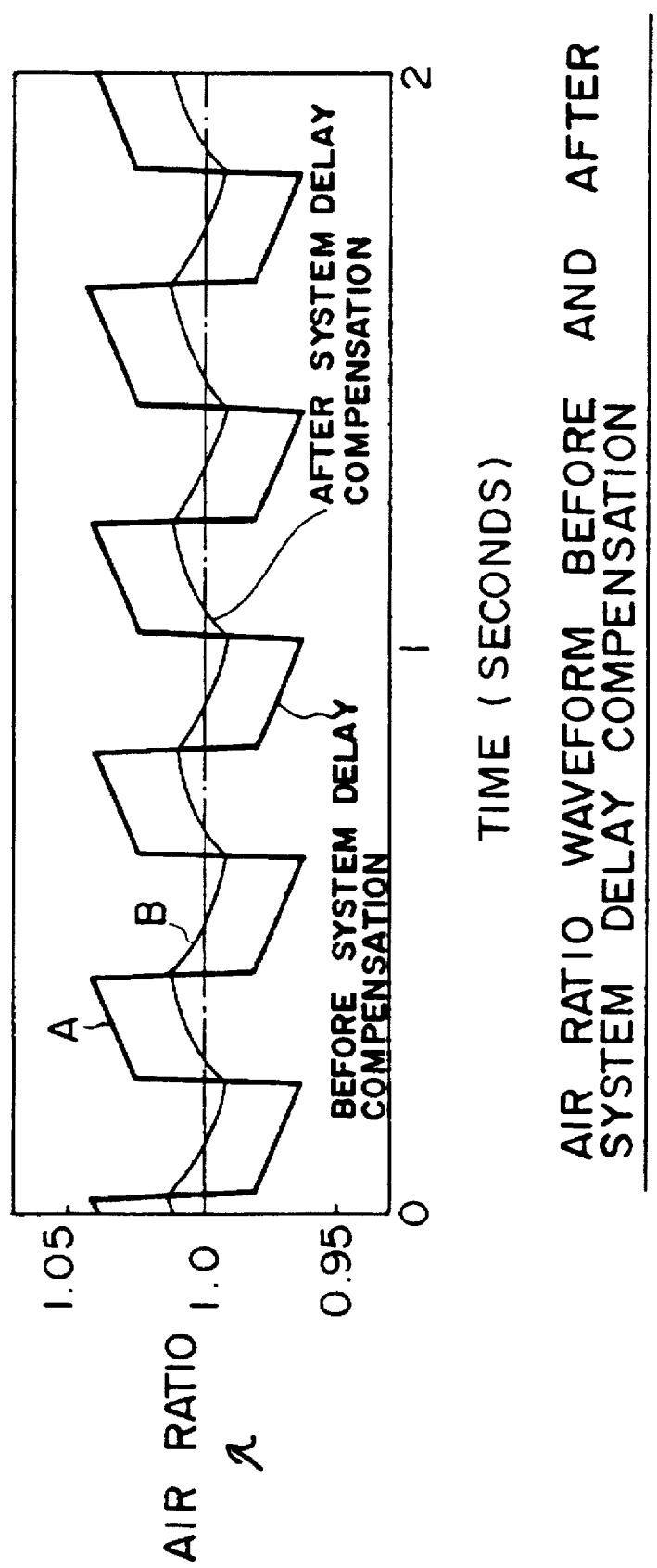

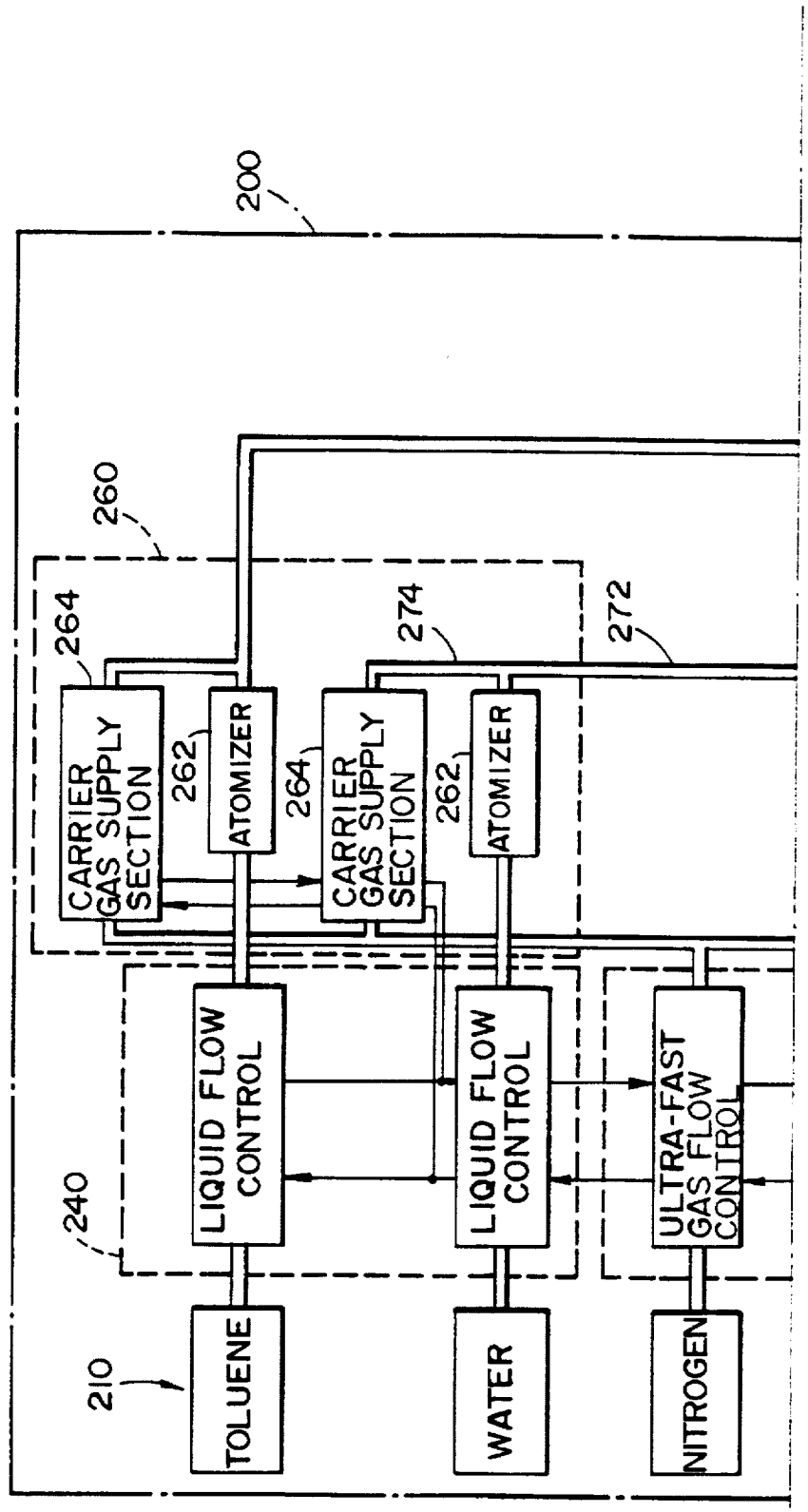

TYPICAL AIR-FUEL RATIO CONTROL STATE

AIR-FUEL RATIO CONTROL WITH SKIPS OF DIFFERENT
MAGNITUDES ON OPPOSITE SIDES
(SECOND AIR-FUEL RATIO CONTROL SYSTEM)

EXAMPLE OF CROSS SECTION THROUGH SENSOR ATTACHMENT HOLDER OF PRIOR-ART APPARATUS

EXAMPLE OF CROSS SECTION THROUGH SENSOR ATTACHMENT HOLDER OF PRIOR-ART APPARATUS (WITH CORE REMOVED)

EXAMPLE OF CROSS SECTION THROUGH SENSOR ATTACHMENT HOLDER OF PRIOR-ART APPARATUS (WITH POSITIONS OF SMALL HOLES DISPLACED)

CROSS SECTION ALONG B-B OF FIG. 17

CROSS SECTION ALONG A-A OF FIG. 16

RELATIONSHIP BETWEEN AIR RATIO TIME-AVERAGE VALUES MEASURED BY THIS APPARATUS AND ACTUAL ENGINE

RELATIONSHIP BETWEEN AIR RATIO CONTROL PERIODS MEASURED BY THIS APPARATUS AND ACTUAL ENGINE

FIG. 21
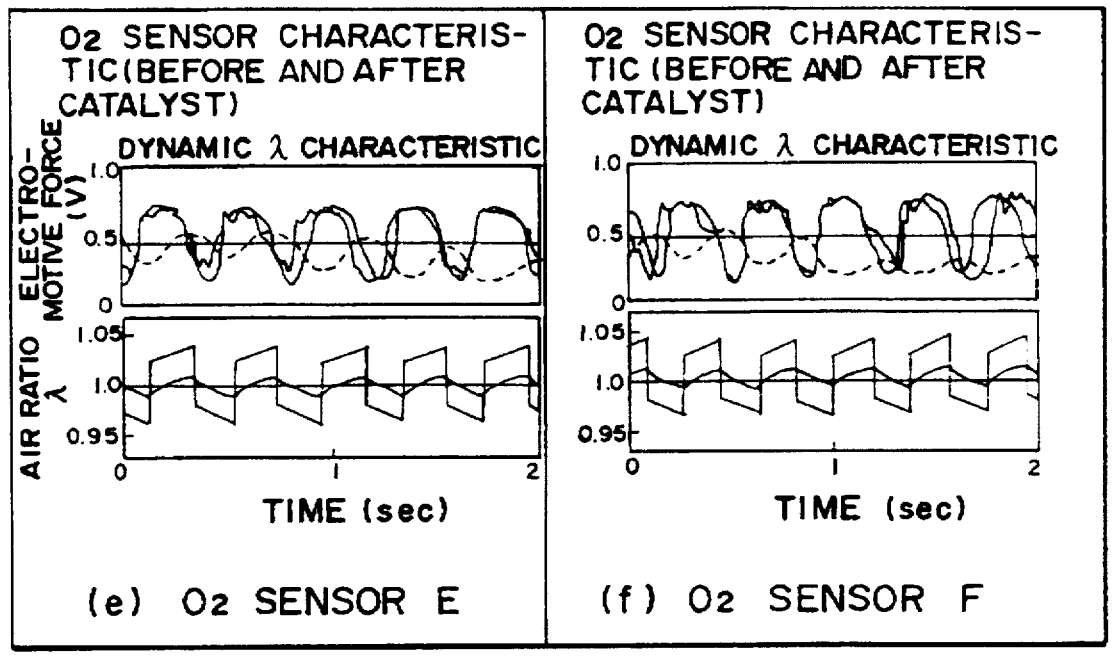
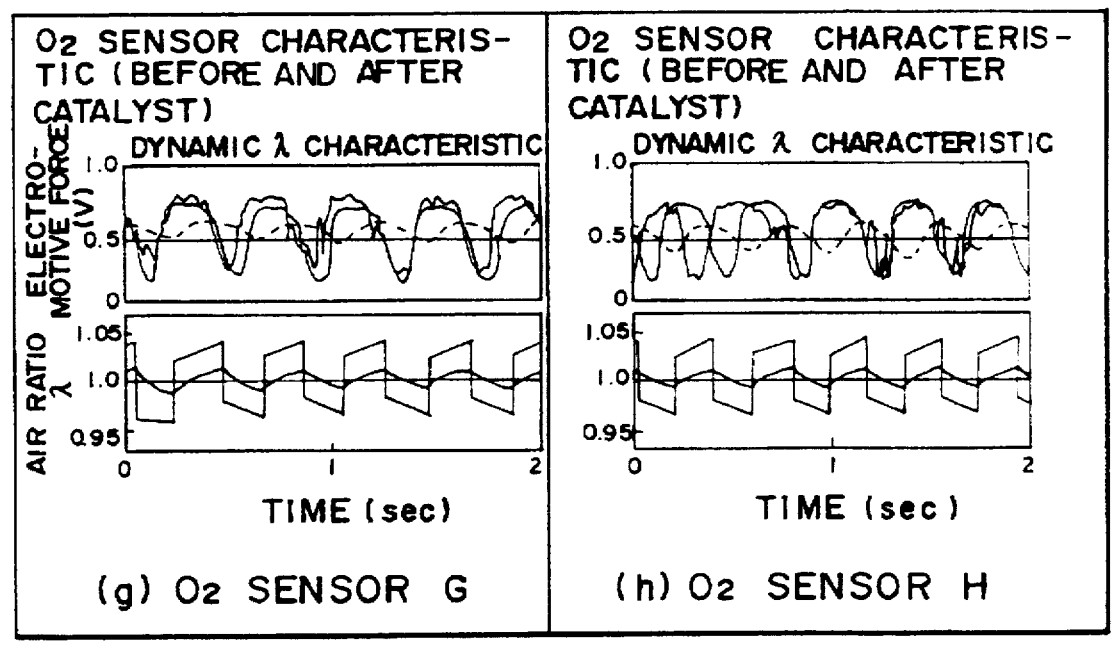

FIG. 23
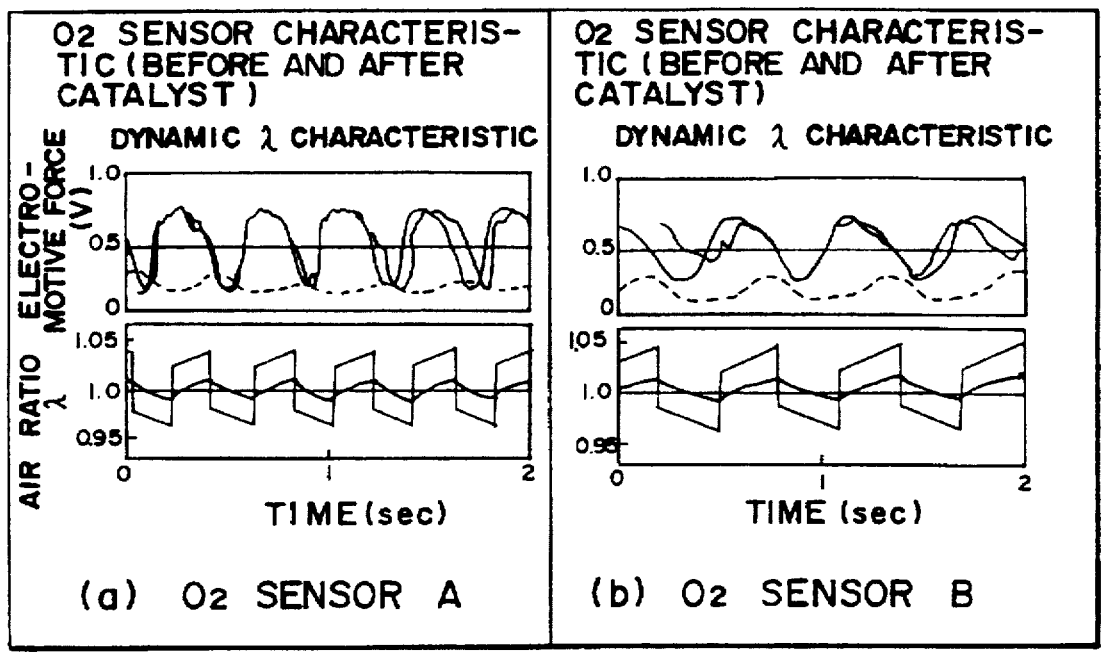
(a) O2 SENSOR A  (b) O2 SENSOR B
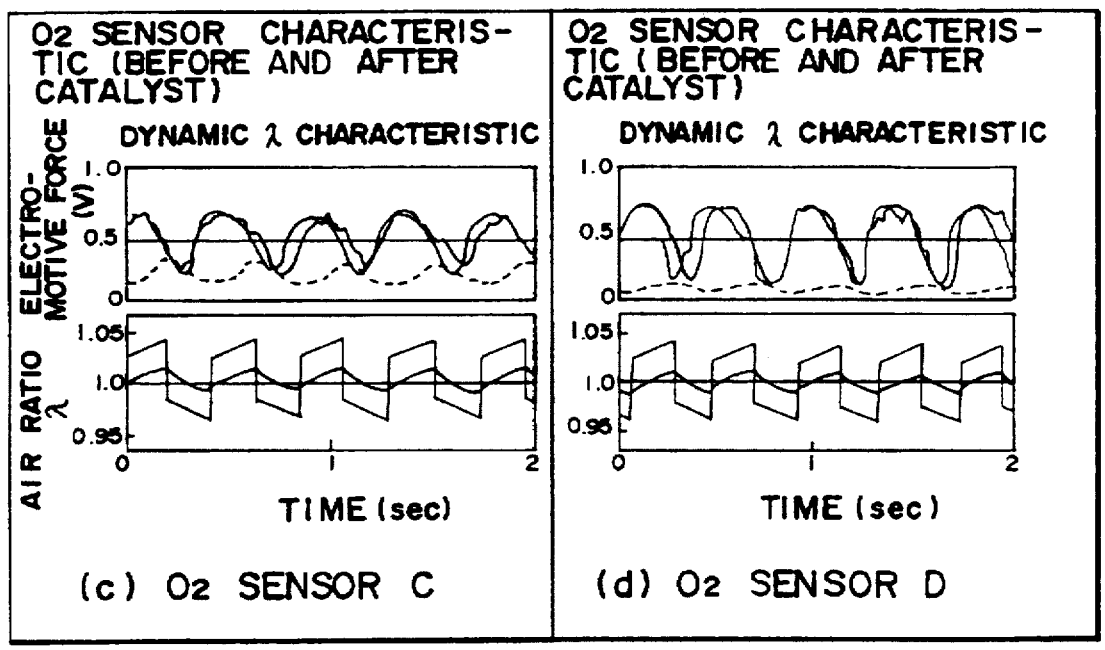
(c) O2 SENSOR C  (d) O2 SENSOR D

APPARATUS FOR ANALYZING AIR/FUEL RATIO SENSOR CHARACTERISTICS

BACKGROUND OF THE INVENTION

1. Field of the Invention

This invention relates to an apparatus for analyzing air/fuel ratio sensor characteristics.

2. Description of the Related Art

An exhaust purifying system that uses a three-way catalyst is often used for the internal combustion engine of a vehicle such as an automobile, to greatly reduce the harmful components discharged in the exhaust. The basic function of a three-way catalyst is to efficiently purify all three principal harmful components contained in comparatively high concentrations in such exhaust gases, which are nitrogen oxides ($NO_x$), carbon monoxide (CO), and hydrocarbons (HC). However, the purifying efficiencies of the three-way catalyst are greatly dependent upon the air/fuel ratio (air ratio λ) of the exhaust, as shown in FIG. 22. In other words, when the air/fuel ratio of the exhaust is fuel-rich (hereinafter abbreviated to "rich"), the purifying efficiencies with respect to carbon monoxide (CO) and hydrocarbons (HC) drop; conversely, when it is fuel-lean (hereinafter abbreviated to "lean"), the purifying efficiency with respect to nitrogen oxides ($NO_x$) drop dramatically. As a result, the range within which the purifying efficiency of the three-way catalyst with respect to each of the three principal harmful components is high is limited to an extremely narrow range (of within 1%) in the vicinity of the stoichiometric air/fuel ratio. This means that the (time-averaged) air/fuel ratio of the exhaust must be controlled precisely at the stoichiometric air/fuel ratio in order to make the most of the intrinsic function (purifying efficiency with respect to the three harmful components) of the three-way catalyst.

If air/fuel ratio control is provided by an open-loop control method that does not use an air/fuel ratio sensor, it has been determined that the accuracy of the air/fuel ratio is mainly dependent on the accuracies of an air flowmeter and fuel flowmeter. To ensure highly accurate air/fuel ratio control with this method, the two flowmeters are required to have extremely high measuring accuracies, or rather, extremely high manufacturing accuracies. However, it is not easy to satisfy the demands for the above described preferred precise (to within 1%) air/fuel ratio control with today's levels of manufacturing technology, even if the manufacturing accuracy of these flowmeters could be raised to the maximum.

In such a case, it is usual to employ a stoichiometric air/fuel ratio sensor (hereinafter called "O2 sensor") for the exhaust to precisely measure a deviation from the stoichiometric air/fuel ratio, then apply precise stoichiometric air/fuel ratio control by a closed-loop control method. This closed-loop control method differs from the above described open-loop control method in that the accuracy of the air/fuel ratio control that provides depends mainly on the accuracy with which the air/fuel ratio sensor detects the air/fuel ratio; the accuracies of the above two flowmeters have only a secondary effect. In other words, if there is any deviation in the air/fuel ratio detection characteristic of the air/fuel ratio sensor when the closed-loop control method is used, it will have a direct effect on errors in air/fuel ratio control. Therefore, the air/fuel ratio detection accuracy of a stoichiometric air/fuel ratio sensor is an important factor affecting the performance of this three-way catalyst type of exhaust purifying system. That is why it is essential during the fabrication of a stoichiometric air/fuel ratio sensor to perform a complete check on the accuracy with which it detects the air/fuel ratio.

Apparatuses for checking the air/fuel ratio detection accuracy of stoichiometric air/fuel ratio ($O_2$) sensors are known, such as the $O_2$ sensor evaluation apparatuses disclosed in Japanese Patent Nos. 1417297 and 1417298. With such an evaluation apparatus, the characteristics of a stoichiometric air/fuel ratio ($O_2$) sensor can be evaluated to an accuracy on the order of 1%, converted into an air/fuel ratio detection accuracy. Other related patents are listed in Table 1.

TABLE 1

| Applicant (Author) | Filing Date (date of receipt) | Number | Content | | |
|---|---|---|---|---|---|
| | | | Test Conditions | Evaluated Value | Object of Evaluation |
| NGK SPARK PLUG CO LTD | Dec. 10, 1987 | JP-A-63-314450 | Combustion exhaust | $D_R$ | Control air/fuel ratio |
| | June 22, 1988 | Journal of the Society of Automotive Engineers of Japan vol. 42, No. 11 | Combustion exhaust and bottled gases | | |
| HGK INSULATORS LTD | Nov. 14, 1988 | JP-A-2-132363 | Combustion exhaust | Response time | Control air/fuel ratio |
| | Aug. 5, 1988 | JP-A-2-45750 | Engine exhaust | $D_R$ | Emissions |
| MITSUBISHI MOTORS CORP | May 31, 1988 | JP-A-1-302155 | Bottled gases | Static & Response characteristics | |
| MAZDA MOTOR CORP | Dec. 14, 1987 | JP-A-1-155257 | Combustion exhaust | Response time | Emissions |
| | June 10, 1987 | JP-A-63-308554 | Combustion exhaust | Response time | Emissions |
| NISSAN MOTOR CO LTD | Aug. 4, 1981 | JP-A-58-22945 | Combustion exhuast | $D_R$ | Control air/fuel ratio |
| | June 18, 1981 | JP-A-57-208443 | Combustion or engine exhaust | Response waveform | Control frequency |
| | Apr. 1, 1981 | JP-A-57-163863 | Combustion exhaust | Response time | |
| | Jan. 26, 1981 | JP-A-57-124248 | Combustion or | $D_R$ | Emissions |

TABLE 1-continued

| Applicant (Author) | Filing Date (date of receipt) | Number | Test Conditions | Evaluated Value | Object of Evaluation |
|---|---|---|---|---|---|
| | Feb. 5, 1976 | JP-A-52-95289 | engine exhaust Combustion exhaust | Response waveform | |
| TOYOTA MOTOR CORP | Feb. 9, 1979 | JP-A-55-106353 | Bottled gases | Response waveform | Catalyst function, etc |
| | Nov. 10, 1977 | JP-B-58-32655 | | Impedance | |
| TOYOTA MOTOR CORP/TOYOTA CENTRAL RES & DEV LAB INC | Nov. 17, 1977 | JP-B-61-42225 | Combustion exhaust | Equilibrium λ | Control air/ fuel ratio |
| | Oct. 15, 1977 | JP-B-61-42224 | Bottled gases | $D_R$ | |

Sensors that use either a zirconia oxygen concentration cell or a titanium dioxide resistor are widely used as stoichiometric air/fuel ratio ($O_2$) sensors for this three-way catalyst type of exhaust purifying system.

If a zirconia oxygen concentration cell type of stoichiometric air/fuel ratio ($O_2$) sensor is used, output is in the form of an electromotive force, so that rich or lean can be determined from comparing the electromotive force of the sensor with a reference voltage. A constant voltage (usually 0.45 V) corresponding to the electromotive force at the stoichiometric air/fuel ratio is used as this reference voltage. A zirconia oxygen concentration cell type of stoichiometric air/fuel ratio ($O_2$) sensor has extremely good characteristics in that the electromotive force has a low dependency on temperature, which means that there is no need to adjust the reference voltage for temperature, making it extremely easy to use, and thus it is the most widely used type of sensor.

With a titanium dioxide resistor type of stoichiometric air/fuel ratio ($O_2$) sensor, output is in the form of a resistance, so that rich or lean can be determined from comparing the resistance of the sensor with a reference resistance. A constant resistance corresponding to the resistance at the stoichiometric air/fuel ratio is used as the reference resistance, but the sensor resistance is highly dependent on temperature, so that it is necessary to adjust the reference resistance for temperature when the sensor is used over a wide temperature range. This means that the air/fuel ratio control system may have to use a method of automatically adjusting the reference resistance.

Regardless of whether the stoichiometric air/fuel ratio ($O_2$) sensor is a zirconia oxygen concentration cell type or a titanium dioxide resistor type, it is capable of operating at temperatures of approximately 400° C. or above. And thus a characteristic that is ideal for detecting a stoichiometric air/fuel ratio with an error on the order of 1% can be obtained by selecting sensors of quality after fabrication. Therefore, both types of sensor can function at their best in a three-way catalyst type of exhaust purifying system, which will help immensely in reducing pollution in Earth's environment.

However, recent increases in the numbers of automobiles in use and in the weights of the vehicles themselves have led to a great deal of public concern relating to a greater reduction in the quantity of harmful components discharged into the atmosphere, while the trend toward reducing these harmful components has become dull. To address this public concern, not only is it necessary to improve catalysts and engines themselves, but it has become even more important to improve stoichiometric air/fuel ratio ($O_2$) sensors. In other words, stoichiometric air/fuel ratio ($O_2$) sensors must now be able to achieve a higher accuracy of air/fuel ratio detection than that of conventional products.

To provide a stoichiometric air/fuel ratio ($O_2$) sensor of a quality that greatly exceeds that of conventional products, it is obviously necessary that improvements to the art should start at the design stage and extend through the entire fabrication process. But this does not mean that the above concerns will be addresses by design and fabrication improvements alone. Regardless of how the design and fabrication process are improved, product quality cannot be verified without a means of precisely measuring the accuracy with which the air/fuel ratio of the resultant stoichiometric air/fuel ratio ($O_2$) sensor is detected. If product quality cannot be verified, the effects of design and fabrication improvements cannot be verified either, and thus it is clear that proof of such improvements cannot be obtained.

In other words, a key point in the development and supply of a high-quality stoichiometric air/fuel ratio ($O_2$) sensor is a precise means of measuring the air/fuel ratio detection accuracy thereof. To test a stoichiometric air/fuel ratio ($O_2$) sensor for such a higher level of accuracy, it is essential to use a testing device (characteristic-analyzing apparatus) that has such a higher level of accuracy itself.

As stated previously, a prior-art apparatus for analyzing air/fuel ratio ($O_2$) sensor characteristics is capable of testing a stoichiometric air/fuel ratio ($O_2$) sensor for an accuracy on the order of 1%. However, an apparatus for analyzing air/fuel ratio ($O_2$) sensor characteristics that has an even higher accuracy has not yet been invented.

SUMMARY OF THE INVENTION

An objective of this invention is to address the above described concerns relating to the prior-art apparatus for analyzing air/fuel ratio sensor characteristics and thus supply an apparatus for analyzing air/fuel ratio sensor characteristics that has an accuracy that is an order of magnitude higher than that of the prior art.

Investigation of Prior-Art Technology

When a prior-art apparatus for analyzing air/fuel ratio ($O_2$) sensor characteristics is used to measure the air/fuel ratio detection accuracy of an air/fuel ratio ($O_2$) sensor to be measured, there are many problems preventing further improvements in the accuracy of the testing device.

An apparatus for analyzing air/fuel ratio ($O_2$) sensor characteristics is usually a controller of an air/fuel ratio of a test gas by filting it to that of an actual engine exhaust by providing a combustion exhaust or model gas (step 1). The result of this control is measured as the characteristic of the air/fuel ratio ($O_2$) sensor (step 2).

Therefore, those controlling and measuring accuracies are relevant to the accuracy of an apparatus for analyzing air/fuel ratio ($O_2$) sensor characteristics.

A first problem is difficulty in achieving the same control state of air/fuel ratio (control value) with that of an actual engine, and in improving the degree of similarity to an actual engine.

A second problem is inadequacy in the accuracy with which the air/fuel ratio control result is measured.

This invention was devised after deep consideration of these problems. Thus it enables a dramatic improvement in accuracy by solving these problems and providing effective countermeasures therefor.

The present inventors have conducted detailed investigations of the accuracy of the air/fuel ratio control state, with the following results:

In an internal combustion engine, the relative magnitude of the amount of harmful components discharged during test mode (through a three-way catalyst) exhibited a high level of correlation with the relative magnitude of deviations from the stoichiometric air/fuel ratio of the control air/fuel ratio waveform during test mode.

When it came to investigating in further detail the characteristic of a stoichiometric air/fuel ratio ($O_2$) sensor that is linked to the quantity of harmful components discharged during test mode (through a three-way catalyst), which ought to be as easy as possible to evaluate, the quantity of harmful components discharged exhibited a comparatively high level of correlation with the control air/fuel ratio (time-averaged value) at predetermined steady engine conditions (engine speed and intake pressure) even though it was not necessarily possible to determine the entire control air/fuel ratio waveform during test mode.

The predetermined steady engine conditions (engine speed and intake pressure) that provided a high correlation between the quantity of harmful components discharged during test mode (through a three-way catalyst) and the control air/fuel ratio (time-averaged value) depended on the type of automobile, the engine model, the transmission model, the type of the stoichiometric air/fuel ratio ($O_2$) sensor, and the exhaust testing mode.

Under the predetermined steady engine conditions engine speed and intake pressure that provided a high correlation between the quantity of harmful components discharged during test mode (after purifying with a three-way catalyst) and the control air/fuel ratio (time-averaged value), any changes in the control air/fuel ratio (time-averaged value), however small, had an effect on the quantity of harmful components discharged, so they cannot be ignored.

Even if other conditions were assumed to be fixed, any change in the flow velocity of the exhaust with respect to the stoichiometric air/fuel ratio ($O_2$) sensor had the effect of changing the control air/fuel ratio (time-averaged value).

Even if other conditions were assumed to be fixed, any change in the temperature of the stoichiometric air/fuel ratio ($O_2$) sensor had the effect of changing the control air/fuel ratio (time-averaged value).

Even if other conditions were assumed to be fixed, any change in the period at which air/fuel ratio control was applied had the effect of changing the control air/fuel ratio (time-averaged value).

Even if other conditions were assumed to in fixed, any change in the air/fuel ratio control constants (delay time, skip, and ramp rate) had the effect of changing the control air/fuel ratio (time-averaged value).

Even if other conditions were assumed to be fixed, any change in the composition of the exhaust had the effect of changing the control air/fuel ratio (time-averaged value).

The above research findings clearly raises the problems with the prior-art apparatus.

In the prior art, it was not known that the engine conditions that show a high correlation with the quantity of harmful components discharged during test mode (through a three-way catalyst) are dependent on the type of automobile, engine model, transmission model, type of stoichiometric air/fuel ratio ($O_2$) sensor, and exhaust testing mode. Thus the prior-art apparatus did not have optimized engine conditions for characteristic evaluation.

In the prior art, there was no air/fuel ratio measurement means capable of accurately measuring a 0.1% change in the air/fuel ratio. Thus only changes on the order of 1% were measured efficiently.

In the prior art, it was not known that exhaust flow velocity exerts a strong effect on the control air/fuel ratio. Thus the prior-art apparatus did not have optimized exhaust flow velocity of the predetermined engine conditions for characteristic evaluation.

In the prior art, it was not known that the sensor temperature exerts a strong effect on the control air/fuel ratio. Thus the prior-art apparatus did not have optimized sensor temperature of the predetermined engine conditions for characteristic evaluation In the prior art, it was not known that the period at which air/fuel ratio control is applied exerts a strong effect on the control air/fuel ratio. Thus the prior-art apparatus did not have optimized air/fuel ratio control period of the predetermined engine conditions for characteristic evaluation.

In the prior art, it was not known that the air/fuel ratio control constants (delay time, skip, and ramp rate) exert a strong effect on the control air/fuel ratio. Thus the prior-art apparatus did not have optimized air/fuel ratio control constants (delay time, skip, and ramp rate) of the predetermined engine conditions for characteristic evaluation.

In the prior art, it was not known that the exhaust composition exerts a strong effect on the control air/fuel ratio. Thus the prior-art apparatus did not have optimized exhaust composition of the predetermined engine conditions for characteristic evaluation.

Therefore, the characteristic measured by a prior-art apparatus for analyzing the characteristics of a stoichiometric air/fuel ratio ($O_2$) sensor does not have good correlation with the control air ratio that is measured with an actual engine.

Construction and Operation of the Apparatus of the Invention

An apparatus for analyzing air/fuel ratio sensor characteristics in accordance with a first aspect of this invention comprises:

a sensor attachment means in which is mounted an air/fuel ratio sensor to be measured;

a gas regulation means for supplying to the sensor attachment means an exhaust gas from an engine, or some components thereof;

a control means for comparing an output value from the air/fuel ratio sensor and an output reference value from a first reference air/fuel ratio sensor at the stoichiometric air/fuel ratio of the engine to obtain a deviation, obtaining from a history of the deviation over time a composition and flow rate of gases for correction, and controlling the gas regulation means to control the air/fuel ratio of the gas; and an air/fuel ratio measurement means for measuring a time average of the thus controlled air/fuel ratio;

the air/fuel ratio measurement means comprising:

a second reference air/fuel ratio sensor for detecting the air/fuel ratio of the gas supplied from the gas regulation means;

a first calculation means for determining the flow rate of a gas to be added to bring the air/fuel ratio of the gas supplied from the gas regulation means to the stoichiometric air/fuel ratio, on the basis of an output value of the second reference air/fuel ratio sensor;

a supplementary gas control means for controlling the flow rate of a supplementary gas to be added, on the basis of the thus obtained calculation result; and a second calculation means for calculating the air/fuel ratio of the gas supplied from the gas regulation means, based on the amount of the supplementary gas that is supplied;

whereby characteristic analysis of the air/fuel ratio sensor to be measured is performed on the basis of the air/fuel ratio calculated by the second calculation means.

The air/fuel ratio measurement means preferably comprises:

a fixed flow rate supply means for separating a gas at a fixed flow rate from an exhausted gas from the sensor attachment means; and a gas reaction means for causing the separated gas to react with the supplementary gas added by the supplementary gas control means and supplying the thus reacted gas to the second reference air/fuel ratio sensor.

The configuration could be such that the supplementary gas control means is constructed in such a manner as to supply either hydrogen or oxygen selectively as the supplementary gas;

the second reference air/fuel ratio sensor is constructed to detect whether the reacted gas is shifted towards rich or towards lean;

the first calculation means determines whether the reacted gas is rich or lean from an output value of the second reference air/fuel ratio sensor, and controls the supplementary gas control means in such a manner that oxygen is gradually added until the stoichiometric air/fuel ratio is achieved when the reacted gas is rich, or hydrogen is gradually added until the stoichiometric air/fuel ratio is achieved when the reacted gas is lean; and the second calculation means calculates and displays a time average of the air/fuel ratio when the reacted gas has reached a state in the vicinity of the stoichiometric air/fuel ratio by the addition of oxygen or hydrogen.

The apparatus of this invention could further comprise:

an air/fuel ratio waveform measurement means for measuring changes in the waveform of the controlled air/fuel ratio;

whereby a characteristic of the air/fuel ratio sensor to be measured is analyzed on the basis of measured waveform changes.

The gas regulation means is preferably constructed to supply a gas comprising the following gas components:

nitrogen ($N_2$), water vapor ($H_2O$), carbon monoxide (CO), hydrogen ($H_2$), hydrocarbons (HC), oxygen ($O_2$), and nitric oxide (NO).

The gas regulation means is further preferably constructed to supply a gas that also comprises carbon dioxide ($CO_2$).

The gas regulation means is further preferably constructed such that the hydrocarbon (HC) gas is at least one selected from the group consisting of ethylene ($C_2H_4$), toluene ($C_7H_8$), and propylene ($C_3H_6$).

The gas regulation means is further preferably constructed to prepare a gas having a temperature, a flow velocity, a composition, and an air/fuel ratio equivalent to an engine exhaust gas under high load conditions.

The apparatus of this invention is preferably constructed such that the gas regulation means comprises:

a liquid flow rate control means for controlling a flow rate of those of the exhaust gas components which are supplied in a liquid state;

a liquid atomization means for atomizing the thus supplied liquid component;

a high-speed gas flow rate control means for controlling at a high speed a supply flow rate of those of the gas components which are supplied in a gaseous state; and mixing means for mixing the exhaust gas components supplied from the liquid atomization means and from the high-speed gas flow rate control means;

whereby the control means controls the flow rates of gases supplied by the liquid flow control means and the high-speed gas flow rate control means.

The sensor attachment means is preferably constructed to comprise means for heating the air/fuel ratio sensor to be measured.

The control means preferably comprises:

memory means in which is set a plurality of reference output patterns for the output reference value, air/fuel ratio control conditions for the gas regulation means, and sensor temperature control conditions for the sensor attachment means, corresponding to exhaust gas testing and measurement modes and measurement conditions of the engine;

selection means for selecting any desired exhaust gas testing and measurement modes and measurement conditions; and means for reading from the memory means reference output patterns and control conditions corresponding to the thus selected exhaust gas testing and measurement modes and measurement conditions, and controlling the gas regulation means and the sensor attachment means on the basis of read control conditions and a deviation between the read-out reference output patterns and an output from the air/fuel ratio sensor to be measured.

The sensor attachment means could comprise:

a first sensor attachment means in which a first air/fuel ratio sensor to be measured is mounted and to which is supplied a gas from the gas regulation means;

a three-way catalyst section provided downstream of the first sensor attachment means; and a second sensor attachment means provided downstream of the three-way catalyst section, in which a second air/fuel ratio sensor to be measured is mounted;

whereby the control means controls the gas regulation means on the basis of outputs from the first and second air/fuel ratio sensors to be measured.

A detailed description of the configuration and operation of the apparatus of this invention is given below.

In accordance with this invention, the air/fuel ratio sensor to be measured is mounted in the sensor attachment means. A gas that is substantially equivalent to components of exhaust gases from an engine, or some components thereof is supplied to the sensor attachment means from the gas regulation means.

During this time, the control means compares an output from the air/fuel ratio sensor to be measured that is mounted in the sensor attachment means against an output of a reference air/fuel ratio sensor at the stoichiometric air ratio (air/fuel ratio) of the engine, to obtain a deviation therebetween, obtains from a history of the deviation over time the composition and flow rate of gases to be added, and issues appropriate instructions to the gas regulation means.

In this manner, a time-average of the air/fuel ratio is made to be substantially the same as the stoichiometric air ratio (stoichiometric air/fuel ratio) by obtaining the composition and flow rate of gases to be added, on the basis of an output signal (electromotive force or resistance) from the air/fuel ratio sensor to be measured, and controlling the system in such a manner that the air/fuel ratio approaches the stoichiometric air ratio (air/fuel ratio).

However, the swapping of individual air/fuel ratio ($O_2$) sensors to be measured may cause very small deviations, i.e. less than 1% differences between individual $O_2$ sensors from the stoichiometric air ratio (air/fuel ratio). Research conducted by the present inventors has showed that a value of air ratio that is controlled by the air/fuel ratio ($O_2$) sensor to be measured has a great effect on exhaust emissions. Therefore, a controlled value of air ratio is the most important characteristic for an $O_2$ sensor.

The apparatus of this invention uses an air/fuel ratio measurement means to measure directly and accurately a value of air ratio which is the most important characteristic for an $O_2$ sensor.

In other words, the air/fuel ratio measurement means of this invention is constructed to comprise a reference air/fuel ratio sensor, a first calculation means, a supplementary gas control means, and a second calculation means.

It uses the reference air/fuel ratio sensor to detect the air/fuel ratio of a gas supplied from the gas regulation means and outputs a corresponding detection signal to the first calculation means.

The first calculation means detects the direction in which the air/fuel ratio of the supplied gas deviates from the stoichiometric air/fuel ratio, based on the output of the reference air/fuel ratio sensor, and calculates the flow rate of the gas to be added to bring the air/fuel ratio of the supplied gas back towards the stoichiometric air/fuel ratio.

The supplementary gas control means supplies the supplementary gas to be added at the flow rate determined by this calculation result.

In this case, it is preferable that the air/fuel ratio measurement means is constructed to comprise a fixed flow rate supply means and a gas reaction means, to make the addition of this supplementary gas easier.

That is to say, the fixed flow rate supply means separates off a quantity of gas at a fixed flow rate from the gas exhausted from the sensor attachment means.

The supplementary gas control means adds the supplementary gas at the appropriate supplementary flow rate to the thus separated gas, and supplies the resultant mixture to the gas reaction means.

The gas reaction means causes the separated gas flow to react with the supplementary gas and supplies the resultant gas to the reference air/fuel ratio sensor.

During this time, the second calculation means can calculate the air/fuel ratio of the supplied gas, based on factors such as the amount of supplementary gas that is supplied. In other words, if the air/fuel ratio of the sampled supplied gas differs from the stoichiometric air/fuel ratio, it is generally possible to determine whether it is fuel or air that is insufficient. Accordingly, if it is possible to determine which gas is insufficient and in what proportion it is insufficient, the gas can be returned to the stoichiometric air/fuel ratio by supplementing this insufficiency. In addition, the air/fuel ratio of the supplied gas could be calculated from the type and amount of gas that is supplied.

Using such a method, the air/fuel ratio measurement means of this invention can obtain a value for the air ratio (air/fuel ratio) according to the air/fuel ratio sensor to be measured with an accuracy of 0.1%, and thus the apparatus of this invention makes it possible to analyze the characteristic of the air/fuel ratio sensor to be measured to a high level of accuracy.

To this end, the control means preferably comprises:

an air ratio (air/fuel ratio) control means for comparing an output of the stoichiometric air/fuel ratio ($O_2$) sensor to be measured that is mounted in the sensor attachment means and an output of a reference stoichiometric air/fuel ratio ($O_2$) sensor at the stoichiometric air ratio (air/fuel ratio) of the engine to obtain a deviation therebetween, controlling the air ratio (air/fuel ratio) on the basis of a history of this deviation over time, obtaining a gas composition and flow rate corresponding to this air ratio (air/fuel ratio), and issuing instructions to the gas regulation means;

a temperature control means for controlling the temperature of other components of the apparatus; and a measurement control means for performing the control and measurement for the other components of the apparatus.

Highly accurate control is enabled by dividing the control means by function in this manner.

The apparatus of this invention also preferably comprises an air/fuel ratio waveform measurement means (high-speed air/fuel ratio meter) that measures the changing waveform of the controlled air ratio (air/fuel ratio) with which it measures the time-dependent waveform of the controlled air ratio (air/fuel ratio).

That is to say, a value of air ratio that is controlled to suit the stoichiometric air/fuel ratio ($O_2$) sensor to be measured is the most important characteristic of an $O_2$ sensor, because it affects exhaust emissions, as described previously. Research conducted by the present inventors has shown that the next most important characteristic that affects exhaust emissions is the time-dependent waveform of the controlled air ratio (air/fuel ratio). Measuring this time-dependent waveform makes it possible to determine this second most important characteristic of the $O_2$ sensor and thus enables a deeper analysis.

The gas components used by the gas regulation means in the apparatus of this invention are preferably: nitrogen ($N_2$), water vapor ($H_2O$), carbon monoxide (CO), hydrogen ($H_2$), hydrocarbons (HC), oxygen ($O_2$), and nitrogen oxide (NO).

That is to say, these gas components have a large effect on the output (electromotive force or resistance) characteristic of the $O_2$ sensor.

Research conducted by the present inventors has shown that, of the many components within exhaust gases, those that have a large effect on the output (electromotive force or resistance) characteristic of the $O_2$ sensor are nitrogen ($N_2$), water vapor ($H_2O$), carbon monoxide (CO), hydrogen ($H_2$), hydrocarbons (HC), oxygen ($O_2$), and nitrogen oxide (NO).

This research has also shown that three components (carbon monoxide (CO), hydrogen ($H_2$), and hydrocarbons (HC)) give rise to oxidation reactions in the vicinity of the electrodes of the $O_2$ sensor, generating an electromotive force which is the most important action of an $O_2$ sensor.

This research has further shown that oxygen ($O_2$) and nitrogen oxide (NO) together with the above three components carbon monoxide (CO), hydrogen ($H_2$), and hydrocarbons (HC) give rise to oxidation reactions in the vicinity of the electrodes of the $O_2$ sensor, generating an electromotive force which is the most important action of an $O_2$ sensor.

A yet further finding of this research is that water vapor ($H_2O$) has the effect of suppressing the oxidation reaction of hydrogen ($H_2$) in the vicinity of the electrodes of the air/fuel ratio sensor. Therefore this apparatus also uses water vapor ($H_2O$) to make it possible to reproduce the effect of suppressing the oxidation reaction of hydrogen ($H_2$) by water vapor ($H_2O$), as if the sensor were mounted in the exhaust pipe of an engine. This enables accurate measurement by this apparatus of the characteristic of an $O_2$ sensor in which the oxidation reaction of hydrogen ($H_2$) has been deteriorated.

To this end, the above described configuration of the gas components used by the gas regulation means makes it possible to supply a gas that is substantially equivalent to components of exhaust gases produced by an actual engine.

The hydrocarbon (HC) gas component used by the gas regulation means of this invention is preferably any one or a combination of ethylene ($C_2H_4$), toluene ($C_7H_8$), and propylene ($C_3H_6$).

These gas components of the hydrocarbons (HC) within exhaust gases have a large effect on the output (electromotive force or resistance) characteristic of the $O_2$ sensor.

The present inventors have performed a detailed analysis of the hydrocarbons (HC) within the exhaust gases of actual engines, and have identified over 20 such components and their concentrations. When it came to ranking the effects on the output (electromotive force or resistance) characteristic of the $O_2$ sensor caused by these many components, it was ascertained that ethylene ($C_2H_4$), toluene ($C_7H_8$), and propylene ($C_3H_6$), in that order, have the greatest effect, regardless of engine conditions. Therefore this apparatus uses one or a combination of these components to reproduce the effect on the output (electromotive force or resistance) characteristic of the $O_2$ sensor caused by hydrocarbons (HC), as if the sensor were mounted in the exhaust pipe of an engine. This enables accurate measurement of output (electromotive force or resistance) characteristic of the $O_2$ sensor with respect to hydrocarbons (HC).

It is further preferable that carbon dioxide ($CO_2$) is added to the gas components used by the gas regulation means.

The research of the present inventors has shown that carbon dioxide ($CO_2$) has the effect of suppressing the oxidation reaction of carbon monoxide (CO) in the vicinity of the electrodes of the air/fuel ratio sensor. Therefore the use of carbon dioxide ($CO_2$) in this apparatus makes it possible to reproduce the effect of suppressing the oxidation reaction of carbon monoxide (CO), as if the sensor were mounted in the exhaust pipe of an engine. This enables accurate measurement by this apparatus of the characteristic of an $O_2$ sensor in which the oxidation reaction of carbon monoxide (CO) has been deteriorated.

The measurement control means in accordance with this invention also preferably comprises:

a measurement mode/condition setting means;

an $O_2$ sensor output processing means;

an $O_2$ sensor characteristic display and output means;

communications means for the air/fuel ratio measurement means (precision air ratio meter);

communications means for the air ratio (air/fuel ratio) control means; and communications means for the temperature control means.

In other words, the measurement mode/condition setting means can select any of three measurement modes provided in this apparatus, to measure the dynamic λ characteristic, transient response characteristic, or static λ characteristic. It can also set characteristic measurement conditions corresponding to each of these modes. The type of the $O_2$ sensor to be measured can also be selected thereby.

The $O_2$ sensor output processing means pre-processes a weak output (electromotive force or resistance) signal of the $O_2$ sensor to be measured to make it suitable for measurement.

If the $O_2$ sensor to be measured is of the oxygen concentration cell type, the output signal is an electromotive force on the order of 0 to 1 V. When an electromotive force is measured, the internal resistance of the $O_2$ sensor to be measured has the effect of lowering the voltage thereof. When a characteristic is measured at a comparatively low temperature, the internal resistance of the $O_2$ sensor to be measured is often high, so this effect of a drop in voltage caused by the internal resistance can easily appear. In this case, a buffer with a small input bias current is used, which reduces the voltage-drop effect caused by the internal resistance.

If the $O_2$ sensor to be measured is of the oxide semiconductor (titanium dioxide, etc) type, the output signal is a resistance of the order of 1 kΩ to 1000 kΩ. Since the amplitude of variations in the resistance due to the air ratio is extremely large (approximately three orders of magnitude), some contrivance is necessary to enable accurate measurement. One method is to apply a constant voltage between the ends of the serially-connected circuit of a fixed resistance and the $O_2$ sensor to be measured, and measure the resultant voltage divided between the resistance and the $O_2$ sensor, which has the advantage of being convenient. Another method is to measure the resistance with a logarithmic ohm-meter, which has the advantage of enabling precise measurement of resistances that vary over a wide range.

The $O_2$ sensor characteristic display and output means displays the measured characteristic of the $O_2$ sensor to be measured on a CRT display, converts the format of this data for an output device such as a plotter, and outputs the data to a floppy disk.

The communications means for the air/fuel ratio measurement means (precision air ratio meter) transfers instructions concerning measurement conditions and measurement start to the air/fuel ratio measurement means (precision air ratio meter), and also receives measured values (air ratio time-average).

The communications means for the air ratio (air/fuel ratio) control means transfers air ratio control condition instructions to the air ratio (air/fuel ratio) control means.

The communications means for the temperature control means transfers component temperature settings to the temperature control means, and also receives the current temperature.

Highly accurate control at high speeds is enabled by dividing the measurement control means by function in this manner.

The measurement control means preferably has a means for fetching signals from the air/fuel ratio waveform measurement means (high-speed air/fuel ratio meter).

This makes it possible to record the air/fuel ratio waveform data in synchronization with the measured characteristic of the $O_2$ sensor to be measured, by using the signal fetch means to fetch the output signal (air/fuel ratio waveform) from the air/fuel ratio waveform measurement means (high-speed air/fuel ratio meter).

The measurement mode/condition setting means is preferably constructed in such a manner that "air/fuel ratio control (dynamic λ characteristic) mode," "static λ characteristic (sensor output vs. air/fuel ratio (air ratio)) measurement mode," "transient response characteristic measurement mode," or any combination thereof, can be selected as the measurement mode.

Such a configuration enables makes it possible for the operator to freely switch between measuring different characteristics by selecting one of the three characteristics from a menu, thus improving efficiency.

The measurement mode/condition setting means is preferably constructed in such a manner that the optimum engine conditions (engine speed and intake pressure), exhaust flow velocity, exhaust temperature, exhaust composition, air/fuel ratio control period, and sensor temperature can be selected by inputting the type of automobile, year of manufacture, engine model, transmission model, and type of exhaust regulations corresponding to the stoichiometric air/fuel ratio ($O_2$) sensor to be measured, so that measurement can always be performed under appropriate conditions.

This configuration ensures that the optimum engine conditions (engine speed and intake pressure), exhaust flow velocity, exhaust temperature, exhaust composition, air/fuel ratio control period, and sensor temperature automatically appear as the first option on the menu when the operator inputs the type of automobile, year of manufacture, engine model, and transmission model corresponding to the stoichiometric air/fuel ratio ($O_2$) sensor to be measured through the measurement mode/condition setting means. This reduces the time required for searching for the appropriate conditions and operating errors and misunderstandings.

The measurement mode/condition setting means is also preferably constructed to make it possible to measure characteristics under any desired conditions, in case it is found necessary to measure and analyze characteristics under conditions that differ completely or partially from the optimum engine conditions (engine speed, intake pressure, torque, engine power, etc), exhaust flow velocity, exhaust temperature, exhaust composition, air/fuel ratio control period, and sensor temperature that are automatically selected by inputting the type of automobile, year of manufacture, engine model, transmission model and type of exhaust regulations corresponding to the stoichiometric air/fuel ratio ($O_2$) sensor to be measured.

This makes it possible to modify the selection that appears as the first option on the menu, if necessary, so that a characteristic can be measured under actual conditions that occur in a certain engine exhaust pipe, for example, or provide a deeper analysis of the $O_2$ sensor to be measured by measuring its characteristics under any desired conditions.

The temperature control means is preferably constructed to comprise an overall temperature control means, a component temperature display means, a thermoregulator control means, a sensor-heating power source means, and communications (high-speed signal transfer) means for the measurement control means.

In this case, the overall temperature control means controls the temperatures of all the components.

The component temperature display means displays the temperature of each component.

The thermoregulator control means transmits the setting temperature of each thermoregulator and receives control results.

The sensor-heating power source means transmits the setting voltage of the power source that heats the $O_2$ sensor to be measured, and receives a current value.

The communications means for the measurement control means receives a setting temperature from the measurement control means and transmits control results.

Highly accurate control at high speeds is enabled by dividing the temperature control means by function in this manner.

The air ratio (air/fuel-ratio) control means is preferably constructed to comprise an air ratio (air/fuel ratio) and flow rate control means, a component waveform display means, a control waveform generation means, and a communications (high-speed signal transfer) means for the measurement control means.

The air ratio (air/fuel ratio) and flow rate control means calculates the air ratio (air/fuel ratio) on the basis of the output (electromotive force or resistance) signal of the $O_2$ sensor to be measured and control constants. It obtains concentrations of each of the components of the air ratio (air/fuel ratio) from a previously input table. It also calculates the flow rates of these components from the concentrations of these components and the total gas flow.

The component waveform display means displays the air ratio (air/fuel ratio) waveform, waveforms of the concentrations of the components, and the output (electromotive force or resistance) waveform of the $O_2$ sensor to be measured on a CRT display.

Characteristics may also be measured from a fixed air ratio (air/fuel ratio) waveform, without any feedback control based on the output (electromotive force or resistance) signal of the $O_2$ sensor to be measured and the control constants. In such a case, the control waveform generation means is used to generate a fixed air ratio (air/fuel ratio) waveform.

The communications (high-speed signal transfer) means for the measurement control means receives the type of characteristic to be measured and the control constants from the measurement control means. It sends the value of the air ratio (air/fuel ratio) to the measurement control means.

Highly accurate control at high speeds is enabled by dividing the air ratio (air/fuel ratio) control means by function in this manner.

The air/fuel ratio and flow rate control means is preferably constructed to comprise a rich/lean determination means, a delay time addition means, a skip addition means, ramp rate addition means, a system delay compensation means, a gas component concentration computation means, and a gas component flow rate computation means.

The rich/lean determination means compares the output (electromotive force or resistance) signal of the $O_2$ sensor to be measured and a reference value, and determines rich or lean therefrom.

The delay time addition means adds a previously determined delay time to a signal that determines rich/lean.

The skip addition means adds a previously determined skip in compensation to the current value of the air ratio (air/fuel ratio), on the basis of the signal to which is added the delay time.

The ramp rate addition means compensates the air ratio (air/fuel ratio) signal to which the skip has been added, by a previously determined ramp rate.

An actual engine has several inherent time delays, including delays in the fuel supply system, delays caused by adhesion and the flow of the liquid fuel on the intake manifold, and delays caused by pauses in the cylinders. This apparatus is provided with the system delay compensation means to ensure that it can reproduce the same delays as those of an actual engine.

The gas component concentration computation means obtains the concentrations of the components of the air ratio (air/fuel ratio) from a previously input table.

The gas component flow rate computation means calculates the flow rates of these components from their concentrations and the total gas flow.

With the above apparatus, the same air ratio (air/fuel ratio) control result as that of an actual engine is obtained by using an air ratio (air/fuel ratio) compensation method that is used by an actual engine.

In addition, the same air ratio (air/fuel ratio) control result as that of an actual engine is obtained by this apparatus by using the rich/lean determination conditions, delay time, skip, and ramp rate that are used by an actual engine.

Since this apparatus uses model gases to adjust a testing gas, without burning the gasoline that is used in an actual engine, it enables extremely stable characteristic measurements without any of the instability of an actual engine. Thus reproducibility is also extremely good.

The system delay compensation means is preferably constructed of a high-order delay calculation means.

This use of a high-order delay calculation means as the system delay compensation means makes it easy to accommodate the several time delays inherent in an actual engine, including delays in the fuel supply system, delays caused by adhesion and flows of the liquid fuel on the intake manifold, and delays caused by pauses in the cylinders, making this apparatus even more like an actual engine.

The system delay compensation means may be constructed of means for calculating fuel vaporization ratios, gas-flow time constants, and liquid-flow time constants.

Such a configuration makes it easy to accommodate all the delays caused by factors such as fuel vaporization ratios, gas-flow time constants, and liquid-flow time constants in an actual engine. In other words, this enables the use of parameters that facilitate links between the causes of delays in the various parts of an actual engine, making it easier to accommodate them, and thus making this apparatus even more like an actual engine.

The gas regulation means is preferably constructed to comprise a gas flow control means, a liquid flow control means, an atomization means, a heating means, and a mixing means.

The gas flow control means controls the flow rates of components that are gases at room temperature and low pressure (nitrogen ($N_2$), carbon monoxide (CO), hydrogen ($H_2$), ethylene ($C_2H_4$), propylene ($C_3H_6$), oxygen ($O_2$), and nitric oxide (NO)).

The liquid flow control means controls the flow rates of components that are liquids at room temperature and low pressure (water vapor ($H_2O$) and toluene ($C_7H_8$)).

The atomization means atomizes the components supplied from the liquid flow control means.

The heating means heats the gaseous components and atomized liquid components.

The mixing means mixes the gas components and atomized liquid components.

This configuration makes it possible to precisely meter and regulate any desired gas composition, by controlling each of the components individually by a gas flow control means for components that are gases at room temperature and low pressure, and a liquid flow control means for components that are liquid at room temperature and low pressure.

In addition, since the components that are liquid at room temperature and low pressure are atomized after they have been metered, the motoring accuracy is good and there are few pulsations in the flow rates thereof.

Furthermore, since metered and mixed gaseous components are mixed with atomized liquid components, there are no variations in the mixed gas and the mixed gas is uniform, thus increasing the reproducibility of the measured characteristic with smaller time-dependent variations.

It is preferable that an ultra-fast gas flow controller is used as the gas flow control means.

Since an exhaust emission measurement running pattern includes running of an actual engine under conditions of a high engine speed and a high intake pressure, air/fuel ratio control must be performed under these engine conditions and the apparatus must be able to faithfully reproduce a waveform of changes in gas composition during high-speed air/fuel ratio control with a reference frequency on the order of 2.5 Hz. In an actual engine, ramps and skips are used to provide air/fuel ratio control that has a nonsinusoidal waveform. Such a nonsinusoidal waveform contains many high-frequency components. To ensure that these high-frequency components are also included in the reproduction, a high-speed gas flow controller with an average frequency on the order of 25 Hz is necessary.

The present inventors used a gas flow controller to faithfully reproduce a gas flow waveform having many high-frequency components, at a reference frequency on the order of 2.5 Hz.

This made it possible to reproduce a waveform close to that of an actual engine, even for an electromotive force waveform of the $O_2$ sensor.

It is preferable that liquid flow control means is constructed as a liquid-transfer pump.

In other words, it is extremely difficult to uniformly mix a component that is liquid at room temperature into a high-temperature gas at a constant proportion. This is because a phase change from liquid to gas is necessary, pulsations are likely to occur in the amount of liquid undergoing this phase change, the liquid expands dramatically as its phase changes, a rise in pressure is likely to occur on the load side of a half-sealed space within the piping, and this load-side pressure rise can easily reduce the amount of liquid that is transferred. As a result, pulsations can easily occur in the amount of liquid transferred and thus it is extremely difficult to mix the components uniformly at constant proportions.

Use of a liquid-transfer pump that prevents the amount of liquid transferred from being reduced by a rise in the load-side pressure has the effect of suppressing pulsations in the amount of liquid transferred.

Therefore, using a liquid-transfer pump as the liquid flow control means makes it possible to minimize pulsations in the amount of liquid transferred. As a result, components which are liquid at room temperature can be mixed into the high-temperature gas at constant proportions.

The liquid flow control means could be constructed as a liquid-transfer pump having a flow rate control function.

A method that causes variations in the amount of vaporization could be considered for varying the concentrations of components which are liquid at room temperature, but this is likely to make the size of the apparatus extremely large, and thermal inertia is also likely to be large, making it difficult to vary the amount of vaporization rapidly. On the other hand, a method that causes variations in the liquid flow would result in rapid variations because inertia would be small, and implementation would also be convenient. In such a case, the amount supplied can be varied rapidly by using a liquid-transfer pump having a flow rate control function to vary the liquid flow.

The liquid flow control means may be constructed of a liquid-transfer pump having a flow rate instruction signal communications function and a flow rate control function.

Configuring the liquid flow means which varies the concentration of components that are liquid at room temperature as a liquid-transfer pump having a flow rate instruction signal communications function and a flow rate control function makes it possible to provide automatic control from a controller such as a personal computer. This solves the problems raised by manual control, such as the impossibility of high-speed control because of the time taken by the operation and the likelihood that human errors will occur.

In addition, it is preferable to use an ultrasonic atomizer as this atomization means.

As stated previously, an extremely difficult problem concerns the method used to uniformly mix components which are liquid at room temperature into a high-temperature gas at constant proportions. Two methods could be used: one by which the components in liquid form are vaporized then are mixed with the other components that are gaseous, and one by which the components in liquid form are mixed with the other components and are then vaporized.

With the former method, the size of the apparatus is likely to become extremely large, and thermal inertia is also likely to be large, making it difficult to vary the amount of vaporization rapidly.

On the other hand, the latter method does not involve these problems, but it presents another subject of concern in that time-dependent variations (pulsations) in the amount of vaporization of liquid components must be minimized.

To minimize time-dependent variations (pulsations) in the amount of vaporization of liquid components, it is necessary to minimize time-dependent variations (pulsations) in the contact area between the heater and the liquid components.

Research conducted by the present inventors has determined that an effective method of minimizing time-dependent variations (pulsations) in the contact area between the heater and the liquid components is to atomize the liquid components and mix them with the gas, and vaporize them at the instant they come into contact with the heater.

This research has also determined that the use of an ultrasonic atomizer is more effective than a venturi tube apparatus in atomizing the liquid components.

Therefore, fine droplets of a small diameter can be formed from liquid components by using an ultrasonic atomizer to atomize them. As a result, time-dependent variations (pulsations) in the contact area between the heater and the liquid components can be minimized, and thus time-dependent variations (pulsations) in the amount of vaporization of liquid components can be minimized.

The atomization means may also be constructed to comprise an ultrasonic atomizer and a means of supplying a carrier gas at a controlled flow rate.

In other words, since the atomization means (ultrasonic atomizer) does not have a high thermal resistance, it is necessary to locate it a small distance away from the heating means (heater), to ensure that the heat from the heater does not cause damage.

That means it is necessary to convey the components that have been atomized by the atomization means (ultrasonic atomizer) to the heater. During this transfer process, the atomized liquid components will adhere to the walls of the pipeline and return to liquid form, which would destroy the effects of the atomization.

This raises the problem that the atomized liquid must be prevented from adhering to the pipeline walls.

To this end, the research of the present inventors has determined that it is effective to convey the atomized liquid by a carrier gas.

Thus, configuring the atomization means as described above and conveying the atomized liquid by a carrier gas can prevent the adhesion of atomized liquid to the pipeline walls. This makes it possible to prevent the return to liquid form of droplets adhering to the pipeline walls, and, as a result, makes it possible to minimize time-dependent variations (pulsations) in the amount of vaporization of liquid components.

It is preferable that $N_2$ is used as the carrier gas supplied to the atomization means. That is to say, although it would be convenient to use air as the carrier gas for preventing adhesion of the finely atomized liquid components to the pipeline walls, the addition of oxygen could have a large effect on the gas composition. In contrast, if nitrogen ($N_2$) is used as the carrier gas, no oxygen is added so the carrier gas will simply have the effect of diluting the other gases and would thus not affect the gas composition greatly.

It is also preferable that part of the $N_2$ that was previously metered by the gas flow control means is separated off to form the carrier gas supplied to the atomization means, gas flow control means.

In other words, if a new supply of $N_2$ were added, even though the carrier gas supplied to the atomization means is $N_2$, it would have the effect of further diluting the other components that are gaseous. In this case, part of the previously metered $N_2$ is separated off by the gas flow control means for use as the carrier gas supplied to the atomization means. Since this ensures that no new $N_2$ gas is added, the effect of further diluting the other components that are gaseous does not occur, which enables highly accurate concentration control and hence precise characteristic measurement.

The heater could also be constructed of two heaters connected in series.

As stated previously, an extremely difficult problem concerns the method used to uniformly mix components which are liquid at room temperature into a high-temperature gas at constant proportions. This problem becomes particularly complicated when the mixing concentrations are high.

Water vapor ($H_2O$) is included in the exhaust gases as a high concentration of approximately 15%. Water vapor ($H_2O$) has the effect of suppressing the above described reaction of hydrogen ($H_2$) in the vicinity of the electrodes of the $O_2$ sensor. Therefore, in order to reproduce the characteristic of an $O_2$ sensor of an actual engine on this apparatus, it is necessary to reproduce the same high concentration of water vapor ($H_2O$) as that in an actual engine.

If atomized water droplets are added to the other gases before they enter the heater, in order to create a high concentration of water vapor, the heater will be cooled thereby and the water will return to liquid form on the surfaces of the heater, thus destroying the effect of the atomization.

However, if the atomized water droplets are added to the other gases after they have passed through the heater, in order to create a high concentration of water vapor, the problem of recondensation on the surfaces of the heater would be solved, but a different problem will arise. In other words, the phase change from water to water vapor ($H_2O$) absorbs a large amount of latent heat of vaporization. All of the gases are cooled by this latent heat of vaporization, so that the required temperature is not achieved.

If the temperature of the heater is increased to compensate for the amount by which the gases are cooled by the latent heat of vaporization, it will approach the permissible limiting temperature of the heater, which would have an adverse effect on the lifetime of the heater.

To counter this problem, research performed by the inventors has shown that it is effective to configure the heating means of two serially connected heaters, with the atomized water droplets being mixed into the Other gases at an intermediate point therebetween.

Since the atomized water droplets are mixed in at a point at which the gases have been partially heated by the first-stage heater, there is no occurrence of the destruction of the effects of atomization that happen when the heater is cooled and the water is returned to liquid form on the surfaces of the heater.

Since the gases that have been cooled by the latent heat of vaporization are heated by the second-stage heater, a gas of the predetermined temperature is obtained.

In addition, since the second-stage heater is capable of compensating for the portion cooled by the latent heat of vaporization, the power required is reduced and the amount by which the surface temperature of the heater becomes higher than the objective gas temperature is insignificant, so that the lifetime thereof is extended without effort.

As mentioned previously, a first branch pipeline preferably branches out either horizontally or at an angle of up to 30° from the horizontal from partway along the main pipeline connecting the two serially connected heater sections.

That is to say, a gas that has been heated by the first-stage heater section heater flows partway along the main pipeline linking the two serially connected heaters, and the temperature thereof could rise to a high level. As mentioned previously, because there is some danger that the problem of thermal damage will arise, an ultrasonic atomizer cannot be located in such high-temperature sections.

Research performed by the inventors has shown that the problem of thermal damage can be solved by branching this first branch pipeline either horizontally or at an angle of up to 30° from the horizontal from partway along this main pipeline, and placing the ultrasonic atomizer in the first branch pipeline.

In other words, an appropriate location for the ultrasonic atomizer is in the first branch pipeline where thermal damage is small, rather than partway along the main pipeline. In particular, branching off the first branch pipeline either horizontally or at an angle of up to 30° from the horizontal ensures that, although some of the atomized water droplets supplied from the ultrasonic atomizer located in the first branch pipeline will adhere to the pipeline walls and return to liquid form, the slope of the branch pipeline and the action of gravity ensures that they can reach the main pipeline. Therefore the occurrence of errors in the gas composition can be prevented.

A partition is provided within the first branch pipeline to divide it vertically. This partition is constructed to extend along the approximate center of the main pipeline to block off between 20% and 100% of the cross-sectional area of the main pipe. The configuration is such that all or part of the gas that has been heated by the first heater section and is flowing through the main pipeline is guided below the partition in the first branch pipeline, passes through the portion at the end section of the first branch pipeline where the partition is not provided, and is guided over the partition to return to the main pipe. The configuration could be such that an opening portion is provided in the upper surface of the first branch pipeline.

That is to say, a partition is provided within the first branch pipeline to divide it vertically, this partition extends along the approximate center of the main pipeline, and thus between 20% and 100% of the cross-sectional area of the main pipe is blocked off. A portion with no partition is provided at an end section of the branch pipeline (not at the joint with the main pipeline), connecting together the areas above and below the partition. An opening portion is provided in the upper surface of the first branch pipeline.

The gas that has been heated by the first heater and is flowing in the main pipeline reaches the partition section. All or part of the gas, depending on how far the partition extends over the main pipeline, is guided below the partition in the first branch pipeline. The gas passes through the end section of the first branch pipeline where here is no partition, is guided to above the partition, and then returns to the main pipeline. Tiny droplets of water formed by the ultrasonic atomizer are supplied from the opening portion provided in the upper surface of the first branch pipeline.

The above configuration provides the actions and effects discussed below. When atomized water droplets are mixed into a gas, uniform mixing is necessary, but this causes some problems. One problem concerns the way in which the mixing-in of tiny droplets within the pipeline in which gas is flowing increases the concentration at the opening portion side.

This apparatus can uniformly mix atomized water droplets into the gas by the action of gravity, by supplying water droplets atomized by the ultrasonic atomizer from the opening portion provided in the upper surface of the first branch pipeline.

This solves the problem of uneven distribution of atomized water droplets within the gas, enabling precise characteristic measurement.

The configuration could be such that a second branch pipeline having an opening portion at an end section thereof is provided either vertically or at an angle of up to 30° from the vertical, from an opening portion provided in the upper surface of this first branch pipeline.

In contrast with the high-temperature gas flowing in the first branch pipeline, no high-temperature gas flows through the second branch pipeline that branches off from an opening portion provided in the upper surface of the first branch pipeline, so that it is not heated thereby.

Since the second branch pipeline is not heated as the first branch pipeline is, the danger of thermal damage to the ultrasonic atomizer can be made insignificant by placing the ultrasonic atomizer in the second branch pipeline.

The second branch pipeline is orientated either vertically or at an angle of at an angle of up to 30° from the vertical form an opening portion provided in an upper surface of the first branch pipeline. Atomized water droplets supplied from the ultrasonic atomizer placed in this end section pass through the second branch pipeline and are supplied into the gas from the opening portion in the first branch pipeline. In this case, the atomized water droplets are encouraged to flow within the pipeline by the action of gravity. Therefore, the adhesion of atomized water droplets to the pipeline walls is reduced.

A downward flow of gas, in other words a gas curtain, may be provided along the wall surfaces within the second branch pipeline.

This provision of a downward flow of gas, in other words a gas curtain, along the wall surfaces within the second branch pipeline makes it difficult for water droplets that have been atomized and scattered by the ultrasonic atomizer to adhere to the pipeline walls, so that the amount of tiny droplets that return to liquid form on the pipeline walls is reduced.

The configuration may also be such that the gas consisting of atomized water mixed with the carrier gas is supplied midway between the two serially connected heaters.

The configuration may also be such that the gas consisting of atomized water mixed with the carrier gas is supplied to an upper surface of the partition, from an opening portion formed in the upper surface of the first branch pipeline.

The configuration may also be such that the gas consisting of atomized water mixed with the carrier gas is supplied to an upper surface of the partition, from an opening portion formed in the end surface of the second branch pipeline.

In addition, the gas piping systems in which each of the atomized carbon monoxide (CO), hydrogen ($H_2$), ethylene ($C_2H_4$), propylene ($C_3H_6$), oxygen ($O_2$), nitric oxide (NO), and toluene ($C_7H_8$), which are supplied at controlled flow rates, is mixed with the carrier gas may be constructed to be connected independently to the main pipeline behind the two serially connected heaters.

The configuration may also be such that the piping in which the combustible gases (carbon monoxide (CO), hydrogen ($H_2$), ethylene ($C_2H_4$), and propylene ($C_3H_6$)) are combined at controlled flow rates, the piping which the combustion-supporting gases (oxygen ($O_2$) and nitric oxide (NO)) are combined at controlled flow rates, and the piping in which the atomized toluene ($C_7H_8$) is mixed with the carrier gas are each connected independently to a rear portion of the two serially connected heater sections.

The configuration may be such that an absolute pressure measurement means is provided in the main pipeline at each joint section where one of the gases joins the main pipeline, and a portion of the gas of a flow rate measured within the flow rate controller is used to compensate for the pressure-dependent flow rate measurement error.

This configuration, in which an absolute pressure measurement means is provided in the main pipeline at each gas joint section, and the pressure thereof is set to a preset constant value, may be used in a configuration in which means for automatically adjusting the degree of opening of a throttle valve provided at the end of the flow path is provided, to ensure that the pressure achieves a preset constant value.

The configuration may be further modified by the provision of a static type of in-pipe mixer in a rear portion of the joint section for each gas in the main pipeline, to encourage the mixing of gases.

The form of the sensor attachment means may be a circular cylindrical holder with one end closed and gas inlet and outlet pipes provided in opposite side surfaces thereof, with a cartridge heater being embedded in the circular cylindrical holder to heat the holder.

An alternative configuration of the sensor attachment means may be a circular cylindrical holder of an inner diameter that is twice the outer diameter of a protective cover of the stoichiometric air/fuel ratio ($O_2$) sensor to be measured, with one end closed, and with gas inlet and outlet pipes provided in opposite side surfaces thereof. The shape of these gas inlet and outlet pipes is rectangular, the internal width of this rectangle has the same dimension as the outer diameter of the protective cover of the stoichiometric air/fuel ratio ($O_2$) sensor to be measured, the internal height of this rectangle has the same dimension as the entire width over which small holes are provided in the outer protective cover of the stoichiometric air/fuel ratio ($O_2$) sensor to be measured, and the positions at which the gas inlet and outlet pipes are attached correspond to positions at which small holes are provided in the outer protective cover of the stoichiometric air/fuel ratio ($O_2$) sensor to be measured.

Another alternative configuration of the sensor attachment means may be a circular cylindrical holder of an inner diameter that is at least twice the outer diameter of the protective cover of the stoichiometric air/fuel ratio ($O_2$) sensor to be measured, with one end closed, with gas inlet and outlet pipes provided in opposite side surfaces thereof, and a core that is inserted into the circular cylindrical holder with one sealed end in such a manner that it is in internal contact therewith. Rectangular gas inlet and outlet apertures are opened in two side surfaces of the core, the shape of gas inlet and outlet pipes thereof is rectangular or circular cylindrical, the inner dimensions of this rectangular or circular cylindrical shape are bigger than the dimensions of the above described rectangular gas inlet and outlet pipes provided in the two side surfaces of the circular cylindrical holder, and the positions at which the gas inlet and outlet pipes are attached and the positions of the rectangular gas inlet and outlet apertures provided in the two side surfaces of the core correspond to positions at which small holes are provided in the outer protective cover of the stoichiometric air/fuel ratio ($O_2$) sensor to be measured.

The configuration may be such that the internal width of the rectangular gas inlet and outlet apertures provided in the two side surfaces of the core has a dimension that the same as the outer diameter of the protective cover of the stoichiometric air/fuel ratio ($O_2$) sensor to be measured, the internal height of this rectangle has the same dimension as the entire width over which small holes are provided in the outer protective cover of the stoichiometric air/fuel ratio ($O_2$) sensor to be measured, and a space between the inner dimension of the core and the outer diameter of the protective cover of the stoichiometric air/fuel ratio ($O_2$) sensor to be measured is half the internal width of the gas inlet and outlet apertures.

The configuration may also be such that the internal width of the rectangular gas inlet and outlet apertures provided in the two side surfaces of the core has a dimension that is $2/3 \pm 10\%$ times the outer diameter of the protective cover of the stoichiometric air/fuel ratio ($O_2$) sensor to be measured, the internal height of this rectangle has the same dimension as the entire width over which small holes are provided in the outer protective cover of the stoichiometric air/fuel ratio ($O_2$) sensor to be measured, and the space between the inner dimension of the core and the outer diameter of the protective cover of the stoichiometric air/fuel ratio ($O_2$) sensor to be measured is half the internal width of the gas inlet and outlet apertures.

The configuration may also be such that the internal width of the rectangular gas inlet and outlet apertures provided in the two side surfaces of the core has a dimension that is $1/2 \pm 10\%$ times the outer diameter of the protective cover of the stoichiometric air/fuel ratio ($O_2$) sensor to be measured, the internal height of this rectangle has the same dimension as the entire width over which small holes are provided in the outer protective cover of the stoichiometric air/fuel ratio ($O_2$) sensor to be measured, and the space between the inner dimension of the core and the outer diameter of the protective cover of the stoichiometric air/fuel ratio ($O_2$) sensor to be measured is half the internal width of the gas inlet and outlet apertures.

The shape of the attachment means for the air/fuel ratio detection sensor in the air/fuel ratio waveform measurement means is preferably the same as the shape of the attachment means of the stoichiometric air/fuel ratio ($O_2$) sensor to be measured.

The sensor attachment means may also comprise:

a first sensor attachment means in which a first air/fuel ratio sensor to be measured is mounted and to which is supplied a gas from the gas regulation means, a three-way catalyst section provided downstream from the first sensor attachment means, a second sensor attachment means provided downstream from the three-way catalyst section, in which a second air/fuel ratio sensor to be measured is mounted; wherein:

the control means is constructed to control the gas regulation means on the basis of outputs from the first and second air/fuel ratio sensors to be measured.

In other words, air/fuel ratio control provided by an actual engine is based on a detection output obtained by using an air/fuel ratio sensor in a configuration such as that shown in FIG. 1 to directly detect exhaust gases supplied from the engine, and on detection outputs obtained by using air/fuel ratio sensors provided on both the upstream and downstream sides of a three-way catalyst in a configuration such as that shown in FIG. 10.

Therefore, the above described sensor attachment means and control means could also be used for the latter type of characteristic analysis of an air/fuel ratio sensor that models an actual engine.

In this case, an attachment means of the three-way catalyst preferably has a configuration such that it is provided with a heater so that it can be heated to the same temperature as the air/fuel ratio ($O_2$) sensor to be measured.

The three-way catalyst attachment means may be constructed in such a manner that a number of narrow-diameter, short, monolithic pieces of catalyst are arrayed in series, the space velocity of the system can be adjusted simply according to the number of pieces of catalyst used, and means is provided for preventing the flow of gases in portions where the catalyst is not used.

The three-way catalyst attachment means may also have a configuration in which a plurality of stages of narrow-diameter, short, monolithic layers of catalyst are stacked, and the space velocity of the system can be adjusted simply by varying the number of catalyst layers in the stack.

The attachment means of the stoichiometric air/fuel ratio ($O_2$) sensor downstream from the catalyst may be constructed to have the same shape and dimensions as the attachment means of the stoichiometric air/fuel ratio ($O_2$) sensor upstream from the catalyst.

The configuration may also be such that control constants of the stoichiometric air/fuel ratio ($O_2$) sensor upstream of the catalyst are manipulated by a signal obtained by processing an output (electromotive force or resistance) of the stoichiometric air/fuel ratio ($O_2$) sensor downstream from the catalyst, to adjust the average value and control waveform of air/fuel ratio control.

A means for processing an output (electromotive force or resistance) of the stoichiometric air/fuel ratio ($O_2$) sensor downstream from the catalyst may be constructed to comprise a rich/lean determination means downstream from the catalyst that is independent of the output (electromotive force or resistance) processing means of the stoichiometric air/fuel ratio ($O_2$) sensor downstream from the catalyst, delay time addition means for downstream from the catalyst, skip addition means for downstream from the catalyst, and ramp rate addition means for downstream from the catalyst.

The configuration may include a skip that is a control constant for the stoichiometric air/fuel ratio ($O_2$) sensor upstream from the catalyst, manipulated by a signal obtained by processing an output (electromotive force or resistance) of the stoichiometric air/fuel ratio ($O_2$) sensor downstream from the catalyst.

The configuration may also provide two parallel piping systems for the sensor attachment means in which are mounted the stoichiometric air/fuel ratio ($O_2$) sensors to be measured, with branch flow control means provided downstream from each system, wherein automatic control of a branch flow rate in each piping system is provided on the basis of branch flow rate instruction signals.

The branch flow control means may be constructed to comprise a gas temperature adjustment means and a gas flow measurement means.

The gas temperature adjustment means may be constructed to comprise a heat exchanger, a cooling water adjustment valve, and a thermoregulator for driving the cooling water adjustment valve.

The configuration may also comprise a throttle valve and an adjustor for driving the throttle valve.

The gas flow measurement means may be constructed to comprise a laminar flow element, a differential pressure sensor, and a differential pressure amplifier or display device.

The configuration may be such that a sensor is provided for measuring absolute pressure in the attachment holder of the stoichiometric air/fuel ratio ($O_2$) sensor to be measured, and this absolute pressure is used to issue branch flow instructions and provide automatic control, regardless of changes in the pressure (atmospheric pressure) at the exhaust aperture.

The configuration may also be such that two parallel piping systems are provided, each comprising a sensor attachment means in which is mounted a stoichiometric air/fuel ratio ($O_2$) sensor to be measured, a three-way catalyst attachment section, and a stoichiometric air/fuel ratio ($O_2$) sensor attachment means for downstream from the catalyst, connected in series, with branch flow control means provided downstream from each system, wherein automatic control of a branch flow rate in each piping system is provided on the basis of branch flow rate instruction signals.

The air/fuel ratio measurement means (precision air ratio meter) may also be constructed to have an automatic measurement function, a self-diagnosis function, and/or an automatic inspection function.

The air/fuel ratio measurement means (precision air ratio meter) may also be constructed to have a function for communicating with the control means.

The air/fuel ratio waveform measurement means (high-speed air/fuel ratio meter) may also be constructed to use a limiting-current type of air/fuel ratio sensor to measure air/fuel ratios.

As discussed above, the present invention has the effect of enabling an apparatus for analyzing air/fuel ratio sensor characteristics that can measure the characteristics of an air/fuel ratio sensor to an extremely high level of accuracy.

BRIEF DESCRIPTION OF THE DRAWINGS

FIGS. 2A and 2B are a block diagram of a specific configuration of the measurement control section used in the embodiments;

FIG. 8 is a graph illustrating the air ratio waveform after system delay compensation in accordance with the embodiments;

FIGS. 9A and 9B are a block diagram of the gas regulation section of the embodiments;

FIG. 21 is graphs illustrating measurement data obtained for $O_2$ sensors;

FIG. 23 is graphs illustrating measurement data obtained for $O_2$ sensors.

PREFERRED EMBODIMENTS OF THE INVENTION

Figure 1:
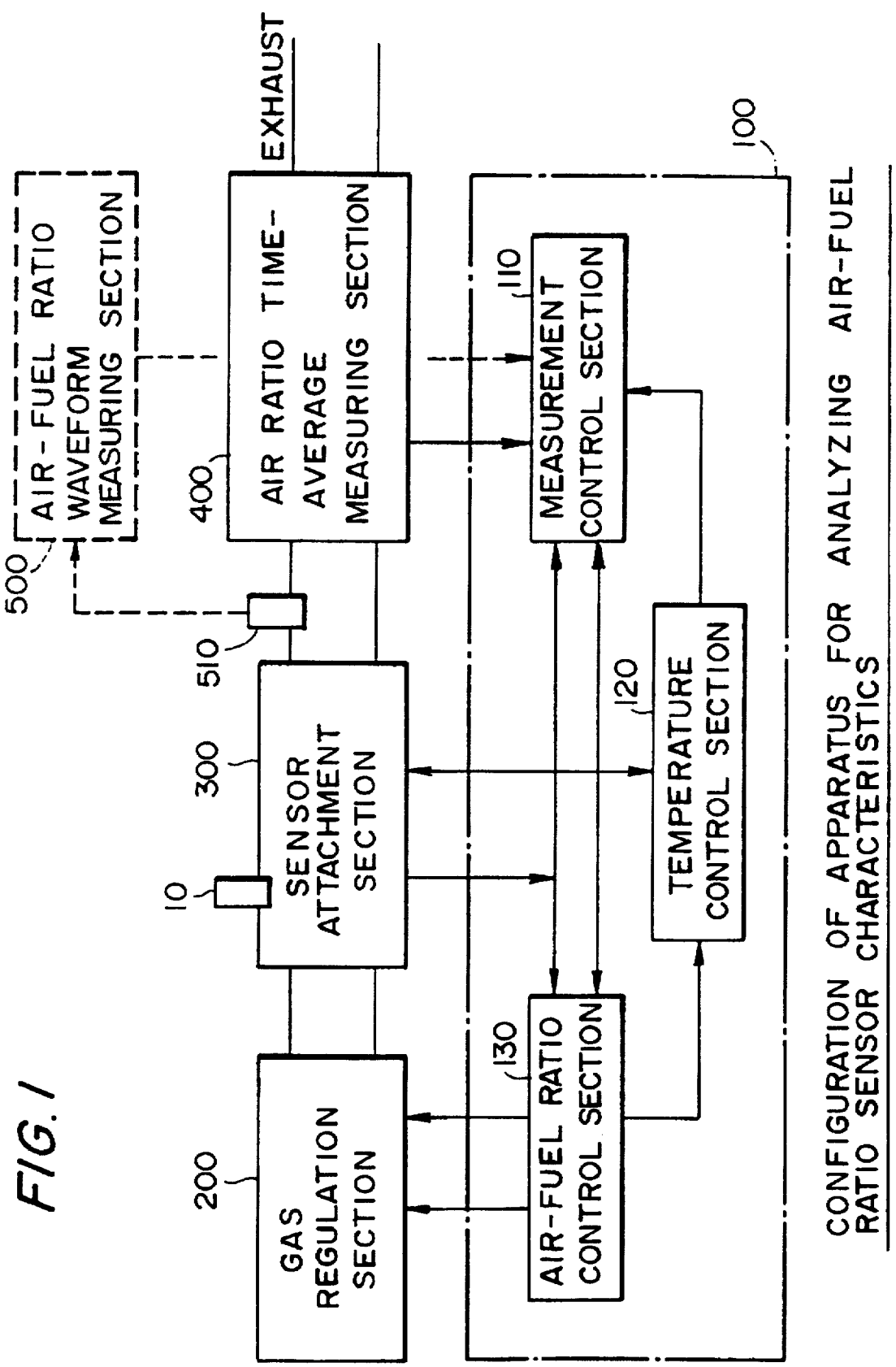
FIG. 1 is a block diagram of a preferred embodiment of an apparatus for analyzing air/fuel ratio sensor characteristics in accordance with the present invention.

Preferred embodiments of this invention are described below with reference to the accompanying drawings.
First Embodiment An apparatus for analyzing $O_2$ sensor characteristics in accordance with a first embodiment of this invention is shown in FIG. 1.

The apparatus for analyzing $O_2$ sensor characteristics of this embodiment is constructed to comprise a control section 100, a gas regulation section 200, a sensor attachment section 300, and an air ratio time-average measuring section 400 that acts as an air/fuel ratio measurement section.

A stoichiometric air/fuel ratio ($O_2$) sensor 10 to be tested is mounted in the sensor attachment section 300, and an output (electromotive force or resistance) signal from this sensor 10 is fed to the control section 100 for processing.

The control section 100 controls the gas regulation section 200 on the basis of this output (electromotive force or resistance) signal from the stoichiometric air/fuel ratio ($O_2$) sensor 10 to be measured, in order to achieve a stoichiometrical air/fuel ratio (the air ratio of $\lambda=1$).

The gas regulation section 200 operates under the control of the control section 100 to control the flow rates and heat various gas components, in order to send a model gas of a predetermined flow velocity, predetermined gas composition, and predetermined temperature to the sensor attachment section 300.

The air ratio time-average measuring section 400 is capable of measuring a deviation $\Delta\lambda'$ from $\lambda$, which represents the stoichiometric air/fuel ratio of the $O_2$ sensor 10, by measuring the time average of this air ratio.

Figure 20:
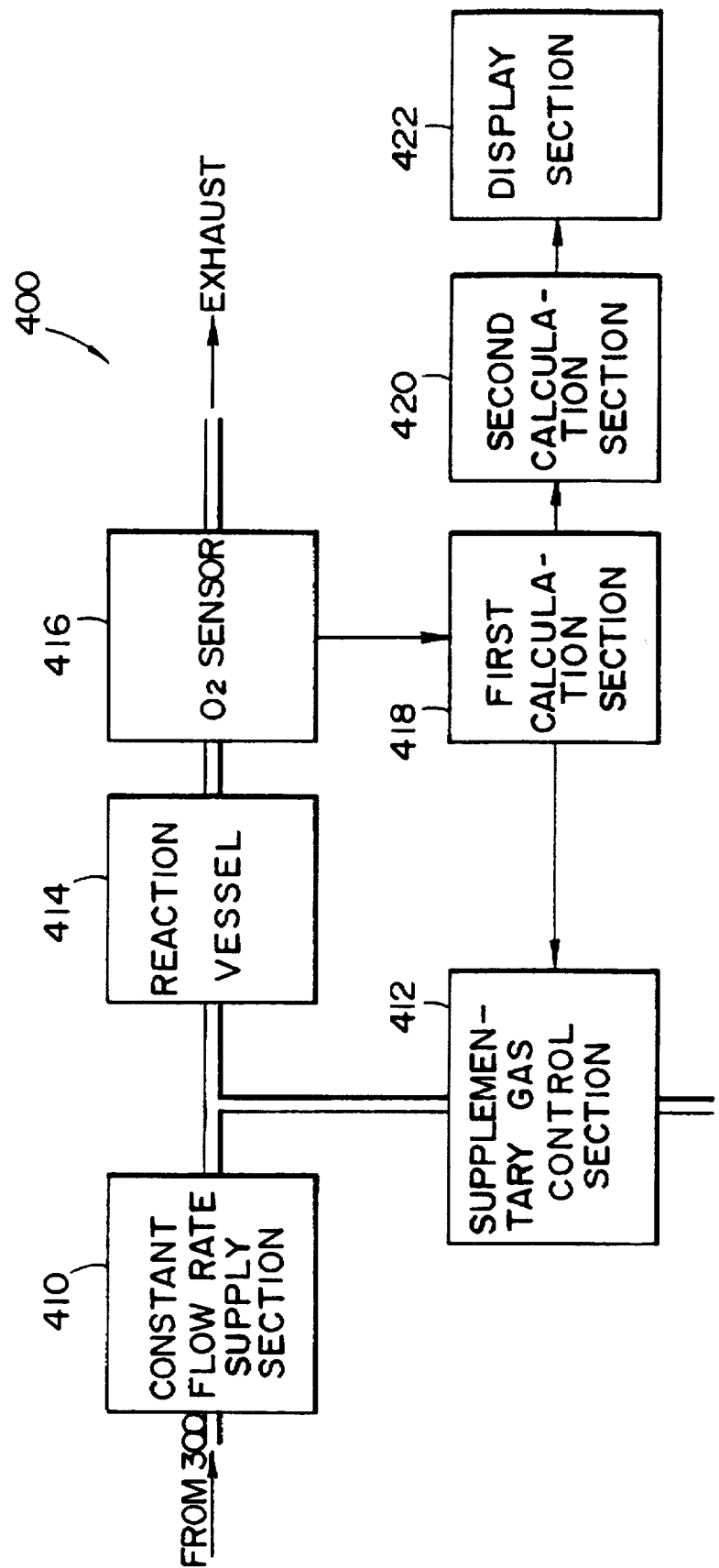
FIG. 20 is a block diagram of a more specific configuration of the measuring section.
Figure 22:
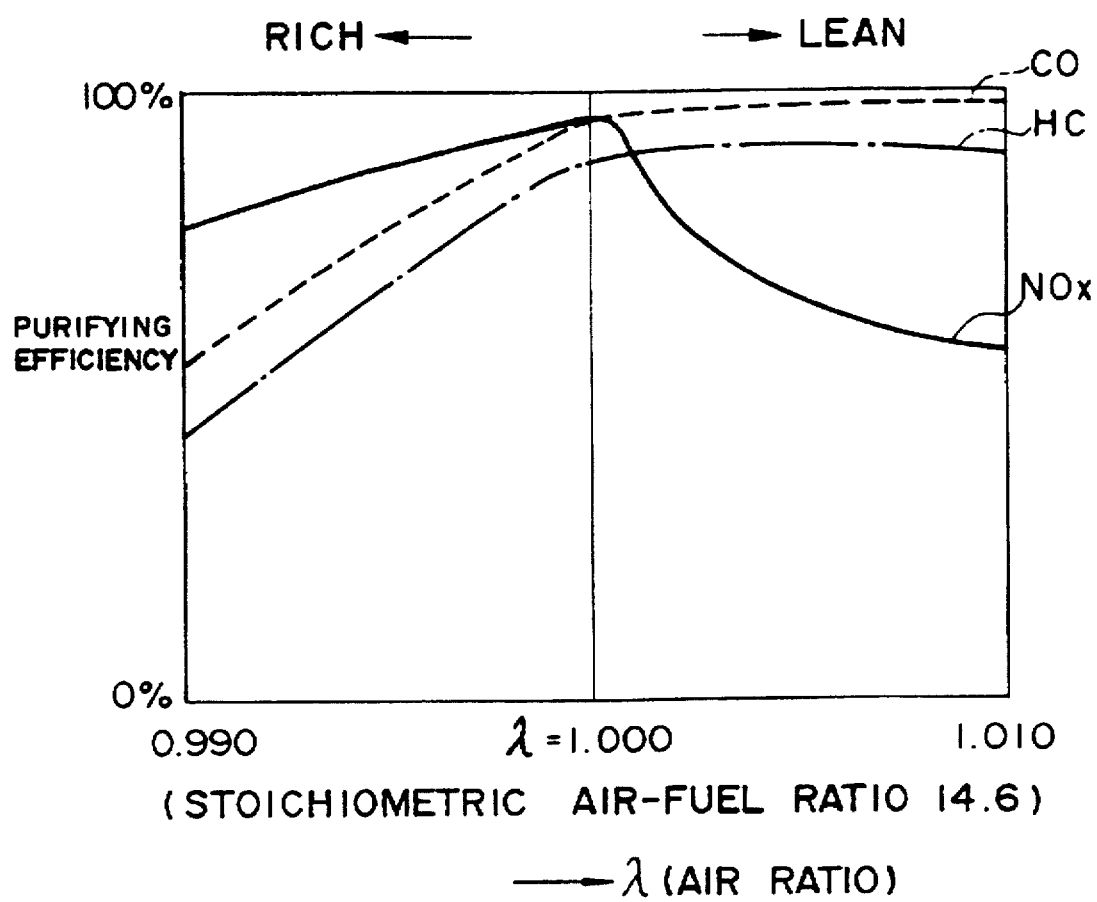
FIG. 22 is a graph illustrating the correlation between air/fuel ratio and purifying efficiency.

A specific example of the configuration of this air ratio time-average measuring section 400 is shown in FIG. 20.

The basic configuration of the air ratio time-average measuring section 400 of this embodiment is described below. If the air/fuel ratio of gas exhausted from the sensor attachment section 300 deviates from the stoichiometric air/fuel ratio, it can be assumed that either the fuel or oxygen supply is deficient. For that reason, if it could be determined which gas is deficient and by what proportion it is deficient, it would be possible to return the gas to its stoichiometric air/fuel ratio by adding this deficient portion. The air/fuel ratio of the gas being tested (the gas supplied from the gas regulation section 200) can be calculated and derived from the type and mixing ratio of the gas that is added in this manner.

Thus the measuring section 400 of this embodiment is constructed to comprise a fixed flow rate supply section 410 that separates off gas at a fixed flow rate from the gas exhausted from the sensor attachment section 300; a supplementary gas control section 412 that supplies the above supplementary gas; a reaction vessel 414 that agitates the separated gas and the supplementary gas and causes them to react, an $O_2$ sensor 416 for detecting in which direction the air/fuel ratio of the resultant gas mixture deviates from the stoichiometric air/fuel ratio; a first calculation section 418 that calculates the flow rate of gas to be supplemented in order to make the air/fuel ratio of the gas that was separated off from the fixed flow rate supply section 410 equal to the stoichiometric air/fuel ratio, on the basis of an output from this $O_2$ sensor, and outputs that flow rate as a control signal directed at the supplementary gas control section 412; a second calculation section 420 that calculates the air/fuel ratio of the gas supplied from the gas regulation section 200; and a display section 422 that displays the thus calculated air/fuel ratio.

In other words, the fixed flow rate supply section 410 sucks in a constant quantity of the gas exhausted from the sensor attachment section 300 and supplies it as the gas to be tested to the reaction vessel 414 onward.

The reaction vessel 414 is designed to cause the gas to be measured to be mixed thoroughly with the supplementary gas, and also encourage a reaction therebetween that brings the gas mixture to a state that is close to chemical equilibrium.

In this embodiment, either hydrogen or oxygen is supplied selectively from the supplementary gas control section 412 as the supplementary gas which reacts with the gas to be measured in the reaction vessel 414. The $O_2$ sensor 416 then detects whether the mixture of the gas to be measured plus the supplementary gas is rich or lean, and outputs a corresponding detection signal to the first calculation section 418.

The first calculation section 418 identifies whether the gas mixture is rich or lean from the output of the $O_2$ sensor 416, and determines the type and flow rate of the gas to be added.

In other words, the output of the $O_2$ sensor 416 identifies whether the gas mixture is rich or lean, depending on whether it is greater or less than a reference value. If result of this identification determines that the mixture is rich, the supplementary gas control section 412 is controlled thereby to gradually add oxygen (or air) until the stoichiometric air/fuel ratio is achieved. Alternatively, if the mixture is identified as being lean, hydrogen is gradually added until the stoichiometric air/fuel ratio is achieved. When the gas detected by the $O_2$ sensor 416 has reached a state close to the stoichiometric air/fuel ratio, because of this addition of oxygen or hydrogen, the second calculation section 420 calculate the air/fuel ratio and displays it on the display section 422.

Thus the measuring section 400 of this embodiment makes it possible to accurately measure the amount by which the gas deviates from $\lambda=1$, which represents the stoichiometric air/fuel ratio of the $O_2$ sensor 10 shown in FIG. 1.

The system of this embodiment also reproduces the same exhaust temperature, flow velocity, gas composition, and high-speed $\lambda$ change waveform as those under engine high-load conditions, as will be described later. To model the change in $\lambda$ at the engine intake systems such as an intake valves and intake manifold, the gas regulation section 200 could be constructed to insert parameters relating to fuel vaporization ratio and gas flow time constants, discover the optimum conditions, and cause the $O_2$ sensor to output an electromotive force waveform that is close to that in an actual engine.

The above configuration makes it possible to reproduce a measurement environment that is the same as that when the $O_2$ sensor 10 is mounted in an actual engine, and enables accurate analysis of the characteristics of the $O_2$ sensor 10 in that measurement environment, with an accuracy of 0.1%.

Figure 19:
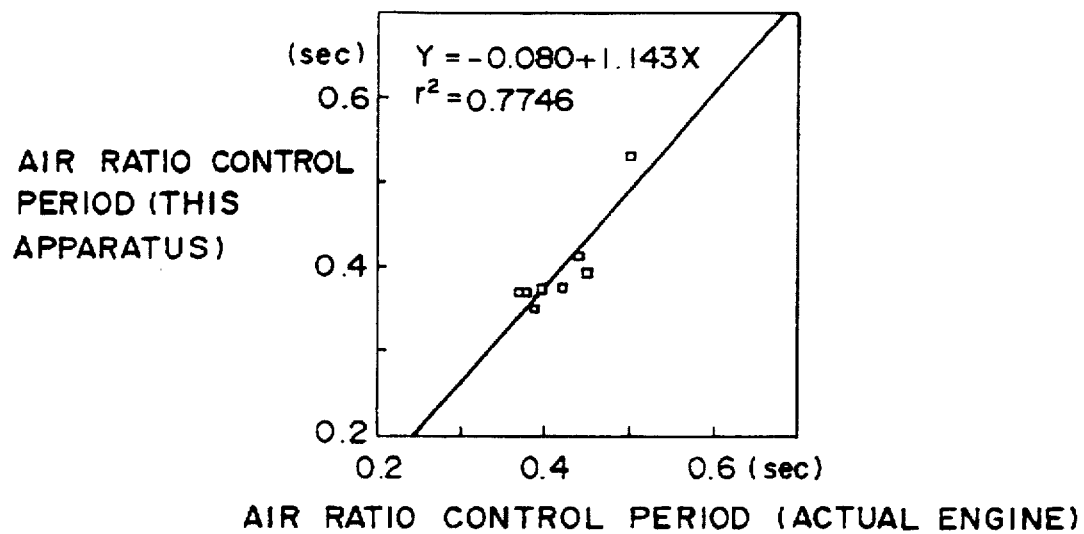
FIG. 19 is a graph of the correlation between control periods measured by the apparatus of this embodiment and an actual engine.

As will be described later, use of the apparatus of this embodiment makes it possible to obtain an air ratio control period having a good correlation coefficient ($r^2>0.75$) with respect to an actual engine, as shown in FIG. 19. Thus, use of the apparatus of this embodiment makes it possible to analyze the characteristics of the $O_2$ sensor 10 to an extremely high level of accuracy from this point of view.

The apparatus of this embodiment is preferably constructed to further comprise an air/fuel ratio waveform measuring section 500. This air/fuel ratio waveform measuring section 500 is constructed of an air/fuel ratio detection section 510 inserted into the exhaust pipe and a separate instrument which are often connected by cables. Note that this air/fuel ratio detection section 510 is mounted downstream of the sensor attachment section 300 in FIG. 1, but it may be mounted upstream thereof. The addition of this air/fuel ratio waveform measuring section (high-speed air/ fuel ratio meter) 500 makes it possible to measure not only a time average of the air ratio of the control led gas, based on a result of processing the output (electromotive force or resistance) signal of the stoichiometric air/fuel ratio ($O_2$) sensor 10 to be measured, but also the waveform of changes therein. It also enables a quantitative, detailed comparison with the waveform of changes in an actual engine, which has the effect of making this apparatus for analyzing $O_2$ sensor characteristics even more like an actual engine. The measured changes in the air ratio are transferred to the control section 100 for recording and charting/graphing data processing. Note that this air ratio is obtained by dividing the actual air/fuel ratio by the stoichiometric air/fuel ratio.

Second Embodiment

Figure 10:
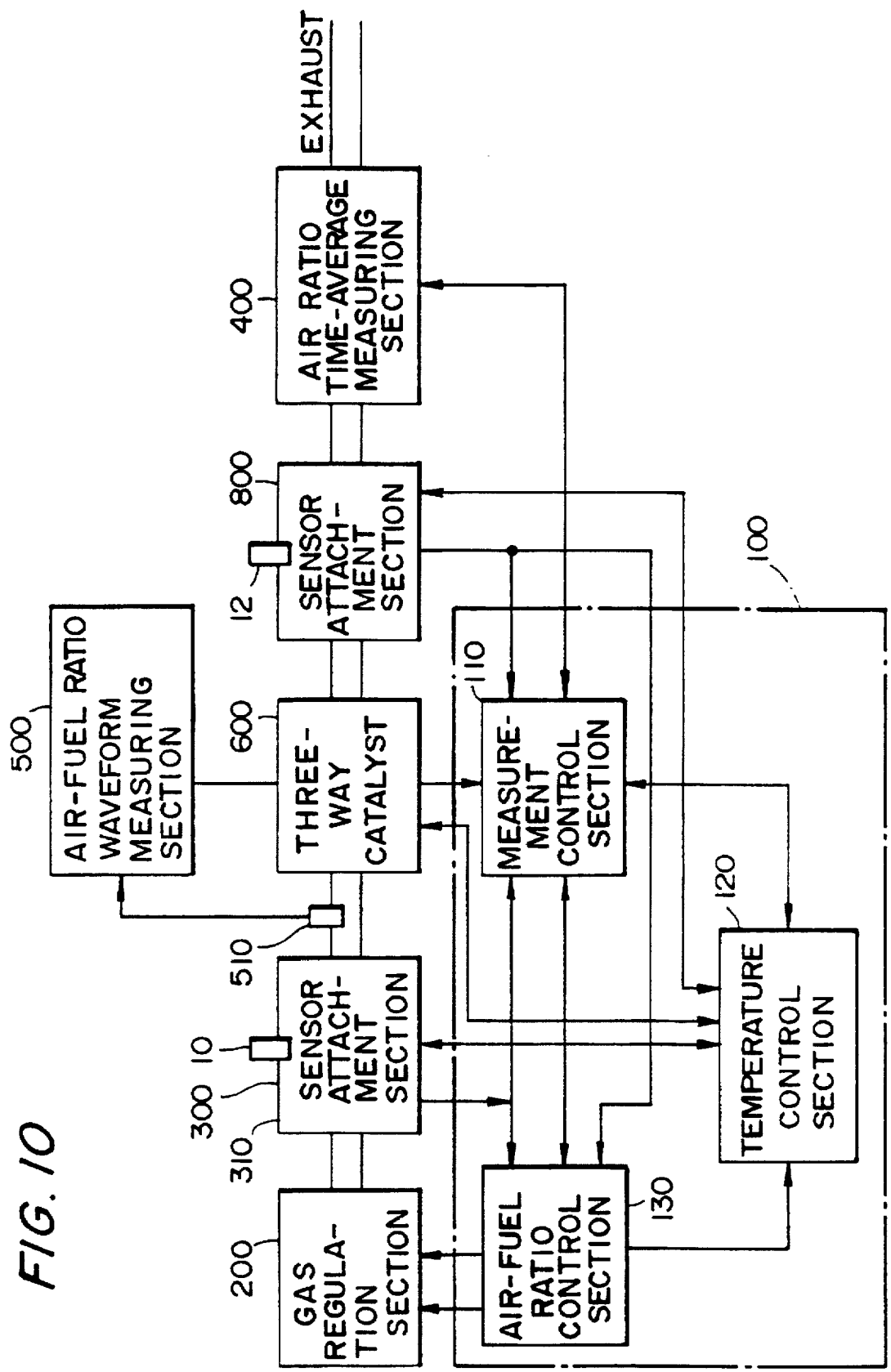
FIG. 10 is a block diagram of another preferred embodiment of an apparatus for analyzing air/fuel ratio sensor characteristics in accordance with the present invention.

An apparatus for analyzing $O_2$ sensor characteristics in accordance with a second embodiment of this invention is shown in FIG. 10.

In contrast with the first embodiment of the apparatus for analyzing $O_2$ sensor characteristics shown in FIG. 1, which supposes an engine system that controls the air/fuel ratio on the basis of a detection output of a single $O_2$ sensor 10, the second embodiment of this apparatus for analyzing $O_2$ sensor characteristics shown in FIG. 10 supposes an engine model that provides two $O_2$ sensors, on the upstream and downstream-sides of a three-way catalyst, and controls the air/fuel ratio on the basis of detection outputs from both of these $O_2$ sensors.

In other words, the apparatus for analyzing $O_2$ sensor characteristics in accordance with this embodiment is constructed to comprise the control section 100, the gas regulation section 200, two sensor attachment sections 300 and 800, a three-way catalyst 600, the air ratio time-average measuring section 400, and the air/fuel ratio waveform measuring section 500.

First and second air/fuel ratio ($O_2$) sensors 10 and 12 that are being tested are installed in the two sensor attachment sections 300 and 800.

The control section 100 is constructed to use a method similar to that of an actual engine to control the air/fuel ratio of the gas regulation section 200, on the basis of detection outputs of these first and second $O_2$ sensors 10 and 12.

This configuration makes it possible to supply a gas having the same components as exhaust gases that are emitted from this type of engine model to the air ratio time-average measuring section 400 from a second sensor attachment section 800. As a result, this measuring section 400 can obtain an air/fuel ratio of the exhaust gases in the same manner as in the first embodiment.

Note that this embodiment is constructed in such a manner that the operator can select and use either of the two apparatuses for analyzing $O_2$ sensor characteristics shown in FIGS. 1 and 10, by using the control section 100 to make the selection.

The description now turns to details of the various members of the apparatuses for analyzing $O_2$ sensor characteristics that were described above as first and second embodiments of this invention.

Specific Configurations

A. Configuration of Apparatus for Analyzing $O_2$ Sensor Characteristics

The control section 100 comprises a measurement control section 110, a temperature control section 120, and an air/fuel ratio control section 130.

In addition to issuing instructions to all the components of the apparatus for analyzing $O_2$ sensor characteristics, such as the air/fuel ratio control section 130, the temperature control section 120, and the air ratio time-average measuring section 400, the measurement control section 110 is responsible for measuring the output (electromotive force or resistance) waveform of the air/fuel ratio ($O_2$) sensor 10 to be measured and recording, graphing, and plotting the measurement results of the air ratio time-average measuring section 400 and the air/fuel ratio waveform measuring section 500.

In addition to controlling the temperatures of all parts of the apparatus for analyzing $O_2$ sensor characteristics, including the gas regulation section 200, the sensor attachment section 300, and the various lengths of piping, on the basis of instructions from the measurement control section 110, the temperature control section 120 is also responsible for posting details of the temperature control state to the measurement control section 110.

In addition to processing the output (electromotive force or resistance) of the stoichiometric air/fuel ratio ($O_2$) sensor to be measured that is mounted in the sensor attachment section 300 and calculating the air/fuel ratio to be controlled, on the basis of instructions from the measurement control section 110, the air/fuel ratio control section 130 is responsible for calculating the gas composition and gas flow corresponding to this air/fuel ratio, controlling the output of instructions to the gas regulation section 200, and also posting details of the air/fuel ratio control state to the measurement control section 110.

A-1 Measurement Control Section 110

Figure 2B:
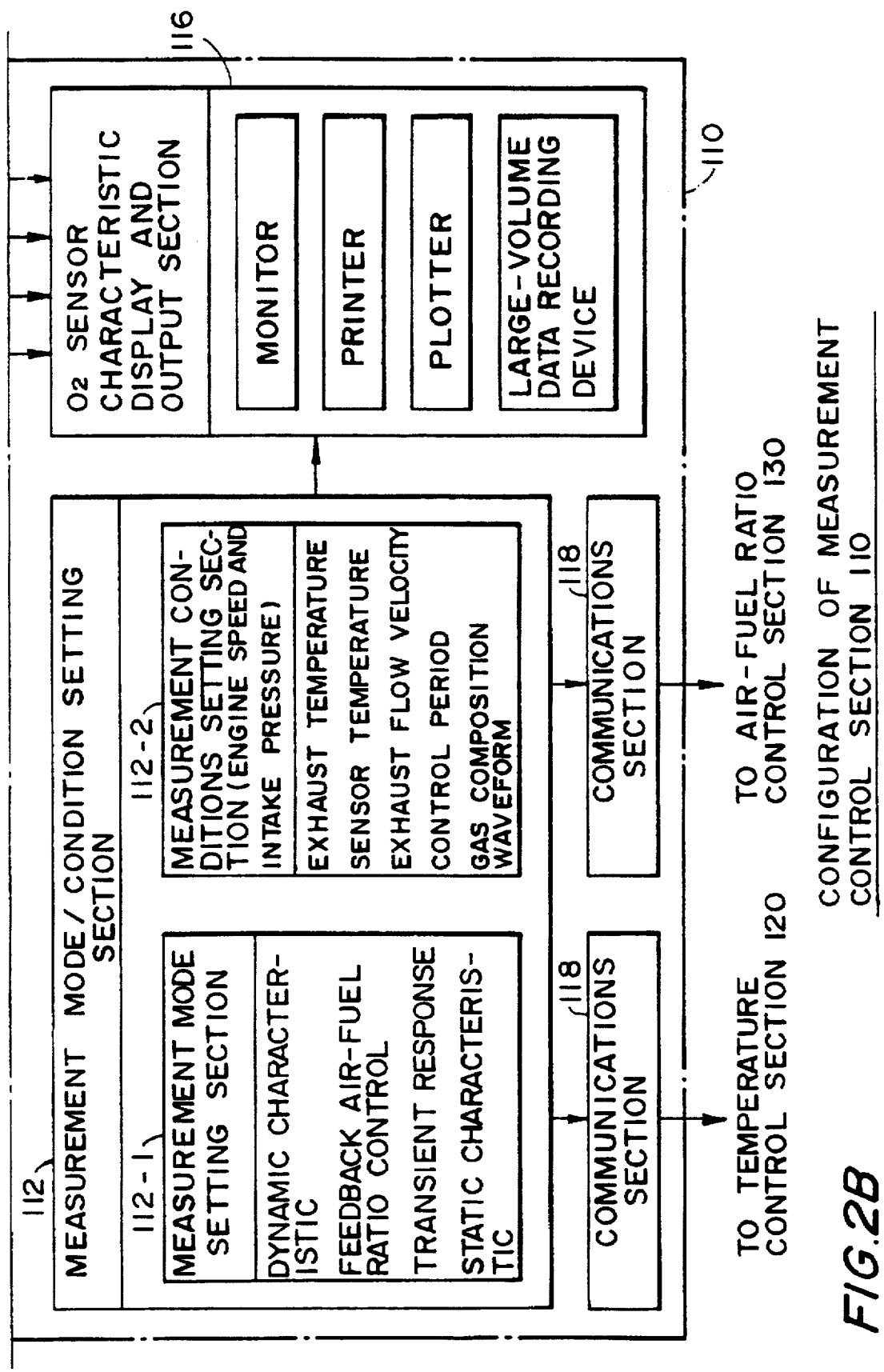

The configuration of the measurement control section 110 is shown in FIG. 2. The measurement control section 110 comprises a measurement mode/condition setting section 112, an $O_2$ sensor output processing section 114, and an $O_2$ sensor characteristic display and output section 116.

The measurement control section 110 also comprises a communications section 118 that transfers signals between the air ratio time-average measuring section 400, the temperature control section 120, and the air/fuel ratio control section 130.

The measurement mode/condition setting section 112 comprises a measurement mode setting section 112-1 and a measurement condition setting section 112-2. These setting sections 112-1 and 112-2 are constructed to display setup menus on a CRT display (not shown in the figure) to enable an operator to select settings from these menus.

The measurement mode setting section 112-1 specifies whether the value to be measured is a dynamic characteristic or a static characteristic. Since a dynamic characteristic includes characteristic of feedback air/fuel ratio control and the transient response characteristic, these factors must also be specified when a dynamic characteristic is specified. The characteristic of feedback air/fuel ratio control measures air/fuel ratio control states (such as air ratio time-average and output (electromotive force or resistance) waveform) by using the output (electromotive force or resistance) signal of the stoichiometric air/fuel ratio ($O_2$) sensor 10 to be measured to provide feedback control. A transient response characteristic shows variation of the output (electromotive force or resistance) waveform when there are variations in the air/fuel ratio of a rectangular or other well-known waveform. In this case, a static characteristic is the relationship between the output (electromotive force or resistance) of the stoichiometric air/fuel ratio ($O_2$) sensor to be measured and the air/fuel ratio.

The measurement condition setting section 112-2 is used to specify the type of automobile in which the stoichiometric air/fuel ratio ($O_2$) sensor will be mounted, its year of manufacture, the engine model, the transmission model, and the exhaust regulations. Thus the configuration is such that the type and model of the stoichiometric air/fuel ratio ($O_2$) sensor 10 that is used, together with the engine conditions (engine speed and intake pressure), exhaust flow velocity, exhaust temperature, exhaust composition, air/fuel ratio control period, and sensor temperature corresponding to the specified conditions, are automatically selected on the basis of previously input data. Note, however, that combinations of engine speed and intake pressure would be ideal when engine conditions are specified, but torque or engine power could be specified instead of intake pressure.

Ordinarily, it is best to measure the characteristics of the stoichiometric air/fuel ratio ($O_2$) sensor 10 under automatically selected engine conditions and exhaust conditions that are based on the above model and other specifications, but the configuration could also be such that other conditions can be specified if it should be necessary to measure characteristics under such conditions.

The measurement mode/condition setting section 112 is constructed to supply output signals to the $O_2$ sensor characteristic display and output section 116 and also to the temperature control section 120 and the air/fuel ratio control section 130, and it also receives signals from the two control sections 120 and 130.

The $O_2$ sensor output processing section 114 comprises a conversion section 114-1 for the output from the stoichiometric air/fuel ratio ($O_2$) sensor 10, an output (electromotive force or resistance) waveform recording section 114-2, and an output (electromotive force or resistance) waveform calculation section 114-3.

Figure 3:
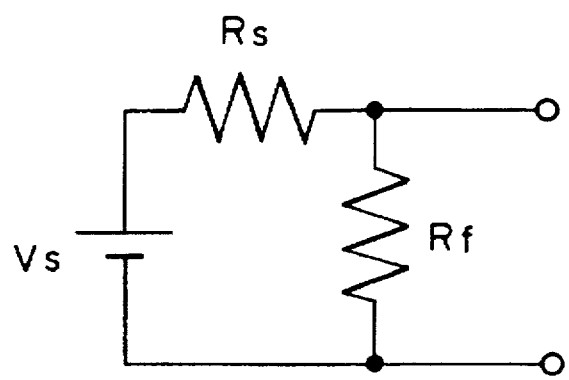
FIG. 3 is an explanatory diagram of a voltage-divider type of resistance-voltage conversion circuit.

The output conversion section 114-1 of the stoichiometric air/fuel ratio ($O_2$) sensor 10 is constructed to switch the details of the conversion as appropriate to suit the type and method of the stoichiometric air/fuel ratio ($O_2$) sensor that are specified as described above. In other words, if the stoichiometric air/fuel ratio ($O_2$) sensor 10 is of the oxygen concentration cell type, a buffer amplifier of an extremely high input impedance is used to enable faithful measurement of the electromotive force, to avoid any effects produced by the internal resistance of the sensor if it is high. If the type of stoichiometric air/fuel ratio ($O_2$) sensor is a resistor one, on the other hand, a circuit for converting a resistance into a voltage is used. A voltage-divider type of resistance-voltage conversion circuit or resistance-logarithm conversion circuit that is similar to that used in an automobile is suitable as the circuit for converting a resistance into a voltage. A voltage-divider type of resistance-voltage conversion circuit is one in which a resistance is connected in series with the stoichiometric air/fuel ratio ($O_2$) sensor, as shown in FIG. 3, a voltage is applied to the two ends thereof, and the voltage at a voltage-divider point is measured. In this figure, Vs denotes the applied voltage, Rs denotes the resistance of the stoichiometric air/fuel ratio ($O_2$) sensor, and Rf denotes a fixed resistance. The voltage between the two ends of Rf is used as an output voltage.

The circuit defined by Japanese Patent No. 1898791 is suitable as a resistance-logarithm conversion circuit.

A signal of the output conversion section 114-1 of the stoichiometric air/fuel ratio ($O_2$) sensor 10 is supplied to the air/fuel ratio control section 130. Output signals of the output (electromotive force or resistance) waveform recording section 114-2 and the output (electromotive force or resistance) waveform calculation section 114-3 are supplied to the $O_2$ sensor characteristic display and output section 116.

The $O_2$ sensor characteristic display and output section 116 not only displays data such as the air ratio time-average and output (electromotive force or resistance) waveform as $O_2$ sensor characteristics on a monitor, it also converts the format of this data for an output device such as a printer or plotter, and records the data on a large-volume data recording device such as a floppy disk or magnet-optical disk.

Note that target values for measurement and control, and instructions concerning operating conditions and other factors are sent out to the measurement control section 110 through the communications section 118 that provides communications with each of the air ratio time-average measuring section 400, the temperature control section 120, and the air/fuel ratio control section 130. Data on measurements and control results is posted to the other components in the same manner. If the apparatus of this embodiment also comprises the air/fuel ratio waveform measuring section 500, a signal fetch section is also provided for receiving measurement results from these other components.

A-2 Temperature Control Section

Figure 4:
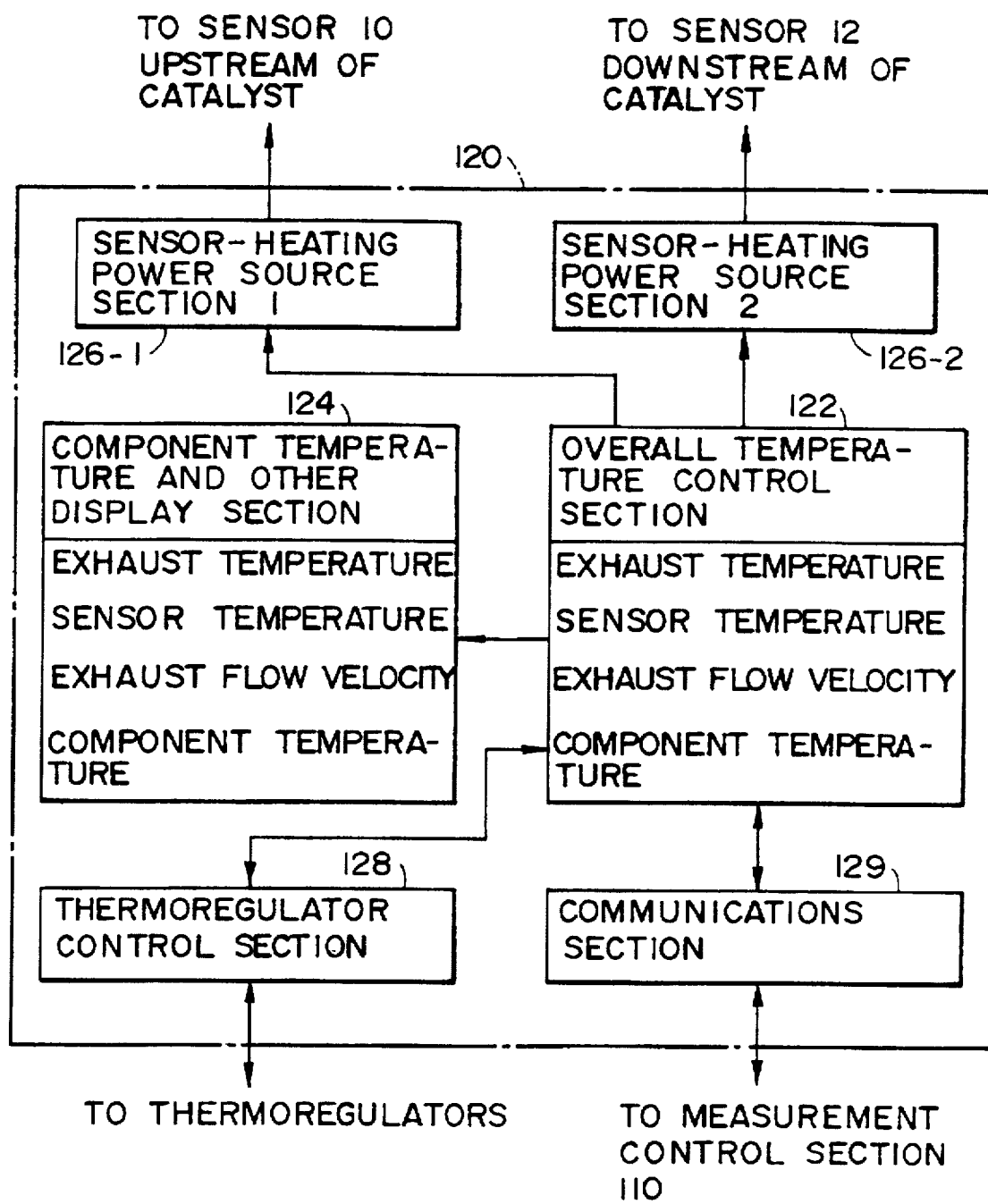
FIG. 4 is a block diagram of the temperature control section of the embodiments.

The configuration of the temperature control section 120 is shown in FIG. 4.

The temperature control section 120 of this embodiment comprises an overall temperature control section 122, a component temperature and other display section 124, sensor-heating power source sections 126-1 and 126-2, a thermoregulator control section 128, and a communications section 129.

The overall temperature control section 122 provides overall control over the exhaust temperature, sensor temperature, exhaust flow velocity, and component temperatures on the basis of the instructions of the measurement control section 110.

The component temperature and other display section 124 displays data such as exhaust temperature, sensor temperature, exhaust flow velocity, and component temperatures on a monitor.

The sensor-heating power source sections 126-1 and 126-2 are voltage-settable DC power sources that apply the same voltages as those applied in an actual engine if it is necessary to apply power to the built-in sensor heater under engine conditions that are used during testing.

The thermoreguator control section 128 issues temperature-setting instructions for a group of thermoregulators and it also receives reports of current temperature.

The communications section 129 transfers instructions to and from the measurement control section 110, and posts the execution state of these instructions.

It is difficult to prevent the heater from deteriorating, and it is also difficult to predict the breakage thereof. If by some chance the heater should break, a heater breakage warning signal is automatically received by the communications section 129 of the temperature control section 120 of this embodiment, and the communications section is thus used to automatically warn the measurement control section 110.

Under normal conditions when there is no heater breakage, the exhaust temperature specified by the above described menu is taken to be a target value and the communications section 129 is used to automatically send temperature-setting instructions to the thermoregulators of the heaters for heating the gas or keeping the piping hot, in accordance with a temperature-increase pattern that is set to ensure that the specified rate of increase of temperature is not exceeded, and thus set the temperature.

Figure 5:
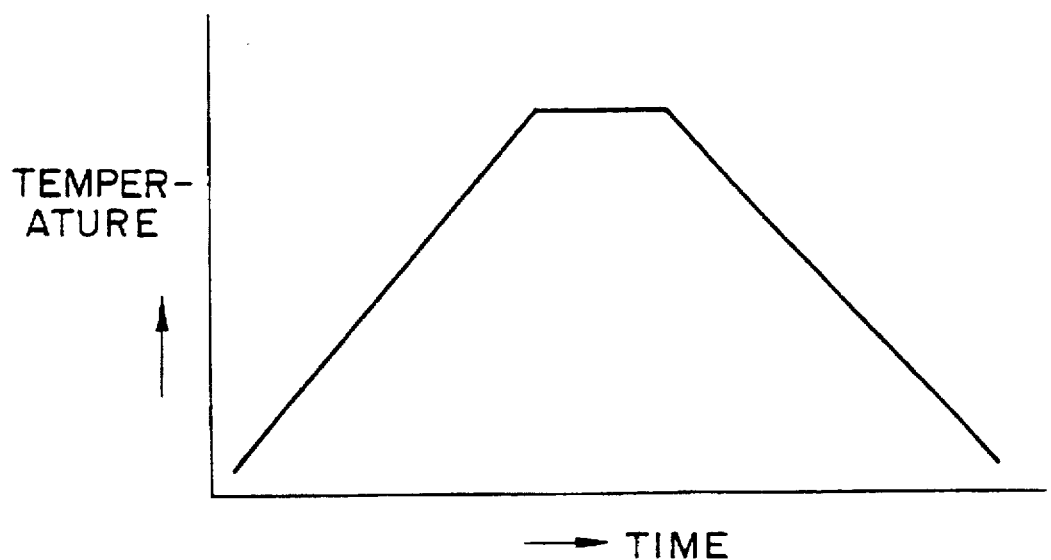
FIG. 5 is an explanatory diagram of a typical temperature-increase pattern for the stoichiometric air/fuel ratio sensor.

An example of a temperature-increase pattern for the stoichiometric air/fuel ratio ($O_2$) sensor 10 is shown in FIG. 5.

At preset regular intervals, the temperature control section 120 of this embodiment uses the communications section 129 to read out the temperatures of the components from the thermoregulators, calculate the discrepancy between each set temperature and the actual temperature, and check that there is no abnormality.

To prevent the occurrence of unwanted deterioration or a dangerous situation caused by a component overheating because of some sort of abnormality in a temperature-control thermoregulator or thermocouple, each heater is also provided with a protective thermoregulator and thermocouple. If the preset stable permissible temperature should be exceeded by this protective thermoregulator, the heating is halted (the heater current is cut), regardless of the control state and display of the temperature-control thermoregulator, and a warning is issued to inform the operator that an abnormality (excessive temperature rise) has occurred.

A-3 Air/fuel ratio Control Section

Figure 6:
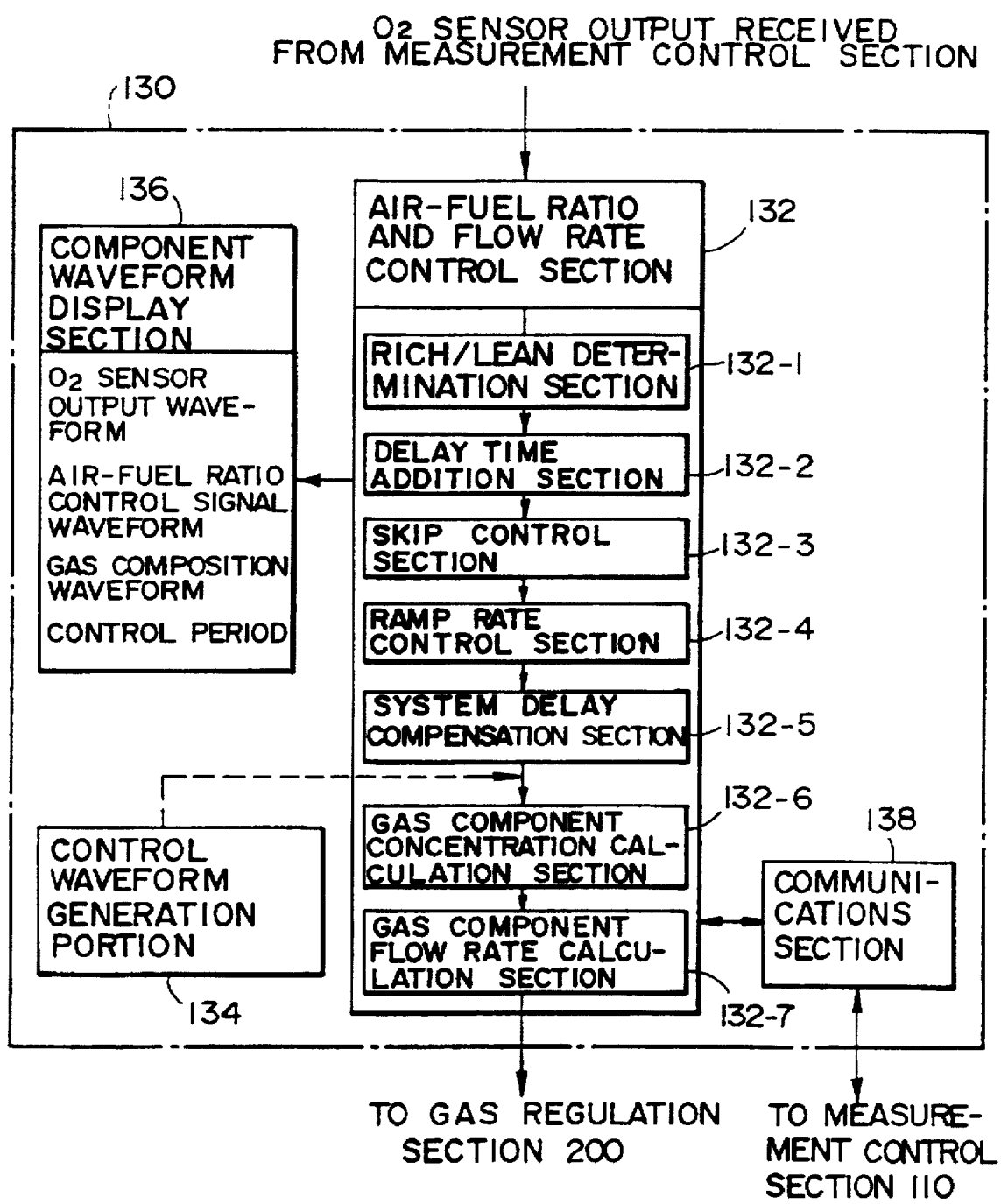
FIG. 6 is a block diagram of the air/fuel ratio control section of the embodiments.

The configuration of the air/fuel ratio control section 130 is shown in FIG. 6.

The air/fuel ratio control section 130 of this embodiment comprises an air/fuel ratio and flow rate control section 132, control waveform generation portion 134, a component waveform display section 136, and a communications section 138.

The air/fuel ratio and flow rate control section 132 further comprises a rich/lean determination section 132-1, a delay time addition section 132-2, skip control section 132-3, a ramp rate control section 132-4, a system delay compensation section 132-5, gas component concentration calculation section 132-6, and a gas component flow rate calculation section 132-7.

The control waveform generation portion 134 is constructed to cause the generation of an air/fuel ratio waveform that is used when the transient response characteristic of the $O_2$ sensor to be measured is being measured when being controlled by a special air/fuel ratio waveform.

The component waveform display section 136 is constructed to cause the display of data such as the $O_2$ sensor output (electromotive force or resistance) waveform, air/fuel ratio control signal waveform, gas composition waveform, and control period.

The communications section 138 receives instructions concerning air/fuel ratio control mode and gas composition from the measurement control section, and is also constructed to cause the measurement control section 110 to be informed of details such as the execution status of instructions and the control waveform.

Figure 7:
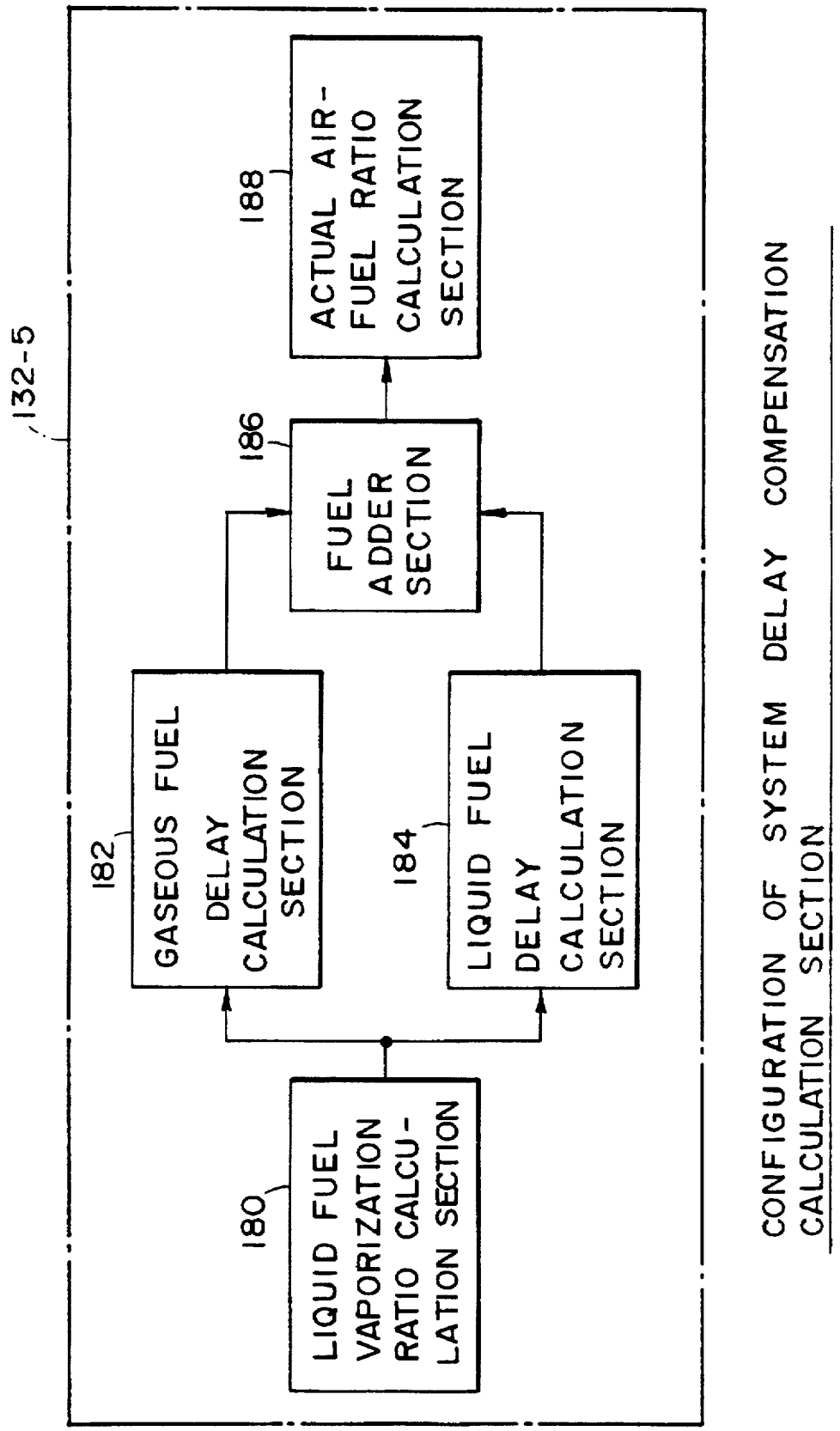
FIG. 7 is a block diagram of the system delay compensation calculation section of the embodiments.

A system delay compensation calculation section 132-5 shown in FIG. 7 comprises a liquid fuel vaporization ratio calculation section 180, a gaseous fuel delay calculation section 182, a liquid fuel delay calculation section 184, a fuel adder section 186, and an actual air/fuel ratio calculation section 188. It is constructed in such a manner that it converts an air ratio waveform A in FIG. 8 which is input to the calculation section 182, into an air ratio waveform B in FIG. 8 for the actual engine.

Note that the gaseous and liquid fuel delay calculation sections are formed of primary or higher-order delay calculation sections.

B. Gas Regulation Section

Figure 9B:
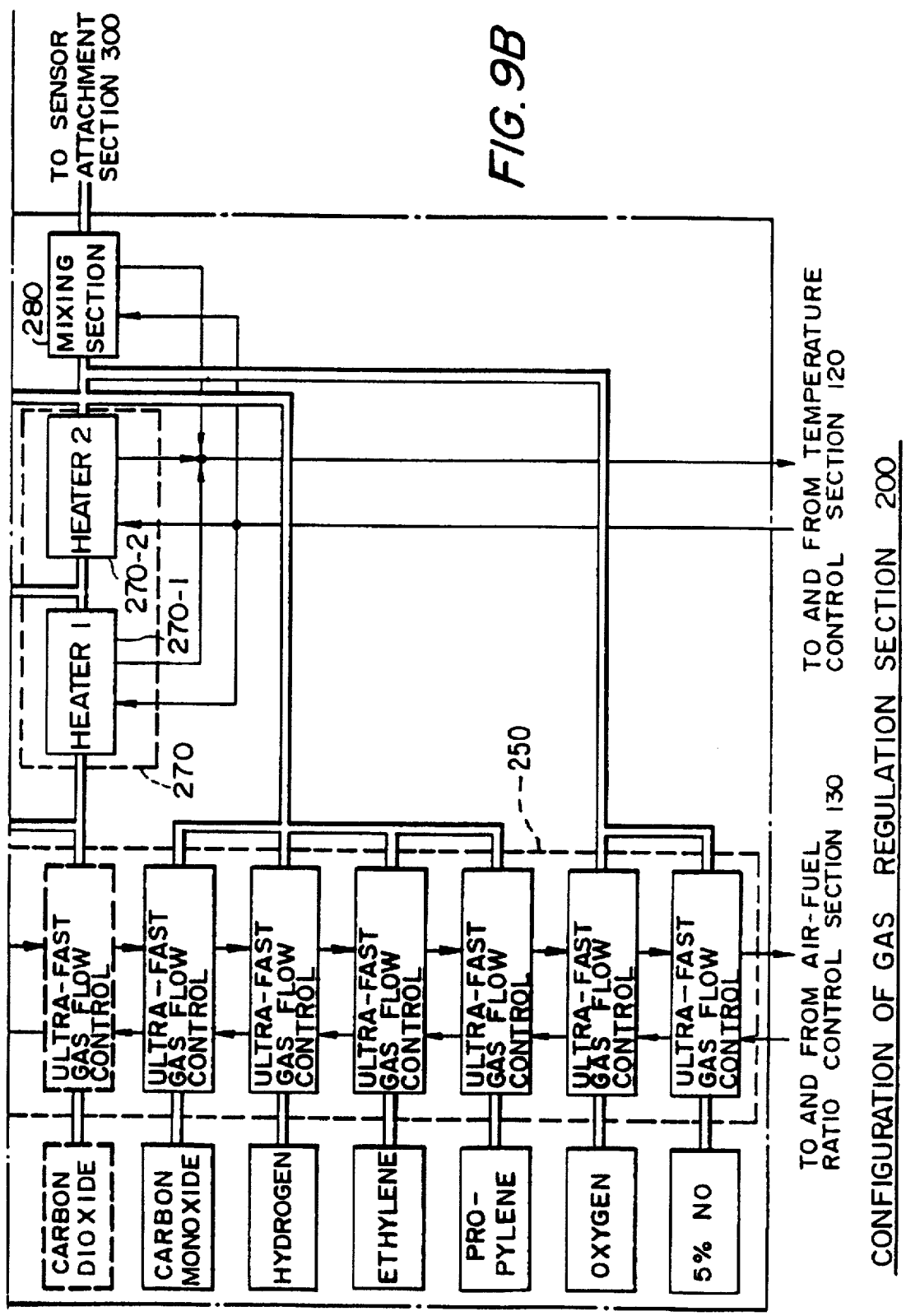

The configuration of the gas regulation section 200 is shown in FIG. 9. The gas regulation section 200 of this embodiment comprises a supply section 210 for gas or liquid components, a liquid flow control section 240, a gas flow control section 250, an atomization section 260, a heater section 270, and a mixer section 280.

B-1 Supply Sections for Gaseous and Liquid Components

The present inventors have discovered that, of the gases within an engine's exhaust, the following seven components have a large effect on the output (electromotive force) of an $O_2$ sensor: nitrogen ($N_2$), water vapor ($H_2O$), carbon monoxide (CO), hydrogen ($H_2$), hydrocarbons (HC), oxygen ($O_2$), and nitric oxide (NO). That is why the supply section 210 of this embodiment is constructed to supply these seven components.

In addition, they have discovered that the hydrocarbons (HC) within the exhaust consist of at least 20 components, even if only the comparatively high-concentration components are counted, and they have determined the concentrations of these components quantitatively. They have also determined by consideration of amounts of oxygen consumed that, of these components, the ones that have the greatest effect on the output (electromotive force) signal of the $O_2$ sensor are: ethylene ($C_2H_4$), toluene ($C_7H_8$), and propylene($C_3H_6$). That is why the supply section 210 of this embodiment is constructed to further supply one or a combination of a plurality of these three components.

Since carbon dioxide ($CO_2$) acts to suppress the oxidation reaction of carbon monoxide (CO) in the vicinity of the electrodes of the $O_2$ sensor and thus lower the electromotive force, it is preferable that it is added to the above described seven components to provide eight components that enable the achievement of an electromotive force waveform close to that of an actual engine.

B-2 Gas Flow Control Section

In order to reproduce the air/fuel ratio waveform of an engine faithfully, it is necessary to reproduce the concentration (flow rate) waveform of each of the gas components faithfully. The concentration (flow rate) waveform of each of the gas components includes high-frequency components at several tens of Hertz, and it is necessary to reproduce waveforms that include these high-frequency components. An ultra-fast gas flow controller is required in order to reproduce these high-frequency components of the concentration (flow rate). Therefore, the control means of Japanese Patent Application No. 4-287851 is used as the gas flow control section 250 of this embodiment.

B-3 Liquid Flow Control Section

A liquid-transfer pump is used as the liquid flow control section 240. Note that it is preferable to use a liquid-transfer pump that has a flow rate control function as this liquid flow control section 240, and it is even more preferable that it is a liquid-transfer pump having both a flow rate instruction signal communications function and a flow rate control function.

B-4 Atomization Section

To mix the liquid components as evenly as possible with the other gaseous components, an ultrasonic atomizer 262 is used as the atomization section 260.

To carry the atomized components by a carrier gas, the atomization section 260 could be constructed of a combination of the ultrasonic atomizer 262 and supply section 264 for supplying a carrier gas which flow rate is controlled.

The carrier gas is transferred together with the atomized components to the sensor attachment section 300. Therefore, since a carrier gas that is either oxidized or reduced would have an effect on the characteristic of the $O_2$ sensor, it is preferable that the carrier gas is neither oxidizing nor reducing. Thus the neutral gas nitrogen is used as the carrier gas that is supplied to the atomization section 260 of this embodiment.

Even if the carrier gas is the neutral gas nitrogen, if it is supplied from an independent piping system, any variations in the flow of this carrier gas would cause variations in the overall flow rate, and it would be difficult to prevent resultant effects on the concentration. To avoid this problem, it is preferable that the carrier gas supplied to the atomization section 260 is made to be a separated part of the $N_2$ that has already been metered by the gas flow control section 250, so that there will no effect on concentration if there should be small fluctuations in the flow rate.

B-5 Heater Section

To prevent the condensation on the wall surfaces of atomized water that has been added to the gas, the heater section 270 of this embodiment is divided into two heater sections 270-1 and 270-2 that are connected in series, and the atomized water is added between these heater sections.

To further prevent the condensation on the wall surfaces of atomized water that has been added to the gas, a first branch pipeline 272 branches out either horizontally or at an angle of up to 30° from the horizontal from partway along the main pipeline connecting the two serially connected heater sections 270-1 and 270-2, and atomized water is added through this branch pipeline 272.

To even further prevent the condensation on the wall surfaces of atomized water that has been added to the gas, a partition is provided within the first branch pipeline 272 to divide it vertically. This partition is constructed to extend along the approximate center of the main pipeline to block off between 20% and 100% of the cross-sectional area of the main pipe. All or part of the gas that has been heated by the first heater section 270-1 and is flowing through the main pipeline is guided below the partition in the first branch pipeline 272, passes through the portion at the end section of the first branch pipeline 272 where the partition is not provided, and is guided over the partition to return to the main pipe. An opening portion is provided in the upper surface of the first branch pipeline 272 and atomized water is added through this branch pipeline portion.

To prevent the ultrasonic atomizer 260 from being damaged caused by heating due to the high-temperature gas flowing through the first branch pipeline 272, a second branch pipeline 274 having an opening portion at an end section thereof could be provided either vertically or at an angle of up to 30° from the vertical, from an opening portion provided in the upper surface of the first branch pipeline 272, and the ultrasonic atomizer could be arranged in an upper portion thereof.

To prevent the water that is atomized by the ultrasonic atomizer 260 from coming into contact with the inner surface of this second branch pipeline 274 and recondensing thereon, a downward gas flow (a gas curtain) could be provided along the inner wall surface of the second branch pipeline 274.

B-6 Mixer Piping

To suppress reactions within the resulting gases that carbon monoxide (CO), hydrogen ($H_2$), ethylene ($C_2H_4$), propylene ($C_3H_6$), oxygen ($O_2$), nitric oxide (NO), and atomized toluene ($C_7H_8$) are mixed with a carrier gas, which are supplied at controlled flow rates, and also suppress any corruption of the controlled flow rate waveforms, the piping for each gas is connected independently to a rear portion of the two serially connected heater sections 270-1 and 270-2.

Another good method of suppressing any reactions between the combustible gases and combustion-supporting gases that may occur when they flow together would be to connect the piping in which the combustible gases (carbon monoxide (CO), hydrogen ($H_2$), ethylene ($C_2H_4$), and propylene ($C_3H_6$)) are combined at controlled flow rates, the piping which the combustion-supporting gases (oxygen ($O_2$) and nitric oxide (NO)) are combined at controlled flow rates, and the piping in which the atomized toluene ($C_7H_8$) is mixed with the carrier gas, independently to a rear portion of the two serially connected heater sections.

B-7 Pressure Error Compensation Means

A laminar flowmeter (refer to Japanese Patent Application No. 4-287851) is used as the flow rate measuring means in the gas flow control section 250 of this embodiment. Since this laminar flowmeter is a volumetric flowmeter, a flow rate that is measured thereby is a volumetric flow rate, not a mass flow rate. If a mass flow rate is necessary, it can be obtained by a multiplying the volumetric flow rate by the gas density. If temperature is constant, the gas density is proportional to the absolute pressure. If the temperature and absolute pressure are constant, volumetric flow rate and mass flow rate are proportional to one another, so that it is simple to obtain an output corresponding to a mass flow rate by measuring the volumetric flow rate. In this case, variations in absolute pressure will cause errors if the objective is to attempt to measure mass flow rate. Therefore, an absolute pressure measurement means is provided in the main pipeline at each joint section where one of the gases joins the main pipeline, and a portion of the gas of a flow rate measured within the flow rate controller is used to compensate for the pressure-dependent flow rate measurement error.

Note that this configuration, in which an absolute pressure measurement means is provided in the main pipeline at each gas joint section, and a means for automatically adjusting the degree of opening of a throttle valve provided at the end of the flow path is provided to set the pressure to a preset constant value, makes it unnecessary to compensate for any pressure-dependent flow rate measurement error.

B-8 Mixer Section

Since it is difficult to mix gases uniformly in the main pipeline by merely connecting the piping for each gas to the main pipeline, it is not possible to measure the characteristic of the $O_2$ sensor stably. To counter that problem, a static type of in-pipe mixer is provided as the mixing section 280 in a rear portion of the joint section, to encourage the mixing of gases.

C. Sensor Attachment Section

The configuration around the sensor attachment section differs between the first embodiment shown in FIG. 1 and the second embodiment shown in FIG. 10, as will be described later.

The configurations of the air ratio time-average measuring section 400 and the air/fuel ratio waveform measuring section 500 will also be described later.

Specific configurations of the systems shown in FIGS. 1 and 10 will now be described in more detail, together with descriptions of the operation thereof.

Measurement Control Section 110

The measurement control section 110 of these embodiments has the function of measuring characteristics under the same conditions as the exhaust and air/fuel ratio control conditions that occur under predetermined engine conditions.

The measurement mode/condition setting section 112 of these embodiments is constructed to display a characteristic measuring menu on a monitor to enable the operator to select the type of automobile, engine model, transmission model, type of stoichiometric air/fuel ratio ($O_2$) sensor, and an exhaust testing mode.

Engine conditions that match these factors are automatically specified by this selection.

If engine conditions are automatically specified by the above described specification of factors such as the type of automobile, values of exhaust flow velocity, exhaust temperature, stoichiometric air/fuel ratio ($O_2$) sensor temperature, sensor-heating heater voltage, air/fuel ratio control period, air/fuel ratio control constants (delay time, skip, and ramp rate), and the relationship between air/fuel ratio and exhaust composition, which were previously measured by using an actual engine, are automatically called from a data file and these conditions are automatically set for use in the testing. However, if it is necessary to use special values for these factors, the operator can specify them.

There are two main types of air/fuel ratio control system, depending on factors such as the type of automobile and the engine model:

The first air/fuel ratio control system (FIG. 1);

The second air/fuel ratio control system (FIG. 10).

In principle, there are three characteristic measurement items, and the operator usually measures them but if there are items to be omitted the operator can instruct to omit them:

Air/fuel ratio control characteristic;

Static electromotive force (resistance) vs. air/fuel ratio (or gas density) characteristic;

Transient electromotive force (resistance) response characteristic.

If the rate of increase of temperature is too high, the temperature difference between components of the stoichiometric air/fuel ratio ($O_2$) sensor 10 could become too large, which would lead to huge thermal stresses that could cause breakage or deterioration. Therefore, a rate of increase of temperature that is slightly lower than a permissible value for the rate of increase of temperature is usually set automatically, and the operator can specify a particularly low value for the rate of increase of temperature if necessary.

Air/fuel ratio Control Section 130

The air/fuel ratio is controlled under a mode corresponding to the air/fuel ratio control system (either the system of FIG. 1 or that of FIG. 10) and the characteristic measurement item, by instructions issued from the measurement control section 110 through the communications means.

As stated in the paragraphs on the measurement control section 110, there are two main types of air/fuel ratio control system, depending on the type of automobile and engine model:

The air/fuel ratio control system of FIG. 1;

The air/fuel ratio control system of FIG. 10.

As stated in the paragraphs on the measurement control section 110, there are three characteristic measurement items:

Air/fuel ratio control characteristic;

Static electromotive force (resistance) vs. air/fuel ratio (or gas density) characteristic;

Transient electromotive force (resistance) response characteristic.

Air/fuel ratio Control System of FIG. 1

A. Air/fuel ratio Control Characteristic

The air/fuel ratio control section 130 compares a preprocessed output signal (electromotive force of resistance) of the stoichiometric air/fuel ratio ($O_2$) sensor 10 to be measured against a stoichiometric air/fuel ratio identification reference value (voltage or resistance), and determines the direction of any deviation from the stoichiometric air/fuel ratio. Note that this output signal is preprocessed by a buffer amplifier if the sensor is of the oxygen concentration cell type or by a voltage-divider circuit or (logarithmic type of) resistance converter if the sensor is of the resistor type, according to signals specifying air/fuel ratio control in the sensor attachment section 300.

For an oxygen concentration cell type of sensor, an electromotive force that is larger than the corresponding reference value means fuel-rich; for an n-type oxide semiconductor (such as titanium dioxide or niobium pentoxide) resistor type of sensor, a resistance that is larger than the corresponding reference value means fuel-lean.

The air/fuel ratio control section 130 performs air/fuel ratio control on the gas regulation section 200 in accordance with air/fuel ratio control constants (delay time, skip, and ramp rate), to correct the deviation from the stoichiometric air/fuel ratio.

A-1 Delay Time

In this case, a delay time provides a suitable control by using a signal that is delayed by only a preset time with respect to the timing of an inversion in the direction of deviation as determined by the output of the stoichiometric air/fuel ratio ($O_2$) sensor 10. The delay times in each direction are expressed by the following symbols.

$DT_{(R \to L)}$: Delay time added when the direction of deviation from the stoichiometric air/fuel ratio has inverted from rich to lean $DT_{(L \to R)}$: Delay time added when the direction of deviation from the stoichiometric air/fuel ratio has inverted in the opposite direction The objective of adding these delay times is to compensate for any unbalance in transient response times dependent on the direction of change of the air/fuel ratio, which is inherent to the stoichiometric air/fuel ratio ($O_2$) sensor 10.

The transient response times of the stoichiometric air/fuel ratio ($O_2$) sensor 10 are expressed by the following symbols.

$\tau_{(R \to L)}$: Transient response time when the air/fuel ratio changes from rich to lean $\tau_{(L \to R)}$: Transient response time when the air/fuel ratio changes in the opposite direction These transient response times of the stoichiometric air/fuel ratio ($O_2$) sensor 10 are usually in the following relationship:

$$\tau_{(R \to L)} > \tau_{(L \to R)} \quad (1)$$

If this unbalance between the transient response times of the stoichiometric air/fuel ratio ($O_2$) sensor 10 is not compensated for, the control air/fuel ratio (time-averaged value) will deviate slightly from the stoichiometric air/fuel ratio in the lean direction. The amount of this deviation depends on conditions such as the concentration of unburned components in the exhaust, but is usually on the order of 1 to 5% (1.01 to 1.05 if expressed in terms of the air ratio). In this case, the air ratio is the air/fuel ratio divided by the stoichiometric air/fuel ratio.

It may seem that this slight deviation of only 1 to 5% toward the lean side from the stoichiometric air/fuel ratio is not very significant, but it cannot be ignored because it has extremely large effects in a three-way catalyst system, such as greatly lowering the $NO_x$ purifying efficiency, as stated previously.

That is why any unbalance in the transient response times of the stoichiometric air/fuel ratio ($O_2$) sensor 10 is compensated for with delay times provided in the air/fuel ratio control section 130, to remove (reduce) the unbalance in transient response time in appearance. For that purpose, the sum of the transient response time and delay time in each direction in which the air/fuel ratio changes could be used. The resultant relationship is expressed by the following equation:

$$\tau_{(R \to L)} + DT_{(R \to L)} = \tau_{(L \to R)} + DT_{(L \to R)} \quad (2)$$

This response time compensation virtually eliminates any deviation from the stoichiometric air/fuel ratio toward the lean side, so that control is centered on the stoichiometric air/fuel ratio. This has an extremely large practical advantage in obtaining a high purifying efficiency with respect to $NO_x$.

A-2 Skip

A skip creates a signal that is delayed by a preset delay time with respect to the timing of an inversion in the direction of deviation, as determined by the above described output of the stoichiometric air/fuel ratio ($O_2$) sensor 10, and compensates constant-amplitude air/fuel ratio at the point at which that delayed signal inverts. This skip acts to provide an air/fuel ratio amplitude that is always constant and also shortens the control period thereof, while keeping the average value of air/fuel ratio control at the stoichiometric air/fuel ratio. The objective of adding these skips is to increase on the purifying efficiency of the three-way catalyst (reduce the quantity of harmful components discharged).

With a platinum (Pt)-rhodium (Rh) type of catalyst, which is generally used as this three-way catalyst, it is known that a purifying efficiency that is higher than that obtained when the stoichiometric air/fuel ratio is held constant is obtained by allowing the air/fuel ratio to oscillate at constant amplitude between rich and lean while the time-averaged value thereof is held at the stoichiometric air/fuel ratio. Skips are added to utilize this phenomenon to the utmost. Assume that the skips in each direction are expressed by the following symbols.

$S_{(R \to L)}$: Skip added when the direction of deviation from the stoichiometric air/fuel ratio has inverted from rich to lean $S_{(L \to R)}$: Skip added when the direction of deviation from the stoichiometric air/fuel ratio has inverted in the opposite direction.

In a basic air/fuel ratio control system, the same absolute value with only the sign being different is often selected for the skips $S_{(R \to L)}$ and $S_{(L \to R)}$ in opposite directions.

$$S_{(R \to L)} = -S_{(L \to R)} \quad (3)$$

A-3 Ramp Rate

A ramp rate compensate air/fuel ratio at a constant proportion that is per unit time, at the point at which the above described delayed signal inverts. In the case of the proportional integral and differential (PID) control or the like, it is usual to apply compensation of a magnitude that is proportional to the deviation between the target value and the control value. With the stoichiometric air/fuel ratio ($O_2$) sensor 10, however, the abruptly changing characteristic of the output (electromotive force or resistance) at the stoichiometric air/fuel ratio means that only the direction of deviation can be obtained as valid information as shown in FIG. 21; the magnitude of the deviation is not valid information. Therefore, it is not possible to apply compensation of a magnitude proportional to the deviation, and thus air/fuel ratio compensation is applied at a proportion that is constant per unit time. Assume that the ramp rates in each direction are expressed by the following symbols.

$RR_{(R \to L)}$: Ramp rate added when the direction of deviation from the stoichiometric air/fuel ratio has inverted from rich to lean $RR_{(L \to R)}$: Ramp rate added when the direction of deviation from the stoichiometric air/fuel ratio has inverted in the opposite direction.

In a basic air/fuel ratio control system, the same absolute value with only the sign being different is often selected for the ramp rates $RR_{(R \to L)}$ and $RR_{(L \to R)}$ in opposite directions.

$$RR_{(R \to L)} = -RR_{(L \to R)} \quad (4)$$

The above described air/fuel ratio control is used in an actual engine, so the apparatus for analyzing air/fuel ratio sensor characteristics also uses it.

Figure 11:
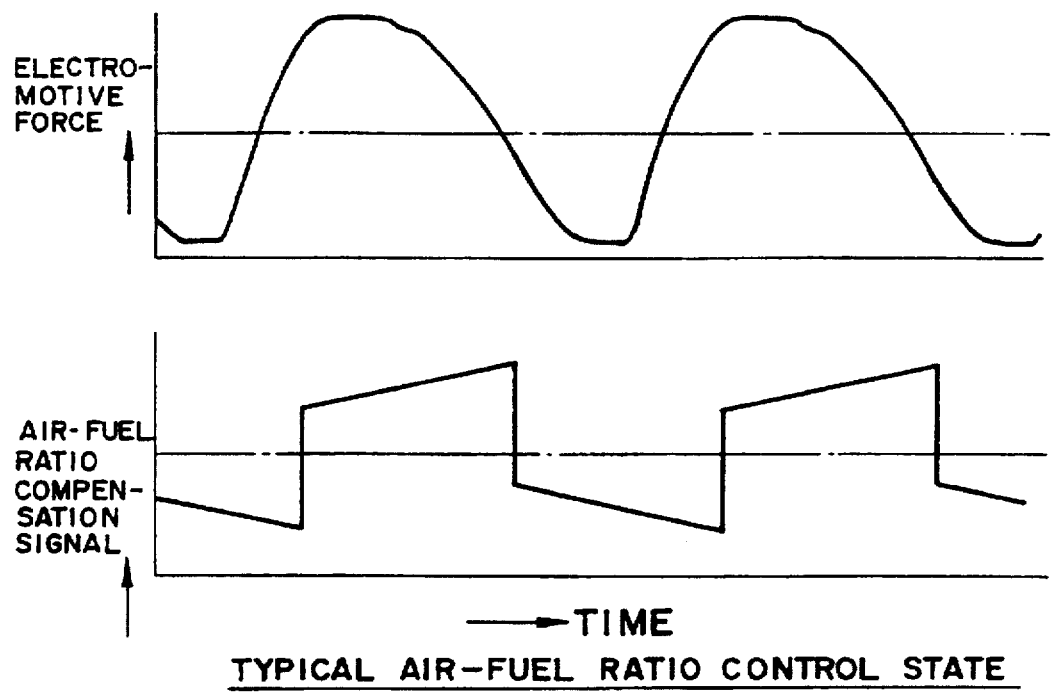
FIG. 11 is an explanatory diagram of a typical state of air/fuel ratio control.

The air/fuel ratio control section 130 of this embodiment applies air/fuel ratio control by using these three air/fuel ratio control constants (delay time, skip, and ramp rate), as shown in FIG. 11.

B. Static Electromotive Force (Resistance) Vs. Air/fuel ratio (Or Gas Density) Characteristic For this static characteristic, the air/fuel ratio control section 130 varies the air/fuel ratio in accordance with factors such as the lower limit, upper limit, hold time, direction of air/fuel ratio change, and air/fuel ratio change pattern of the previously specified air/fuel ratio (or gas density).

C. Transient Electromotive Force (Resistance) Response Characteristic

For this transient response characteristic, the air/fuel ratio control section 130 varies the air/fuel ratio in accordance with factors such as the lower limit, upper limit, hold times at the upper and lower limits, and air/fuel ratio change waveform of the previously specified air/fuel ratio (or gas density).

Air/fuel ratio Control System of FIG. 10

In the second air/fuel ratio control system shown in FIG. 10, two stoichiometric air/fuel ratio ($O_2$) sensors 10 and 12 are mounted, one upstream and one downstream from the three-way catalyst 600, and output (electromotive force or resistance) signals therefrom are used together to provide a high level of air/fuel ratio control. The configuration thereof is shown in FIG. 4.

The objective of air/fuel ratio control provided by the second air/fuel ratio control system is, while maintaining the same high-speed air/fuel ratio control (short control period) as that of the first air/fuel ratio control system by the stoichiometric air/fuel ratio ($O_2$) sensor 10 placed on the upstream side of the three-way catalyst 600, to use the other stoichiometric air/fuel ratio ($O_2$) sensor 12 placed on the downstream side of the three-way catalyst 600 to detect variations in the control air/fuel ratio (time-averaged value) caused by variations in the stoichiometric air/fuel ratio detection characteristic of the stoichiometric air/fuel ratio ($O_2$) sensor 10 on the upstream side thereof, and reduce these variations by applying compensation. This compensation for variations in the control air/fuel ratio (time-averaged value) reduces variations in the quantity of harmful components discharged.

A. Air/fuel ratio Control Characteristic

First of all, air/fuel ratio control is performed by the stoichiometric air/fuel ratio ($O_2$) sensor 10 placed on the upstream side of the three-way catalyst 600 in the same manner as in the first air/fuel ratio control system, using the three air/fuel ratio control constants (delay time, skip, and ramp rate).

Next, a skip compensation signal is created by the stoichiometric air/fuel ratio ($O_2$) sensor 12 placed on the downstream side of the three-way catalyst 600 in the same manner as in the first air/fuel ratio control system, using three control constants (downstream delay time, downstream skip, and downstream ramp rate). These three downstream control constants have names similar to those of the three upstream control constants, but these are set independently to appropriate values. This skip compensation signal is used to adjust the skip that is one of the upstream air/fuel ratio control constants.

As mentioned previously, in the first control system shown in FIG. 1, the same absolute value with only the sign being different is often selected for the skips $S_{(R \rightarrow L)}$ and $S_{(L \rightarrow R)}$ in opposite directions. However, in the second air/fuel ratio control system shown in FIG. 10, the sum of the skips $S_{(R \rightarrow L)}$ and $S_{(L \rightarrow R)}$ in opposite directions is kept constant, but the control air/fuel ratio (time-averaged value) can be adjusted by varying (under automatic control) the individual magnitudes of these skips.

Figure 12:
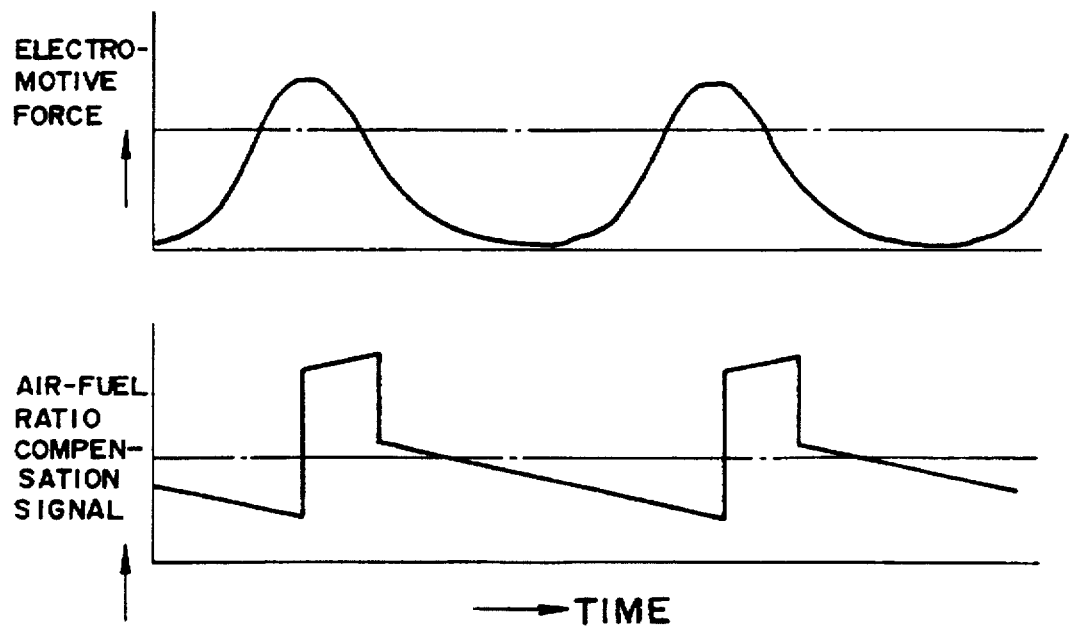
FIG. 12 is an explanatory diagram of a state obtained when the apparatus of FIG. 10 is used to provide air/fuel ratio control.

An example of this is shown in FIG. 12. This example shows an air/fuel ratio control waveform where the output (electromotive force or resistance) of the stoichiometric air/fuel ratio ($O_2$) sensor 12 downstream from the catalyst tends to be on the rich side, so that skip $S_{(R \rightarrow L)}$ is manipulated to have a magnitude that is 60% of skip $S_{(L \rightarrow R)}$. With this control, the proportion of time that the output (electromotive force or resistance) electromotive force of the stoichiometric air/fuel ratio ($O_2$) sensor 10 upstream from the catalyst is less than the reference voltage is lengthened, to compensate the control air/fuel ratio (time-averaged value) toward the lean side. This automatic control enables compensation of deviations from the stoichiometric air/fuel ratio of the output (electromotive force or resistance) of the stoichiometric air/fuel ratio ($O_2$) sensor 12 downstream from the catalyst.

B. Static Electromotive Force (Resistance) vs. Air/fuel ratio (Or Gas Density) Characteristic For this static characteristic, the air/fuel ratio is varied in accordance with factors such as the lower limit, upper limit, hold time, direction of air/fuel ratio change, and air/fuel ratio change pattern of the previously specified air/fuel ratio (or gas density).

This is the same as in the first air/fuel ratio control system.

C. Transient Electromotive Force (Resistance) Response Characteristic

For this transient response characteristic, the air/fuel ratio is varied in accordance with factors such as the lower limit, upper limit, hold times at the upper and lower limits, and air/fuel ratio change waveform of the previously specified air/fuel ratio (or gas density).

This is the same as in the first air/fuel ratio control system.

Gas Regulation Section 200

The gas regulation section 200 is further divided into the flow rate control sections 240 and 250 and the heater and mixer sections 270 and 280.

The flow rate control sections 240 and 250 control the gas flows on the basis of instructions concerning the flow rate of each gas component from the air/fuel ratio control section 130. For components which are liquid at room temperature (20° C.) (water vapor ($H_2O$) and toluene ($C_7H_8$)), these sections control the liquid flows, atomize them by an atomizer, then mix them.

The heater and mixer sections 270 and 280 use a heater to heat the nitrogen ($N_2$) alone of the gases at control led flow rates to a predetermined temperature, then atomize the water and mix it in. Since the gas temperature after the mixing is reduced by the latent heat of vaporization of the water and the thermal capacity of the water vapor, it is reheated to a predetermined temperature by a second-stage heater.

The combustible components (hydrogen ($H_2$), carbon monoxide (CO), and hydrocarbons (HC)) and combustion-supporting components (oxygen ($O_2$) and nitrogen oxides ($NO_x$)) are then mixed in.

One reason why the combustible and combustion-supporting components are not heated after being mixed, but are mixed after the nitrogen and water vapor are heated, is that if the combustible and combustion-supporting components are heated after being mixed together, combustion reactions between these components would be encouraged at local high-temperature portions on the heater surfaces or in the vicinity thereof, causing a decrease in the concentration of unburned components. If the mixing is done after the heating, the gas containing both combustible and combustion-supporting components does not come into contact with the heater, and thus there is no encouragement of combustion reactions between these components at local high-temperature sections in the vicinity of the heater. The presence of water vapor has the effect of suppressing the combustion reactions of hydrogen.

Another reason why combustible and combustion-supporting components are mixed after the nitrogen and water vapor have been heated is to ensure that the heater operates in an atmosphere of neutral gases (nitrogen ($N_2$) and water vapor ($H_2O$)) so that the metal of the heater surfaces is not subjected to repeated oxidation and reduction. This ensures that the growth of oxide films is not encouraged on the heater surfaces, and also has the advantage of suppressing deterioration of the heater.

However, despite these considerations, the heater of this apparatus is subjected to severe operating conditions under which it heats a large flow rate of gases (300 liters/minute) to a high temperature (760° C.), so that heater deterioration gradually progresses and it is actually difficult to completely prevent this deterioration. It is difficult to prevent deterioration of the heater while it is being used for long periods at high temperatures, and it is also difficult to predict when it will break down. As previously mentioned in the section on the temperature control section 120, if the heater should break down by some chance, a heater breakage warning signal from the thermoregulator is automatically received by the communications means and the measurement control section 110 is automatically posted by this communications means, to enable rapid countermeasures.

Configuration around the Sensor Attachment Section

The configuration around the sensor attachment section differs between the first air/fuel ratio control system of FIG. 1 and the second air/fuel ratio control system of FIG. 10, so both configurations will be described separately below.

First Air/fuel ratio Control System

The system of FIG. 1 is constructed to detect an air/fuel ratio by one stoichiometric air/fuel ratio ($O_2$) sensor to be measured 10 and control air/fuel ratio by using a signal therefrom. The gas regulated by the gas regulation section 200 passes through the sensor attachment section 300 in which the stoichiometric air/fuel ratio ($O_2$) sensor to be measured 10 is mounted, and an attachment holder in which the sensor (air/fuel ratio detection section) 510 of the air/fuel ratio waveform measuring section 500 is mounted, until it reaches the air ratio time-average measuring section 400. A wide-range type of air/fuel ratio sensor (limiting-current type of oxygen sensor) is usually used as the sensor 510 of the air/fuel ratio waveform measuring section 500, and it has the same form as the stoichiometric air/fuel ratio ($O_2$) sensor to be measured 10. Therefore it is appropriate to use the same type of attachment holder for the sensor 510 of the air/fuel ratio waveform measuring section 500 as that for the stoichiometric air/fuel ratio ($O_2$) sensor to be measured 10.

Second Sensor Air/fuel ratio Control System

In the configuration shown in FIG. 10, air/fuel ratio are detected by the stoichiometric air/fuel ratio ($O_2$) sensors 10 and 12 provided upstream and downstream from the three-way catalyst 600, and the resultant signals are used to provide air/fuel ratio control. Thus it differs from the configuration of FIG. 1 in that the three-way catalyst 600 and another sensor attachment section 800 are provided between the sensor 510 of the air/fuel ratio waveform measuring section 500 and the air ratio time-average measuring section 400.

An air/fuel ratio control system is usually used in which a stoichiometric air/fuel ratio ($O_2$) sensor is used as the air/fuel ratio ($O_2$) sensor 10 that is placed upstream from the three-way catalyst 600, but a method using a wide-range type of air/fuel ratio ($O_2$) sensor could also be used and this apparatus can accommodate both methods.

This apparatus can also cope with a characteristic-measuring method in which stoichiometric air/fuel ratio ($O_2$) sensors to be measured are placed upstream and downstream from the three-way catalyst 600, or a characteristic-measuring method in which an air/fuel ratio ($O_2$) sensor of a known characteristic is placed in one position and a stoichiometric air/fuel ratio ($O_2$) sensor to be measured is placed in the other.

Sensor Holder

The shape of the holder in the sensor attachment section 300 will now be discussed. A stoichiometric air/fuel ratio ($O_2$) sensor to be measured is mounted in a sensor attachment holder 310, it is heated to a set temperature, and an output (electromotive force or resistance) thereof is measured. To maintain the temperature of the sensor attachment holder 310 and the gas temperature at a set temperature for measuring characteristics, a heater (not shown in the figures) is installed in the sensor attachment section 300.

It is necessary to ensure that the direction from which the supplied gas is blown onto the stoichiometric air/fuel ratio ($O_2$) sensor to be measured 10 mounted in the sensor attachment holder 310, and the flow velocity and streamlines of this gas, are the same as those that the sensor would experience when mounted in the exhaust pipe of an actual engine. It is also necessary to increase the economic advantage of this apparatus by reducing the gas flow used for the testing as far as possible. A great deal of thought has been devoted to the shape and dimensions of the sensor attachment holder of this invention, to satisfy these two conditions.

Figure 13:
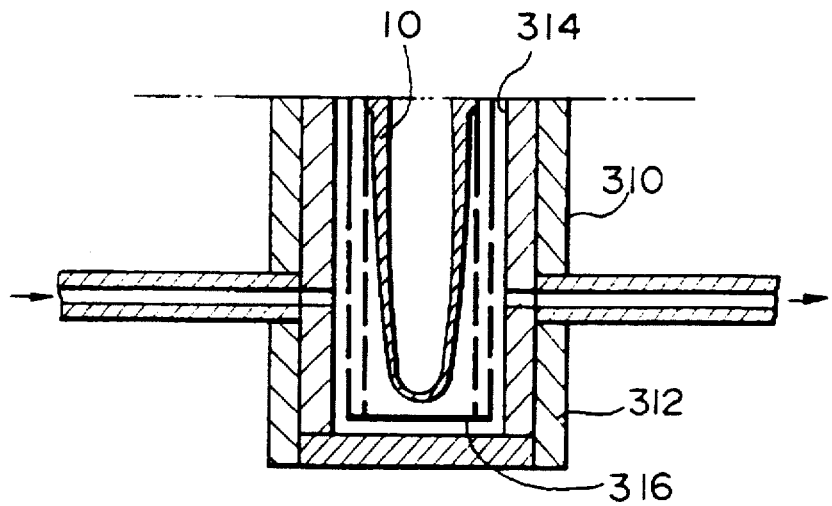
FIG. 13 is a sectional schematic explanatory diagram of a prior-art sensor attachment holder.
Figure 14:
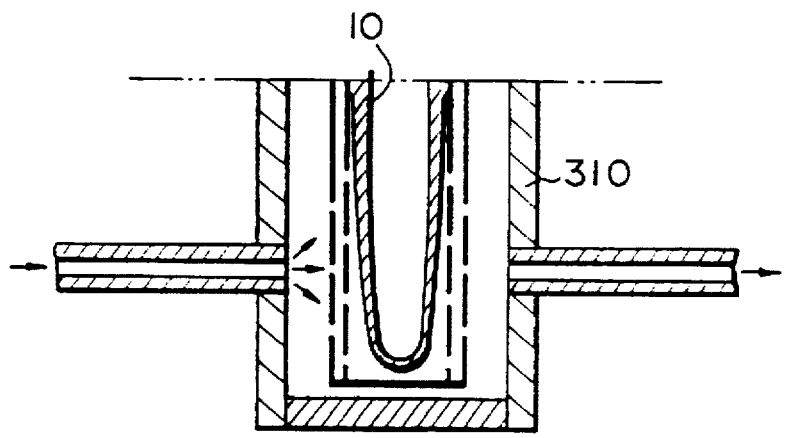
FIG. 14 is another sectional schematic explanatory diagram of the prior-art sensor attachment holder.

An examples of the cross-sectional shape of a sensor attachment holder in a prior-art apparatus is shown in FIGS. 13 and 14. In each of these figures, means for fixing the stoichiometric air/fuel ratio ($O_2$) sensor to be measured 10 in the sensor attachment holder 310, in other words, a fixing mechanism such as flanges or a screw thread, is provided in the portion above the dot-dot-dash lines, but this standard means of fixing is outside the scope of this invention so further description is omitted. In the example shown in FIG. 13, the sensor attachment holder 310 has a circular cylindrical form with one end closed, and is constructed of a main holder body 312 and a core 314 that is inserted into the holder in such a manner that it is in internal contact therewith. Note that FIG. 14 shows the holder in a state in which the core 314 is removed.

In this example, the stoichiometric air/fuel ratio ($O_2$) sensor to be measured 10 is given mechanical protection by a double-walled protective cover 316 of a circular cylindrical form that has one end closed and a large number of small holes opened therein in a regular pattern, over the outside of a tubular ceramic body with one end sealed that acts as an oxygen concentration cell. Displacing the positions of the small holes in the inner and outer covers in both the longitudinal and circumferential directions prevents deterioration to components such as the electrodes of the ceramic body that would be caused by exhaust at a high flow velocity blowing directly onto the surface of the ceramic body, and also ensures that gas is exchanged rapidly between the inside and the outside of the protective cover to obtain a transient response characteristic at the fastest possible speed.

Gas inlet and outlet pipes (the upper-right hatched portions in the figures) with small internal diameters are installed on either side of the cylinder of the sensor attachment holder 310, and gas is supplied and exhausted through these gas inlet and outlet pipes. Small holes of the same internal diameter are also provided in the core to correspond to the positions of the small internal holes of the gas inlet and outlet pipes. Gas inlet and outlet pipes of such small internal diameters are used to obtain a high gas flow rate with a small gas flow, and thus to blow a gas with a high flow velocity onto the outer surface of the stoichiometric air/fuel ratio ($O_2$) sensor to be measured.

The core 314 is provided because otherwise the streamlines of the high-flow-velocity gas would expand into a cone within the holder at the outlet end portion of the gas inlet pipeline, reducing the gas flow rate and ensuring that the gas is not blown at a high flow velocity onto the outer surface of the stoichiometric air/fuel ratio ($O_2$) sensor to be measured, thus producing conditions that are completely different from those of an actual engine and reducing the usefulness of the thus-measured characteristic (FIG. 14).

Figure 15:
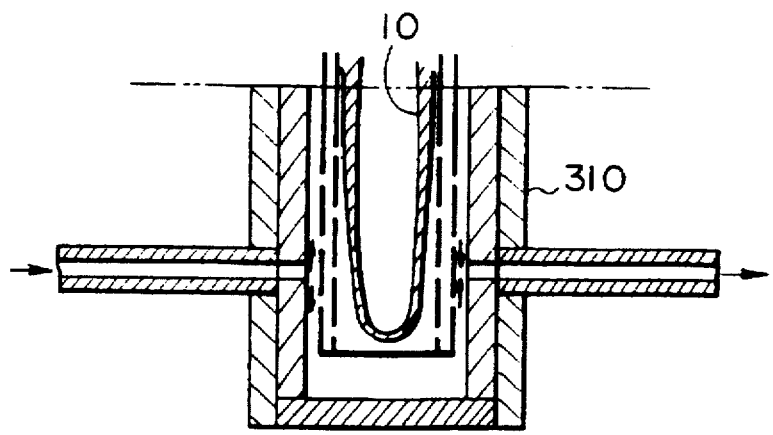
FIG. 15 is a further sectional schematic explanatory diagram of the prior-art sensor attachment holder.

If the core 314 is used, the gas streamlines are naturally prevented from expanding in a cone within the holder, so that the gas can be blown at its original high flow velocity onto the outer surface of the stoichiometric air/fuel ratio ($O_2$) sensor to be measured, which has the advantage of enabling an approximation to the high flow velocities obtained in an actual engine, albeit locally. Note, however, that this method of using the core 314 raises a problem in that the relative relationship between the positions of the opening portions of the core 314 and the corresponding positions of the small holes in the protective cover has a huge effect. In other words, if the corresponding opening portions face each other directly, the high-flow-velocity gas is not blocked at the opening portion of the core and thus it can penetrate at a high flow velocity into the protective cover (FIG. 13). On the other hand, if the opening portion of the core 314 faces a portion that is intermediate between small holes in the protective cover, the high-flow-velocity gas at the opening portion of the core strikes the protective cover so that the streamlines thereof curve (FIG. 15), and the gas penetrates through the neighboring small holes in a state in which the flow velocity thereof is reduced.

This relative relationship between the position of each opening portion of the core 314 and the corresponding small hole in the protective cover is not only strongly dependent on the design of the positioning of the cover holes in the protective cover 316 of the stoichiometric air/fuel ratio ($O_2$) sensor to be measured 10, but it is also dependent on the state in which the stoichiometric air/fuel ratio ($O_2$) sensor to be measured 10 is mounted, even when the same sensor is remounted. For example, with a flange-fixed type of stoichiometric air/fuel ratio ($O_2$) sensor to be measured, if an odd number of small holes are provided around the periphery thereof, a change of 180° in the direction in which the sensor is mounted (caused by rotating the orientation of the flange, etc) can cause a change in whether or not the small holes in the protective cover face the positions of the opening portions. Even if the direction in which the sensor is mounted is not changed by 180°, the dimensions of the flange-attachment holes are often designed to be about 1 mm larger than the diameter of the attachment bolts, to prevent a fatal state by which manufacturing errors make it impossible to attach the sensor, and it can easily happen that the mounting position is shifted by an amount equal to the difference between the dimensions. Thus the relative relationship between the small holes in the protective cover and the positions of the opening portions in the core has no small effect.

Similar faults can also occur with a screwy-thread type of stoichiometric air/fuel ratio ($O_2$) sensor to be measured, such that the force with which the screw-thread is tightened can greatly change the final stop position (angle) of the sensor.

Figure 16:
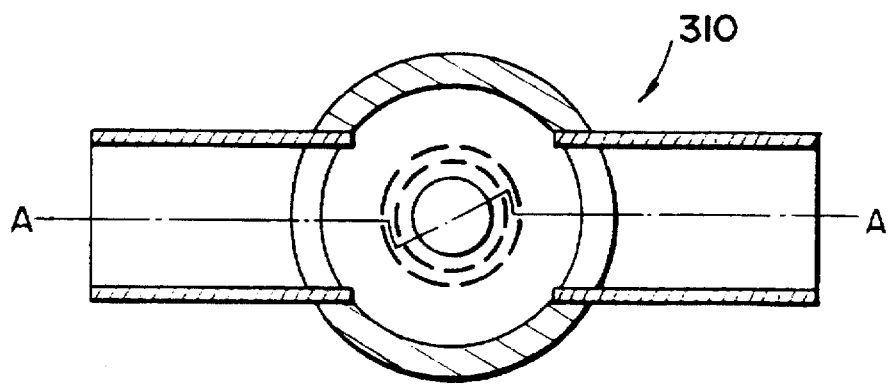
FIG. 16 is a sectional schematic explanatory diagram of a sensor attachment holder of the embodiments.
Figure 17:
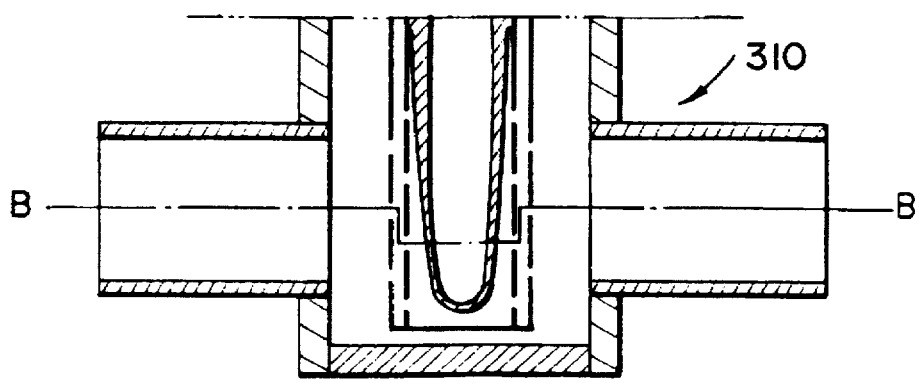
FIG. 17 is another sectional schematic explanatory diagram of the sensor attachment holder of the embodiments.

Since the sensor attachment holder 310 of the prior-art apparatus has these problems, the apparatus of this invention is improved as shown in FIGS. 16 and 17. Note that FIG. 16 is a cross section taken along the line B—B of FIG. 17, and FIG. 17 is a cross-section taken along the line A—A of FIG. 16.

1. The cross section of the gas inlet and outlet pipes is made to be rectangular so that all of the small holes of the stoichiometric air/fuel ratio ($O_2$) sensor to be measured 10 are struck by gas at the same flow velocity as the exhaust flow velocity of an actual engine, and the lateral width thereof has the same dimension as the diameter of the outer protective cover of the stoichiometric air/fuel ratio ($O_2$) sensor to be measured.

2. The cross section of the gas inlet and outlet pipes is made to be rectangular so that all of the small holes of the stoichiometric air/fuel ratio ($O_2$) sensor to be measured 10 are struck by gas at the same flow velocity as the exhaust flow velocity of an actual engine, and the height thereof has the same dimension as the entire width over which small holes are provided in the outer protective cover of the stoichiometric air/fuel ratio ($O_2$) sensor to be measured.

These specifications make it possible for the flow velocity of the gas that strikes all of the small holes in the upstream-projected surface of the outer protective cover of the stoichiometric air/fuel ratio ($O_2$) sensor to be measured 10 to be the same as the gas flow velocity within the gas inlet and outlet pipes. By making the gas flow velocity within the gas inlet and outlet pipes the same as that in an actual engine, the flow velocity of the gas that strikes all of the small holes in the upstream-projected surface of the outer protective cover of the stoichiometric air/fuel ratio ($O_2$) sensor to be measured 10 can be made to be the same as that in an actual engine.

3. The difference between the diameter of the sensor attachment holder 310 and the diameter of the outer protective cover of the stoichiometric air/fuel ratio ($O_2$) sensor to be measured 10 is made to be the same as the width of the rectangular cross section of the gas inlet and outlet pipes, so that all of the small holes in the outer protective cover of the stoichiometric air/fuel ratio ($O_2$) sensor to be measured 10 struck by gas at the same flow velocity as the exhaust flow velocity of an actual engine. This configuration makes it possible for the flow velocity of the gas flowing around the outer protective cover of the stoichiometric air/fuel ratio ($O_2$) sensor to be measured 10 to be the same as the gas flow velocity in the gas inlet and outlet pipes. As a result, the flow velocity and streamlines of the gas flowing around the outer protective cover of the stoichiometric air/fuel ratio ($O_2$) sensor to be measured 10 can be made to be the same as those in an actual engine.

A configuration that conforms to the above specifications 1 to 3 has solved the problems inherent to the sensor attachment holder of the prior-art apparatus.

Air Ratio Time-Average Measuring Section 400

The air ratio time-average measuring section 400 is designed to precisely measure the control air/fuel ratio (time-averaged value) as an air ratio (actual air/fuel ratio/ stoichiometric air/fuel ratio) while air/fuel ratio control is being performed, on the basis of an output signal of the stoichiometric air/fuel ratio ($O_2$) sensor 10 to be measured. As mentioned previously, the objective of this apparatus is to achieve highly accurate measurements with an accuracy of 0.1%, which is difficult to measure with a general-purpose automobile air/fuel ratio meter that has an accuracy of only about 2%.

An apparatus that suits this purpose is an ultra-precise air/fuel ratio meter (disclosed in Japanese Patent No. 1531810). In addition to a function as an ultra-precise air/fuel ratio meter, the apparatus of that invention automatically receives measurement instructions from a measurement control section through a communications means, automatically checks the accuracy of its own instrument and measures the control air/fuel ratio (time-averaged value), and automatically informs the measurement control section of the results through the communications means Air/fuel ratio Waveform Measuring Section 500

The air/fuel ratio waveform measuring section 500 is designed to closely follow and measure the air/fuel ratio control waveform of a gas to be measured which is varying rapidly while air/fuel ratio control is being performed, on the basis of an output signal of the stoichiometric air/fuel ratio ($O_2$) sensor to be measured. Since the air/fuel ratio of the gas to be measured varies rapidly at a rate on the order of 3 Hz, this apparatus must be able to follow these variations and measure them rapidly. With a general-purpose automobile air/fuel ratio meter (or exhaust analyzer) that samples and dehumidifies an exhaust and then measures it, long delays caused by the sampling system further delay the measurement so that a high-speed transient response characteristic cannot be obtained, and thus it is difficult to faithfully measure the air/fuel ratio control waveform of the gas to be measured.

As an air/fuel ratio waveform measuring section 500 that suits this purpose, the previously described wide-range type of air/fuel ratio sensor (limiting-current type of oxygen sensor) is placed into the passageway through which the gas to be measured is flowing (with an actual engine, this would be the exhaust pipe), and measures the air/fuel ratio directly on the basis of an output of the sensor (a current, electromotive force, or resistance), without sampling the exhaust. The apparatus of this invention is also provided with a function that automatically fetches the air/fuel ratio control waveform by the measurement control section 110.

Proof of the Effects of the System of the Embodiments

Figure 18:
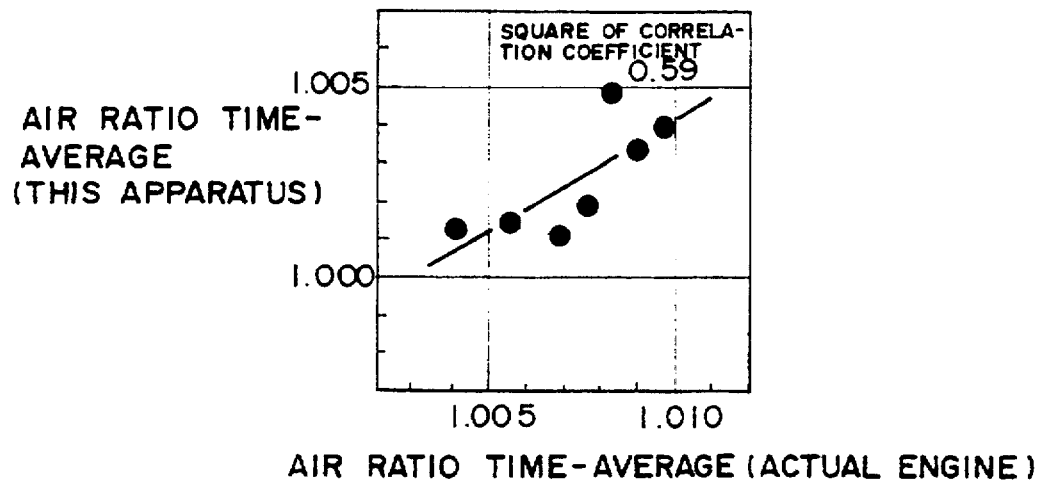
FIG. 18 is a graph of the correlation between air ratio time-averaged values measured by the apparatus of the embodiments and an actual engine.

It has already been determined that the measured control air ratio time-average of an actual engine corresponds closely to the value of exhaust emissions. The relationship between a control air ratio time-average measured by the apparatus of this invention and a control air ratio time-average measured in an actual engine under conditions of a high engine speed and a high intake pressure is shown in FIG. 18. As is clear from this figure, a good correlation was obtained between these two characteristics. Expressed as the square of the correlation coefficient ($r^2$), a high value of 0.59 was obtained.

Similarly, the relationship between an air ratio control period measured by the apparatus of this invention and an air ratio control period measured in an actual engine under conditions of a high engine speed and a high intake pressure is shown in FIG. 19. As is clear from that figure, an even better correlation was obtained between these two characteristics than that for the control air ratio time-average. Expressed as the square of the correlation coefficient ($r^2$), an extremely high value of 0.77 was obtained.

In a similar manner, the correlations between electromotive force waveforms (upper thin lines) measured by this apparatus and electromotive force waveforms (upper bold lines) measured in an actual engine under conditions of a high engine speed and a high intake pressure are shown in FIG. 23 (a) to 23(d) and FIG. 21 (e) to 21(h). As is clear from these figures, small pulsations appeared in an irregular manner in the electromotive force waveform measured in the actual engine and the iterative stability of each period was low. On the other hand, there were no small pulsations in the electromotive force waveform measured by the apparatus of this invention and thus the iterative stability of each period was high. However, if the averaged waveform for each period of the electromotive force waveform measured in the actual engine is compared with the electromotive force waveform measured by the apparatus of this invention, a good correlation can be obtained between the two electromotive force waveforms. Note that the lower portions of these figures have already been described with reference to FIG. 8.

As described above, use of the apparatus in accordance with this invention makes it possible to measure a characteristic that has a good correspondence to the characteristic obtained in an actual engine, easily and without using an actual engine. As also stated previously, this characteristic is independent of the small pulsations and variations for different periods that occur in electromotive force waveforms specific to actual engines. Thus the present invention has:

Enabled precise characteristic measurement with a high level of iterative stability Enabled the measurement of the useful characteristic values which have a good correlation which the value of exhaust emissions.

Increased the stability during characteristic measurement because there is no need to use an actual engine Reduced the cost required during characteristic measurement because there is no need to use an actual engine.

Thus this apparatus is extremely useful in manufacturing and production.

What is claimed is:

1. An apparatus for analyzing air/fuel ratio sensor characteristics, comprising:

sensor attachment means for mounting an air/fuel ratio sensor to be measured;

gas regulation means for supplying a gas to said sensor attachment means, said gas being equivalent to one of an exhaust gas from an engine and one gas component of said exhaust gas;

control means for comparing an output value from said air/fuel ratio sensor and an output reference value from a first reference air/fuel ratio sensor at a stoichiometric air/fuel ratio of said engine to obtain a deviation, obtaining from a history of said deviation over time a composition and a flow rate of the gas for correction, and for controlling said gas regulation means to control an air/fuel ratio of the gas; and air/fuel ratio measurement means for measuring a time average of the thus controlled air/fuel ratio, said air/fuel ratio measurement means comprising:

a second reference air/fuel ratio sensor for detecting the air/fuel ratio of the gas supplied from said gas regulation means, first calculation means for determining a flow rate of a supplementary gas to be added to bring the air/fuel ratio of the gas supplied from said gas regulation means to the stoichiometric air/fuel ratio based on an output value of said second reference air/fuel ratio sensor, supplementary gas control means for controlling the flow rate of the supplementary gas, and second calculation means for calculating the air/fuel ratio of the gas supplied from said gas regulation means based on the amount of said supplementary gas that is supplied, wherein a characteristic analysis of said air/fuel ratio sensor to be measured is performed based on the air/fuel ratio calculated by said second calculation means.

2. The apparatus as defined in claim 1, wherein said sensor attachment means comprises:

first sensor attachment means for mounting a first air/fuel ratio sensor to be measured, said first air/fuel ratio sensor being supplied the gas from said gas regulation means;

a three-way catalyst section provided downstream of said first sensor attachment means; and second sensor attachment means provided downstream of said three-way catalyst section, for mounting a second air/fuel ratio sensor to be measured, wherein said control means controls said gas regulation means based on outputs from said first and said second air/fuel ratio sensors to be measured.

3. The apparatus as defined in claim 2, wherein said air/fuel ratio measurement means further comprises:
   fixed flow rate supply means for separating a gas at a fixed flow rate from an exhausted gas from said sensor attachment means; and
   gas reaction means for causing the separated gas to react with said supplementary gas added by said supplementary gas control means to produce a reacted gas and supplying the reacted gas to said second reference air/fuel ratio sensor.

4. The apparatus as defined in claim 3, wherein said supplementary gas control means is constructed to supply one of a hydrogen gas and an oxygen gas selectively as said supplementary gas, said second reference air/fuel ratio sensor is constructed to detect whether said reacted gas is shifted towards one of rich and lean, said first calculation means determines whether said reacted gas is one of rich and lean from an output value of said second reference air/fuel ratio sensor, and controls said supplementary gas control means in such a manner that said oxygen gas is gradually added until said stoichiometric air/fuel ratio is achieved when said reacted gas is rich and said hydrogen gas is gradually added until said stoichiometric air/fuel ratio is achieved when said reacted gas is lean, and said second calculation means calculates and displays a time average of the air/fuel ratio when said reacted gas has reached a state in a vicinity of the stoichiometric air/fuel ratio by the addition of one of said oxygen gas and said hydrogen gas.

5. The apparatus as defined in claim 3, wherein said gas regulation means is constructed to supply a gas comprising the following gas components: nitrogen ($N_2$), water vapor ($H_2O$), carbon monoxide (CO), hydrogen ($H_2$), hydrocarbons (HC), oxygen ($O_2$), and nitric oxide (NO).

6. The apparatus as defined in claim 5, wherein said gas regulation means is constructed to supply a gas that further comprises carbon dioxide ($CO_2$).

7. The apparatus as defined in claim 6, wherein said hydrocarbon (HC) gas is at least one selected from a group consisting of ethylene ($C_2H_4$), toluene ($C_7H_8$), and propylene ($C_3H_6$).

8. The apparatus as defined in claim 2, further comprising air/fuel ratio waveform measurement means for measuring changes in a waveform of the air/fuel ratio controlled by said control means, wherein a characteristic of said air/fuel ratio sensor to be measured is analyzed based on measured waveform changes.

9. The apparatus as defined in claim 2, wherein said gas regulation means is constructed to supply a gas comprising the following gas components: nitrogen ($N_2$), water vapor ($H_2O$), carbon monoxide (CO), hydrogen ($H_2$), hydrocarbons (HC), oxygen ($O_2$), and nitric oxide (NO).

10. The apparatus as defined in claim 9, wherein said gas regulation means is constructed to supply a gas that further comprises carbon dioxide ($CO_2$).

11. The apparatus as defined in claim 9, wherein said hydrocarbon (HC) gas is at least one selected from a group consisting of ethylene ($C_2H_4$), toluene ($C_7H_8$), and propylene ($C_3H_6$).

12. The apparatus as defined in claim 9, wherein said gas regulation means is constructed to prepare a gas having a temperature, a flow velocity, a composition, and an air/fuel ratio equivalent to an engine exhaust gas under high load conditions.

13. The apparatus as defined in claim 12, wherein said gas regulation means comprises:
   liquid flow rate control means for controlling a flow rate of liquid components of said gas;
   liquid atomization means for atomizing the thus supplied liquid components to produce atomized components;
   high-speed gas flow rate control means for controlling at a high speed a supply flow rate of gaseous components of said gas; and
   mixing means for mixing said atomized components and said gaseous components, wherein said control means controls flow rates of said atomized components supplied by said liquid flow rate control means and said gaseous components supplied by said high-speed gas flow rate control means.

14. The apparatus as defined in claim 2, wherein said sensor attachment means further comprises means for heating said air/fuel ratio sensor to be measured.

15. The apparatus as defined in claim 14, wherein said control means comprises:
   memory means for setting a plurality of reference output patterns for said output reference value, air/fuel ratio control conditions for said gas regulation means, and sensor temperature control conditions for said sensor attachment means, corresponding to exhaust gas testing and measurement modes and measurement conditions of said engine;
   selection means for selecting any desired exhaust gas testing and measurement modes and measurement conditions; and
   means for reading from said memory means reference output patterns and control conditions corresponding to the thus selected exhaust gas testing and measurement modes and measurement conditions, and controlling said gas regulation means and said sensor attachment means based on the basis of read control conditions and a deviation between said read-out reference output patterns and an output from said air/fuel ratio sensor to be measured.

16. The apparatus as defined in claim 1, wherein said air/fuel ratio measurement means further comprises:
   fixed flow rate supply means for separating a gas at a fixed flow rate from an exhausted gas from said sensor attachment means; and
   gas reaction means for causing the separated gas to react with said supplementary gas added by said supplementary gas control means to produce a reacted gas and supplying the reacted gas to said second reference air/fuel ratio sensor.

17. The apparatus as defined in claim 16, wherein said supplementary gas control means is constructed to supply one of a hydrogen gas and an oxygen gas selectively as said supplementary gas, said second reference air/fuel ratio sensor is constructed to detect whether said reacted gas is shifted towards one of rich and lean, said first calculation means determines whether said reacted gas is one of rich and lean from an output value of said second reference air/fuel ratio sensor, and controls said supplementary gas control means in such a manner that said oxygen gas is gradually added until said stoichiometric air/fuel ratio is achieved when said reacted gas is rich and said hydrogen gas is gradually added until said stoichiometric air/fuel ratio is achieved when said reacted gas is lean, and said second calculation means calculates and displays a time average of the air/fuel ratio when said reacted gas has reached a state in a vicinity of the stoichiometric air/fuel ratio by the addition of one of said oxygen gas and said hydrogen gas.

18. The apparatus as defined in claim 16, wherein said gas regulation means is constructed to supply a gas comprising the following gas components: nitrogen ($N_2$), water vapor ($H_2O$), carbon monoxide (CO), hydrogen ($H_2$), hydrocarbons (HC), oxygen ($O_2$), and nitric oxide (NO).

19. The apparatus as defined in claim 18, wherein said gas regulation means is constructed to supply a gas that further comprises carbon dioxide ($CO_2$).

20. The apparatus as defined in claim 19, wherein said hydrocarbon (HC) gas is at least one selected from a group consisting of ethylene ($C_2H_4$), toluene ($C_7H_8$), and propylene ($C_3H_6$).

21. The apparatus as defined in claim 1, further comprising air/fuel ratio waveform measurement means for measuring changes in a waveform of the air/fuel ratio controlled by said control means, wherein a characteristic of said air/fuel ratio sensor to be measured is analyzed based on measured waveform changes.

22. The apparatus as defined in claim 1, wherein said gas regulation means is constructed to supply a gas comprising the following gas components: nitrogen ($N_2$), water vapor ($H_2O$), carbon monoxide (CO), hydrogen ($H_2$), hydrocarbons (HC), oxygen ($O_2$), and nitric oxide (NO).

23. The apparatus as defined in claim 22, wherein said gas regulation means is constructed to supply a gas that further comprises carbon dioxide ($CO_2$).

24. The apparatus as defined in claim 22, wherein said hydrocarbon (HC) gas is at least one selected from a group consisting of ethylene ($C_2H_4$), toluene ($C_7H_8$), and propylene ($C_3H_6$).

25. The apparatus as defined in claim 22, wherein said gas regulation means is constructed to prepare a gas having a temperature, a flow velocity, a composition, and an air/fuel ratio equivalent to an engine exhaust gas under high load conditions.

26. The apparatus as defined in claim 25, wherein said gas regulation means comprises:

liquid flow rate control means for controlling a flow rate of liquid components of said gas;

liquid atomization means for atomizing the thus supplied liquid components to produce atomized components;

high-speed gas flow rate control means for controlling at a high speed a supply flow rate of gaseous components of said gas; and mixing means for mixing said atomized components and said gaseous components, wherein said control means controls flow rates of said atomized components supplied by said liquid flow rate control means and said gaseous components supplied by said high-speed gas flow rate control means.

27. The apparatus as defined in claim 1, wherein said sensor attachment means further comprises means for heating said air/fuel ratio sensor to be measured.

28. The apparatus as defined in claim 27, wherein said control means comprises:

memory means for setting a plurality of reference output patterns for said output reference value, air/fuel ratio control conditions for said gas regulation means, and sensor temperature control conditions for said sensor attachment means, corresponding to exhaust gas testing and measurement modes and measurement conditions of said engine;

selection means for selecting any desired exhaust gas testing and measurement modes and measurement conditions; and means for reading from said memory means reference output patterns and control conditions corresponding to the thus selected exhaust gas testing and measurement modes and measurement conditions, and controlling said gas regulation means and said sensor attachment means based on read control conditions and a deviation between said read-out reference output patterns and an output from said air/fuel ratio sensor to be measured.

* * * * *